(12) United States Patent
Révész et al.

(10) Patent No.: US 6,579,874 B2
(45) Date of Patent: Jun. 17, 2003

(54) SUBSTITUTED AZOLES

(75) Inventors: László Révész, Therwil (CH); Achim Schlapbach, Lörrach (DE)

(73) Assignee: Novartis AG, Basel (CH)

(*) Notice: Subject to any disclaimer, the term of this patent is extended or adjusted under 35 U.S.C. 154(b) by 0 days.

(21) Appl. No.: 09/975,913

(22) Filed: Oct. 12, 2001

(65) Prior Publication Data

US 2002/0049220 A1 Apr. 25, 2002

Related U.S. Application Data

(63) Continuation of application No. PCT/EP00/03290, filed on Apr. 12, 2000.

(30) Foreign Application Priority Data

Apr. 14, 1999 (GB) ............................................ 9908531
Apr. 14, 1999 (GB) ............................................ 9908532

(51) Int. Cl.[7] ................... C07D 403/04; C07D 403/14; C07D 413/04; A61K 31/506
(52) U.S. Cl. ..................... 514/235.8; 514/252.19; 514/269; 514/275; 514/318; 544/122; 544/296; 544/315; 544/316; 544/324; 544/330; 544/331; 546/194
(58) Field of Search ................. 544/122, 296, 544/315, 316, 324, 330, 331; 546/194; 514/235.8, 252.19, 269, 275, 318

(56) References Cited

U.S. PATENT DOCUMENTS 5,739,143 A 4/1998 Adams et al. ............... 514/275

FOREIGN PATENT DOCUMENTS

| WO | WO 95/13067 | 5/1995 |
| WO | WO 00/69848 | * 11/2000 |

* cited by examiner

*Primary Examiner*—Deepak Rao
(74) *Attorney, Agent, or Firm*—Carol A. Loeschorn; D. Gabrielle Brouillette

(57) ABSTRACT

Compounds of formula I

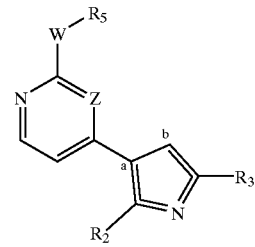

wherein the symbols have meaning as defined herein, are p38 MAP kinase inhibitors, and are useful pharmaceutically for treating TNFα and IL-1 mediated diseases, such as rheumatoid arthritis, and diseases of bone metabolism, e.g. osteoporosis.

15 Claims, No Drawings

SUBSTITUTED AZOLES

This is a continuation of International Application No. PCT/EP 00/03290, filed Apr. 12, 2000, and published in English the contents of which are incorporated herein by reference.

This invention relates to substituted azoles and to their use for treating TNFα and IL-1 mediated diseases such as rheumatoid arthritis and diseases of bone metabolism, e.g. osteoporosis.

Accordingly the present invention provides a compound of formula I

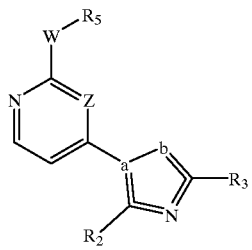

wherein
a is N or C;
b is CH when a is N, or O when a is C;
= denotes a single or a double bond dependent upon whether the azole ring is an imidazole or an oxazole ring;
Z is N or CH;
W is —$NR_6$—Y—, —O— or —S—,
where $R_6$ is H, $C_1$–$C_4$alkyl, $C_3$–$C_8$cycloalkyl, $C_3$–$C_8$cycloalkyl$C_{1-3}$alkyl, $C_6$–$C_{18}$aryl, $C_3$–$C_{18}$heteroaryl, $C_7$–$C_{19}$aralkyl or $C_4$–$C_{19}$heteroaralkyl, and —Y— is $C_1$–$C_4$alkylene or a direct bond;
$R_2$ is phenyl, optionally substituted by one or more substituents, each of which is independently selected from halo, $CF_3$, cyano, amido or thioamido, carboxylate or thiocarboxylate, $C_1$–$C_4$alkoxy, $C_1$–$C_4$alkyl, or $NH_2$ which is optionally mono- or di-N-$C_1$–$C_4$alkyl substituted;
$R_3$ is H, halogen, $C_1$–$C_{10}$alkyl, $C_1$–$C_4$alkenyl, $C_3$–$C_{10}$cycloalkyl, $C_3$–$C_{18}$heterocycloalkyl, $C_6$–$C_{18}$aryl, $C_3$–$C_{18}$heteroaryl, or methyleneaminoguanidinyl (i.e. —CH=N—NH—C(NH).$NH_2$), each of which is optionally substituted by up to 4 substituents separately selected from $C_1$–$C_4$alkyl optionally substituted by hydroxy, halogen, halo-substitued-$C_1$–$C_4$alkyl, hydroxy, $C_1$–$C_4$alkoxy, $C_1$–$C_4$alkylthio, carboxy, optionally $C_1$–$C_6$alkyl or $C_1$–$C_6$alkoxy substituted carbonyl, optionally mono- or di-N-$C_1$–$C_4$alkyl substituted amino, or by N-heterocyclyl containing from 5 to 7 ring atoms and optionally containing a further hetero atom;
$R_5$ is $C_6$–$C_{18}$aryl, $C_3$–$C_{18}$heteroaryl, or $C_3$–$C_{12}$cycloalkyl each of which is optionally substituted by up to 4 substituents separately selected from $C_1$–$C_4$alkyl halogen, halo-substitued-$C_1$–$C_4$alkyl, hydroxy, $C_1$–$C_4$alkoxy, $C_1$–$C_4$alkythio, or optionally mono- or di-N-$C_1$–$C_4$alkyl substituted amino, or by N-heterocyclyl containing from 5 to 7 ring atoms and optionally containing a further hetero atom, and esters thereof and acid addition salts thereof.

Above and elsewhere in the present description the terms halo or halogen denote I, Br, Cl or F.

In a particular embodiment the invention provides a 4-phenyl-5-[(2-substituted)-4-pyrimidyl or -pyridyl]-oxazole of formula I, or a pharmaceutically-acceptable and -cleavable ester thereof or acid addition salt thereof (wherein the numbering of the atoms of the oxazole ring is shown below in formula II.)

Thus in a particular embodiment the invention provides compound of formula II

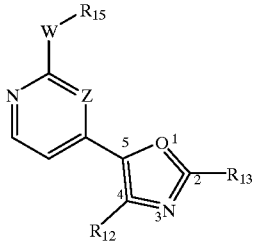

wherein
Z is N or CH;
W is —$NR_6$—Y—, —O— or —S—,
where $R_6$ is H, $C_1$–$C_4$alkyl, $C_3$–$C_8$cycloalkyl, $C_3$–$C_8$cycloalkyl$C_1$–$C_3$alkyl, $C_6$–$C_{18}$aryl, $C_3$–$C_{18}$heteroaryl, $C_7$–$C_{19}$aralkyl or $C_4$–$C_{19}$heteroaralkyl, and —Y— is $C_1$–$C_4$alkylene or a direct bond;
$R_{12}$ is phenyl optionally substituted by one or more substituents, each of which is independently selected from halo, $CF_3$, cyano, amido or thioamido, carboxylate or thiocarboxylate, $C_1$–$C_4$alkoxy, $C_1$–$C_4$alkyl, or $NH_2$ which is optionally mono- or di-N-$C_1$–$C_4$alkyl substituted;
$R_{13}$ is H, halogen, $C_1$–$C_{10}$alkyl, $C_1$–$C_4$alkenyl, $C_3$–$C_{10}$cycloalkyl, $C_3$–$C_{18}$heterocycloalkyl, $C_6$–$C_{18}$aryl, $C_3$–$C_{18}$heteroaryl, or methyleneaminoguanidinyl (i.e. —CH=N—NH—C(NH).$NH_2$), each of which is optionally substituted by up to 4 substituents separately selected from $C_1$–$C_4$alkyl optionally substituted by hydroxy, halogen, halo-substitued-$C_1$–$C_4$alkyl, hydroxy, $C_{1-4}$alkoxy, $C_{1-4}$alkylthio, carboxy, optionally $C_1$–$C_6$alkyl or $C_1$–$C_6$alkoxy substituted carbonyl, optionally mono- or di-N-$C_{1-4}$alkyl substituted amino, or by N-heterocyclyl containing from 5 to 7 ring atoms and optionally containing a further hetero atom;
$R_{15}$ is $C_6$–$C_{18}$aryl, $C_3$–$C_{18}$heteroaryl, or $C_3$–$C_{12}$cycloalkyl each of which is optionally substituted by up to 4 substituents separately selected from $C_1$–$C_4$alkyl, halogen, halo-substitued-$C_1$–$C_4$alkyl, hydroxy, $C_1$–$C_4$alkoxy, $C_1$–$C_4$alkylthio, or optionally mono- or di-N-$C_1$–$C_4$alkyl substituted amino, or by N-heterocyclyl containing from 5 to 7 ring atoms and optionally containing a further hetero atom,
and pharmaceutically-acceptable and -cleavable esters thereof and acid addition salts thereof.

When $R_{13}$ is heteroaryl it is preferably pyridyl (e.g. 4-pyridyl) or pyrimidyl, each optionally substituted, e.g. by up to 2 substituents, separately selected from $C_1$–$C_4$alkyl optionally substituted by hydroxy, halogen, hydroxy, $C_1$–$C_4$alkoxy, carboxy, optionally $C_1$–$C_6$-alkyl or $C_1$–$C_6$alkoxy substituted carbonyl, or optionally mono- or di-N-$C_1$–$C_4$alkyl substituted amino.

When $R_{13}$ is cycloalkyl it is preferably $C_3$–$C_8$, especially $C_5$–$C_6$cycloalkyl (e.g. cyclohexyl), optionally substituted, e.g. by 1 or 2 substituents, separately selected from $C_1$–$C_4$alkyl, halogen hydroxy, $C_1$–$C_4$alkoxy, or optionally mono- or di-N-$C_1$–$C_4$alkyl substituted amino.

When $R_{13}$ is heterocycloalkyl it is preferably N-heterocyclyl containing from 5 to 7 ring atoms and optionally containing a further hetero atom, e.g. N or O, and is optionally substituted, e.g. by 1 or 2 substituents, separately selected from $C_1$–$C_4$alkyl optionally substituted by hydroxy, halogen, hydroxy, $C_1$–$C_4$alkoxy, carboxy, optionally $C_1$–$C_6$alkyl or $C_1$–$C_6$alkoxy substituted carbonyl, or optionally mono- or di-N-$C_{1-4}$substituted amino.

When $R_{15}$ is aryl it is preferably phenyl. When $R_{15}$ is cycloalkyl, it is preferably $C_3$–$C_7$cycloalkyl, e.g. cylopropyl, cyclopentyl, cyclohexyl or cycloheptyl. $R_{15}$ may be unsubstituted or substituted, conveniently mono-substituted, e.g. phenyl conveniently meta or para substituted, by halogen, $C_1$–$C_{10}$alkyl, halo-substitued $C_1$–$C_{10}$alkyl, $C_1$–$C_{10}$alkoxy, hydroxy, or —$NR_7R_8$, where $R_7$ and $R_8$ are idependently H, $C_1$–$C_6$alkyl, $C_6$–$C_{10}$aryl, $C_6$–$C_{10}$heteroaryl, $C_7$–$C_{11}$aralkyl or $C_7$–$C_{11}$heteroaralkyl.

When Y is $C_1$–$C_4$ alkylene, it is preferably $C_1$–$C_2$ alkylene, and is optionally substituted, e.g. by $C_1$–$C_4$alkyl (e.g. methyl), halogen, hydroxy, $C_1$–$C_4$alkoxy, or amino.

More preferably $R_{12}$ is phenyl substituted, preferably mono- or di-substituted, by halogen or a halogen-containing group, e.g. 4-fluorophen-1-yl, or 3-$CF_3$, 3-Cl, or 3,4-difluoro substituted.

More preferably $R_{13}$ is H, $C_{1-6}$alkyl, $C_1$–$C_4$alkenyl, phenyl, pyridyl, morpholinyl, piperidinyl, piperazinyl, or N-mono- or di-$C_{1-4}$alkylamino, each of which is optionally substituted, e.g. by up to 2 substituents, separately selected from $C_1$–$C_4$alkyl optionally substituted by hydroxy, halogen, hydroxy, $C_1$–$C_4$alkoxy, carboxy, optionally $C_1$–$C_6$alkyl or $C_1$–$C_6$alkoxy substituted carbonyl, or optionally mono- or di-N-$C_1$–$C_4$alkyl substituted amino.

Preferably W is —NH—Y'—, —O— or —S—, where Y' is —$CH_2$—, —$CH_2$—$CH_2$—, —$CH(CH_3)$— or a direct bond Thus in preferred embodiments the invention provides a compound of formula II'

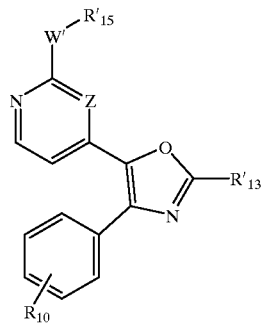

II' wherein
$R_{15}$' is phenyl or $C_3$–$C_7$cycloalky each of which is optionally mono-substituted by halogen, $C_1$–$C_{10}$alkyl, $C_1$–$C_{10}$alkoxy, hydroxy, trihalomethyl or —$NR_7R_8$, where $R_7$ and $R_8$ are independently H, $C_1$–$C_6$alkyl, $C_6$–$C_{10}$aryl, $C_6$–$C_{10}$heteroaryl $C_7$–$C_{11}$aralkyl or $C_7$–$C_{11}$heteroaralkyl;

$R_{10}$ is halogen, $CF_3$, cyano, amido, thioamido, amino $C_{1-6}$alkyl;

$R_{13}$' is H, $C_1$–$C_6$alkyl, $C_1$–$C_4$alkenyl, phenyl, pyridyl, morpholinlyl, piperidinyl, piperazinyl, or N-mono- or di-$C_1$–$C_4$alkylamino, each of which is optionally substituted, e.g. by up to 2 substituents, separately selected from $C_1$–$C_4$alkyl optionally substituted by hydroxy, halogen, hydroxy, $C_1$–$C_4$alkoxy, carboxy, optionally $C_1$–$C_6$alkyl or $C_1$–$C_6$alkoxy substituted carbonyl or optionally mono- or di-N-$C_1$–$C_4$alkyl substituted amino;

Z is N or CH and
W' is —NH—Y'—, —O— or —S—, where Y' is —$CH_2$—, —$CH_2$—$CH_2$—, —$CH(CH_3)$— or a direct bond, and pharmaceutically-acceptable and -cleavable esters thereof and acid addition salts thereof.

Preferably $R_{15}$' is unsubstituted or monosubstituted by halogen, $C_{1-4}$alkyl (e.g. methyl), $C_{1-4}$alkoxy (e.g. methoxy), hydroxy or $CF_3$.

Preferably $R_{10}$ is halogen, e.g. F, or $CF_3$.

Preferably $R_{13}$' is $C_1$–$C_6$alkyl, morpholinyl, piperidinyl, piperazinyl, or N-mono- or di-$C_1$–$C_4$alkylamino, each of which is optionally substituted, e.g. by up to 2 substituents, separately selected from $C_1$–$C_4$alkyl optionally substituted by hydroxy, carboxy, optionally $C_1$–$C_6$alkyl or $C_1$–$C_6$alkoxy substituted carbonyl or amino.

Preferably W' is —NH—Y"— where —Y"— is —$CH_2$, —$CH(CH_3)$— or a direct bond.

The Invention includes the following compounds of formula II:

4-(4-Fluorophenyl)-5-(2-[1-(S)-phenylethyl]amino-4-pyrimidyl)-2-N-morpholinyloxazole;
4-(4-Fluorophenyl)-5-(2-[1-(S)-phenylethyl]amino-4-pyrimidyl)-2-N-piperidinyloxazole;
4-(4-Fluorophenyl)-5-(2-[1-(S)-phenylethyl]amino-4-pyrimidyl)-2-(4-ethoxycarbonylpiperazin-1-yl)oxazole;
4-(4-Fluorophenyl)-5-(2-[1-(S)-phenylethyl]amino-4-pyrimidyl)-2-(4-methyl-piperidine-1-yl)oxazole;
4-(4-Fluorophenyl)-5-(2-[1-(S)-phenylethyl]amino-4-pyrimidyl)-2-(4-ethyl-piperazin-1-yl)oxazole;
4-(4-Fluorophenyl)-5-(2-[1-(S)-phenylethyl]amino-4-pyrimidyl)-2-N,N-diethyl-aminooxazole;
4-(4-Fluorophenyl)-5-(2-[1-(S)-phenylethyl]amino-4-pyrimidyl)-2-(4-NH-piperidine-1-yl)oxazole;
4-(4-Fluorophenyl)-5-(2-[1-(S)-phenylethyl]amino-4-pyrimidyl)-2-(4-N-acetyl-piperidine-1-yl)oxazole;
4-(4-Fluorophenyl)-5-(2-[1-(S)-phenylethyl]amino-4-pyrimidyl)-2-(4-pyridyl)oxazole;
4-(4-Fluorophenyl)-5-(2-[1-(S)-phenylethyl]amino-4-pyrimidyl)-2-(1-piperazinyl)oxazole;
4-(4-Fluorophenyl)-5-(2-[1-(S)-phenylethyl]amino-4-pyrimidyl)-2-(1-amino-1-methyl)ethyloxazole;
4-(4-Fluorophenyl)-5-(2-[1-(S)-phenylethyl]amino-4-pyrimidyl)-2-(1-hydroxy-4-methylpiperidine-1-yl)oxazole;
4-(4-Fluorophenyl)-2-(1-hydroxy-4-methyl)piperidine-1-yl)-5-(2-[cyclopropylmethyl]amino-4-pyridyl)oxazole;
4-(4-Fluorophenyl)-2-(4-NH-piperidine-1-yl)-5-(2-(S)-phenylethyl)amino-4-pyridyl)oxazole;
4-(4-Fluorophenyl)-2-(4-NH-piperidine-1-yl)-5-(2-cyclopropylmethylamino-4-pyridyl)oxazole;
4-(4-Fluorophenyl)-2-(4-N-(2-hydroxy-2-methyl)propylpiperidine-1-yl)-5-(2-cyclopropylmethylamino-4-pyridyl)oxazole;
4-(4-Fluorophenyl)-5-(2-cyclopropylmethylamino-4-pyrimidyl)-2-(4-NH-piperidine-1-yl)oxazole;
4-(4-Fluorophenyl)-2-(1-hydroxy-4-ethyl)piperidin-1-yl)-5-(2-cyclohexylamino-4-pyridyl)oxazole;
4-(4-Fluorophenyl)-2-(1-hydroxy-4-ethyl-piperidin-1-yl)-5-(2-cyclopropylamino-4-pyridyl)oxazole;
4-(4-Fluorophenyl)-2-(4-N-(2-hydroxy-2-methyl)propylpiperidine-1-yl)-5-(2-cyclohexylamino-4-pyridyl)oxazole;
4-(4-Fluorophenyl)-2-(4-N-(2-hydroxy-2-methyl)propylpiperidine-1-yl)-5-(2-cyclopropylamino-4-pyridyl)oxazole;
4-(4-Fluorophenyl)-2-(4-N-(2-hydroxy-2-methyl)propylpiperidine-1-yl)-5-(2-(1-(S)-phenylethyl)amino-4-pyridyl)oxazole;
4-(4-Fluorophenyl)-2-(4-NH-piperidine-1-yl)-5-(2-cyclohexylamino-4-pyridyl)oxazole, and
4-(4-Fluorophenyl)-2-(4-N-(2-hydroxy-2-methyl)propylpiperidine-1-yl)-5-(2-(1-(S)-phenylethyl)amino-4-pyridyl)oxazole.

In a further particular embodiment the invention provides a 1-[(2-substituted)-4-pyrimidyl]-2-phenyl-imidazole of formula I or a pharmaceutically-acceptable and -cleavable ester thereof or acid addition salt thereof. (The numbering of the atoms of the imidazole ring is shown below in formula III.)

Thus in yet further particular embodiments the invention provides a compound of formula III

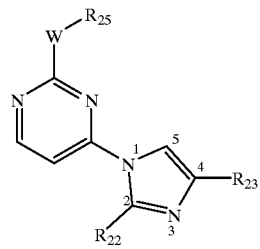

wherein

W is —NR$_6$—Y—, —O— or —S—,
where R$_6$ is H, C$_1$–C$_4$alkyl, C$_3$–C$_8$cycloalkyl, C$_3$–C$_8$cycloalkylC$_1$–C$_3$alkyl, C$_6$–C$_{18}$aryl, C$_3$–C$_{18}$heteroaryl, C$_7$–C$_{19}$aralkyl or C$_4$–C$_{19}$heteroaralkyl, and —Y— is C$_1$–C$_4$alkylene or a direct bond;

R$_{22}$ is phenyl, optionally substituted by one or more substituents, each of which is independently selected from halo, CF$_3$, cyano, amido or thioamido, carboxylate or thiocarboxylate, C$_1$–C$_4$alkoxy, C$_1$–C$_4$alkyl, or NH$_2$ is which is optionally mono- or di-N-C$_1$–C$_4$alkyl substituted;

R$_{23}$ is H, halogen, C$_1$–C$_{10}$alkyl, C$_1$–C$_4$alkenyl, C$_3$–C$_{10}$cycloalkyl, C$_3$–C$_{18}$heterocycloalkyl, C$_6$–C$_{18}$aryl, C$_3$–C$_{18}$heteroaryl or methyleneaminoguanidinyl (i.e. —CH=N—NH—C(NH)NH$_2$), each of which may be optionally substituted by up to 4 substituents separately selected from C$_1$–C$_4$alkyl optionally substituted by hydroxy, halogen, halo-substituted-C$_1$–C$_4$alkyl, hydroxy, C$_1$–C$_4$alkoxy, C$_1$–C$_4$alkylthio, carboxy, optionally C$_1$–C$_6$alkyl or C$_1$–C$_6$alkoxy substitued carbonyl, optionally mono- or di-N-C$_1$–C$_4$alkyl substituted amino, or by N-heterocyclyl containing from 5 to 7 ring atoms and optionally containing a further hetero atom;

R$_{25}$ is C$_6$–C$_{18}$aryl C$_3$–C$_{18}$heteroaryl, or C$_3$–C$_{12}$cycloalkyl each of which is optionally substituted by up to 4 substituents separately selected from C$_1$–C$_4$alkyl, halogen, halo-substituted-C$_1$–C$_4$alkyl, hydroxy, C$_1$–C$_4$alkoxy, C$_1$–C$_4$alkylthio, or optionally mono- or di-N-C$_1$–C$_4$alkyl substituted amino, or by N-hetereocyclyl containing from 5 to 7 ring atoms and optionally containing a further hetero atom, and pharmaceutically-acceptable and -cleavable esters thereof and acid addition salts thereof.

When R$_{23}$ is aryl, it is preferably phenyl optionally substituted, e.g. by up to 2 substituents, separately selected from C$_1$–C$_4$alkyl optionally substituted by hydroxy, halogen, hydroxy, C$_1$–C$_4$alkoxy, carboxy, optionally C$_1$–C$_6$alkyl or C$_1$–C$_6$alkoxy substituted carbonyl optionally mono- or di-N-C$_1$–C$_4$alkyl substituted amino, or by N-heterocyclyl containing from 5 to 7 ring atoms and optionally containing a further hetero atom.

When R$_{23}$ is heteroaryl it is preferably pyridyl (e.g. 4-pyridyl or 3-pyridyl), pyrimidyl, thienyl, furyl, or benzofuryl, each optionally substituted, e.g. by up to 2 substituents, separately selected from C$_1$–C$_4$alkyl optionally substituted by hydroxy, halogen, hydroxy, C$_1$–C$_4$alkoxy, carboxy, optionally C$_1$–C$_6$alkyl or C$_1$–C$_6$alkoxy substituted carbonyl optionally mono- or di-N-C$_1$–C$_4$alkyl substituted amino, or by N-heterocyclyl containing from 5 to 7 ring atoms and optionally containing a further hetero atom.

When R$_{23}$ is cycloalkyl it is preferably C$_3$–C$_8$, especially C$_5$–C$_6$cycloalkyl (e.g. cyclohexyl), optionally substituted, e.g. by 1 or 2 substituents, separately selected from C$_{1-4}$alkyl, halogen, hydroxy, C$_{1-4}$alkoxy, or optionally mono- or di-N-C$_{1-4}$alkyl substituted amino.

When R$_{23}$ is heterocycloalkyl it is preferably N-heterocyclyl containing from 5 to 7 ring atoms and optionally containing a further hetero atom, e.g. N or O, and is optionally substituted, e.g. by up to 2 substituents, separately selected from C$_1$–C$_4$alkyl optionally substituted by hydroxy, halogen, hydroxy, C$_1$–C$_4$alkoxy, carboxy, optionally C$_1$–C$_6$alkyl or C$_1$–C$_6$alkoxy substituted carbonyl optionally mono- or di-N-C$_1$–C$_4$alkyl substituted amino, or by N-heterocyclyl containing from 5 to 7 ring atoms and optionally containing a further hetero atom.

When R$_{25}$ is aryl it is preferably phenyl. When R$_{25}$ is cycloalkyl it is preferably C$_3$–C$_7$cycloalkyl, e.g. cylopropyl cyclopentyl, cyclohexyl or cycloheptyl. R$_{25}$ may be unsubstituted or substituted, conveniently mono-substituted, e.g. phenyl conveniently meta or para substituted, by halogen, C$_1$–C$_{10}$alkyl halo-substituted C$_1$–C$_{10}$alkyl, C$_1$–C$_{10}$alkoxy, hydroxy or —NR$_7$R$_8$, where R$_7$ and R$_8$ are independently H, C$_1$–C$_6$alkyl, C$_6$–C$_{10}$aryl, C$_6$–C$_{10}$hetereoaryl, C$_7$–C$_{11}$aralkyl or C$_7$–C$_{11}$hetereoaralkyl.

When Y is C$_1$–C$_4$ alkylene, it is preferably C$_1$–C$_2$ alkylene, and is optionally substituted, e.g. by C$_1$–C$_4$alkyl (e.g. methyl), halogen, hydroxy, alkoxy, or amino.

More preferably R$_{22}$ is phenyl substituted preferably mono- or disubstituted, by halogen or a halogen-containing group, e.g. 4-fluorophen-1-yl, or 3-CF$_3$, 3Cl, or 3,4-difluoro substituted phenyl.

More preferably R$_{23}$ is H, halogen, C$_{1-6}$alkyl, vinyl phenyl, pyridyl, pyrimidyl, benzofuryl, furyl, thienyl morpholinyl, piperidinyl, nortropanyl, piperazinyl, methyleneaminoguanidinyl or N-mono- or di-C$_1$–C$_4$alkylamino, each of which is optionally substituted, e.g. by up to 2 substituents, separately selected from C$_1$–C$_4$alkyl optionally substituted by, halogen, hydroxy, C$_1$–C$_4$alkoxy, carboxy, optionally C$_1$–C$_6$alkyl or C$_1$–C$_6$alkoxy substituted carbonyl optionally mono- or di-N-C$_1$–C$_4$alkyl substituted amino, or by N-heterocyclyl containing from 5 to 7 ring atoms and optionally containing a further hetero atom.

Preferably X is —NH—Y'—, —O— or —S—, where Y' is —CH$_2$—, —CH$_2$—C$_2$—, —CH(CH$_3$)— or a direct bond. In particular X is —NH—CH(CH$_3$)—.

Thus in preferred embodiments the invention provides a compound of formula III'

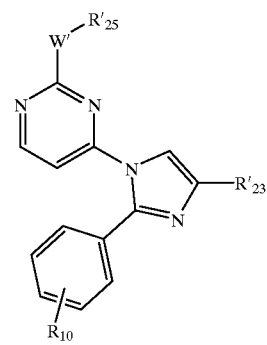

wherein

R'$_{25}$ is phenyl or C$_3$–C$_7$cycloalkyl each of which is optionally mono-substituted by halogen, C$_1$–C$_{10}$alkyl, C$_1$–C$_{10}$alkoxy, hydroxy, trihalomethyl or —NR$_7$R$_8$, where $R_7$ and $R_8$ are independently H, $C_1$–$C_6$alkyl, $C_6$–$C_{10}$aryl, $C_6$–$C_{10}$heteroaryl $C_7$–$C_{11}$aralkyl or $C_7$–$C_{11}$heteroaralkyl;

$R_{10}$ is halogen, $CF_3$, cyano, amido, thioamido, amino or $C_1$–$C_6$alkyl;

$R'_{23}$ is H, halogen, $C_1$–$C_6$alkyl, vinyl, phenyl, pyridyl, pyrimidyl, benzofuryl, furyl, thienyl, morpholinyl, piperidinyl, nortropanyl, piperazinyl, methyleneaminoguanidinyl or N-mono- or di-$C_1$–$C_4$alkylamino, each of which is optionally substituted, e.g. by up to 2 substituents, separately selected from $C_1$–$C_4$alkyl optionally substituted by hydroxy, halogen, hydroxy, $C_1$–$C_4$alkoxy, carboxy, optionally $C_1$–$C_6$alkyl or $C_1$–$C_6$alkoxy substituted carbonyl, optionally mono- or di-N-$C_1$–$C_4$alkyl substituted amino, or by N-heterocyclyl containing from 5 to 7 ring atoms and optionally containing a further hetero atom, and W' is —NH—Y'—, —O— or —S—, where Y' is —$CH_2$—, —$CH_2$—$CH_2$—, —CH($CH_3$)— or a direct bond, and pharmaceutically-acceptable and -cleavable esters thereof and acid addition salts thereof.

Preferably $R'_{25}$ is unsubstituted or monosubstituted by halogen, $C_{1-4}$alkyl, (e.g. methyl), $C_{1-4}$alkoxy (e.g. methoxy), hydroxy or $CF_3$.

Preferably $R'_{23}$ is halogen, vinyl, phenyl, pyridyl, pyrimidyl, benzofuryl, furyl, thienyl, piperidinyl, nortropanyl, or methyleneaminoguanidinyl, each of which is optionally substituted, e.g. by up to 2 substituents, separately selected from $C_1$–$C_4$alkyl optionally substituted by hydroxy, halogen, hydroxy, $C_1$–$C_4$alkoxy, carboxy, optionally $C_1$–$C_6$alkyl or $C_1$–$C_6$alkoxy substituted carbonyl optionally mono- or di-N-$C_1$–$C_4$alkyl substituted amino, or by N-heterocyclyl containing from 5 to 7 ring atoms and optionally containing a further hetero atom Preferably $R_{10}$ is halogen, e.g. F, or $CF_3$.

Preferably ' is —NH—Y'" where Y'" is —CH($CH_3$)— or a direct bond.

The Invention includes the following compounds of formula III:

3-Bromo-2-(4-fluorophenyl)-1-(2-[1-(S)-phenylethyl] amino-4-pyrimidyl)imidazole;

4-Bromo-2-(4-fluoromethylphenyl)-1-(2-cyclohexylamino-4-pyrimidyl)imidazole;

4-Bromo-2-(3-trifluoromethylphenyl)-1-(2-cyclopentylamino-4-pyrimidyl)imidazole;

4-Bromo-2-(3-trifluoromethylphenyl)-1-(2-cyclopropylamino-4-pyrimidyl)imidazole;

2-(4-Fluorophenyl)-4-(1-methyl-4-hydroxypiperidin-4-yl)-1-(2-[1-(S)-phenyl-ethyl]amino-4-pyrimidyl)imidazole;

2-(4-Fluorophenyl)-1-(2-[1-(S)-phenyl-ethyl]amino-4-pyrimidyl) 4-vinylimidazole;

2-(4-Fluorophenyl)-1-(2-[1-(S)-phenyl-ethyl]amino-4-pyrimidyl) 4-(4-pyridyl)-imidazole;

2-(4-Fluorophenyl)-1-(2-[1-(S)-phenyl-ethyl]amino-4-pyrimidyl) 4-(2-pyridyl)-imidazole;

2-(4-Fluorophenyl)-1-(2-[1-(S)-phenyl-ethyl]amino-4-pyrimidyl) 4-(3-pyridyl)-imidazole;

2-(4-Fluorophenyl)-1-(2-[1-(S)-phenyl-ethyl]amino-4-pyrimidyl) 4-(2-thienyl)-imidazole;

2-(4-Fluorophenyl)-1-(2-[1-(S)-phenyl-ethyl]amino-4-pyrimidyl) 4-(2-furyl)-imidazole;

2-(4-Fluorophenyl)-1-(2-[1-(S)-phenyl-ethyl]amino-4-pyrimidyl) 4-(2-amino)pyrimidylimidazole;

2-(4-Fluorophenyl)-1-(2-[1-(S)-phenyl-ethyl]amino-4-pyrimidyl) 4-(2-hydroxy)pyrimidylimidazole;

2-(4-Fluorophenyl)-1-(2-[1-(S)-phenyl-ethyl]amino-4-pyrimidyl) 4-(2-morpholinyl)pyrimidylimidazole;

2-(4-Fluorophenyl)-1-(2-[1-(S)-phenyl-ethyl]amino-4-pyrimidyl)-4-(3-thienyl)-imidazole;

2-(4-Fluorophenyl)-1-(2-[1-(S)-phenyl-ethyl]amino-4-pyrimidyl)-4-(2-benzofuryl)-imidazole;

2-(4-Fluorophenyl)-1-(2-[1-(S)-phenyl-ethyl]amino-4-pyrimidyl)-4-(5-chlorothiophen-2-yl)imidazole;

2-(4-Fluorophenyl)-1-(2-[1-(S)-phenyl-ethyl]amino-4-pyrimidyl)-4-(4-methoxyphenyl)imidazole;

2-(4-Fluorophenyl)-1-(2-[1-(S)-phenyl-ethyl]amino-4-pyrimidyl)-4-(4-fluorophenyl)imidazole;

2-(4-Fluorophenyl)-1-(2-[1-(S)-phenyl-ethyl]amino-4-pyrimidyl)-4-(3-chloro-4-fluorophenyl)imidazole;

2-(4-Fluorophenyl)-1-(2-[1-(S)-phenyl-ethyl]amino-4-pyrimidyl)-4-(3-chloro phenyl)imidazole;

2-(4-Fluorophenyl)-1-(2-[1-(S)-phenyl-ethyl]amino-4-pyrimidyl)-4-(4-methyleneaminoguanidinyl-imidazole;

2-(4-Fluorophenyl)-1-(2-[1-(S)-phenylethyl]amino-4-pyrimidyl)-4-(4-ethoxycarbonyl)piperidine-1-yl imidazole;

2-(4-Fluorophenyl)-1-(2-[1-(S)-phenylethyl]amino-4-pyrimidyl)-4-piperidine-1-yl imidazole;

2-(4-Fluorophenyl)-1-(2-[1-(S)-phenylethyl]amino-4-pyrimidyl)-4-(4-formyl)-piperidine-1-yl imidazole;

2-(4-Fluorophenyl)-1-(2-[1-(S)-phenylethyl]amino-4-pyrimidyl)-4-(4-(2-hydroxy-2-methyl)propylpiperidine-1-yl imidazole;

2-(4-Fluorophenyl)-1-(2-[1-(S)-phenylethyl]amino-4-pyrimidyl)-4-(4-methyl)-piperidine-1-yl imidazole;

2-(4-Fluorophenyl)-1-(2-[1-(S)-phenylethyl]amino-4-pyrimidyl)-4-(1-hydroxy-4-tert.butyloxycarbonyl) piperidine-1-yl imidazole;

2-(4-Fluorophenyl)-1-(2-[1-(S)-phenylethyl]amino-4-pyrimidyl)-4-(1-hydroxy)-piperidine-1-yl imidazole;

2-(4-Fluorophenyl)-1-(2-[1-(S)-phenylethyl]amino-4-pyrimidyl)-4-(3a-hydroxy-N-tert.butyloxycarbonylnortropan-3b-yl) imidazole;

2-(4-Fluorophenyl)-4-(1-methyl-4-hydroxypiperidin-4-yl)-1-(2-cyclohexylamino-4-pyrimidinyl)imidazole;

2-(3-Trifluoromethylphenyl)-4-(1-methyl-4-hydroxypiperidin-4-yl)-1-(2-cyclopropylamino-4-pyrimidyl)imidazole;

2-(3-Trifluoromethylphenyl)-4-(1-methyl-4-hydroxypiperidin-4-yl)-1-(2-cyclopentylamino-4-pyrimidyl)imidazole;

2-(4-Fluorophenyl)-1-(2-cyclopentyl)amino-4-pyrimidyl)-4-(4-(2-hydroxy-2-methyl)propylpiperidine-1-yl imidazole;

2-(4-Fluorophenyl)-1-(2-(1-(S)-phenylethyl)amino-4-pyrimidyl)-4-(3a-hydroxy-nortropan-3b-yl) imidazole; and 2-(4-Fluorophenyl)-1-(2-(1-(S)-phenylethyl)amino-4pyrimidyl)-4-(4-acetyl)piperidine-1-yl imidazole.

It will be appreciated that when Y is substituted alkylene the compounds of formulae II and III contain at least 1 assymetric carbon atom with this alkylene moiety. The resulting diastereoisomers and enantiomers are encompassed by the instant invention. Preferably, however, e.g. for pharmaceutical use in accordance with the invention, the compounds of formulae II and III, are provided in pure or substantially pure epimeric form, e.g. as compositions in which the compounds are present in a form comprising at least 90%, e.g. preferably at least 95% of a single epimer (i.e. comprising less than 10%, e.g. preferably less than 5% of other epimeric forms). Preferred epimeric compounds of formulae II and III are described hereinafter in the Examples.

In the present description the terms such as "$C_3$–$C_{18}$heteroaryl, $C_4$–$C_{19}$heteroaralkyl and $C_3$–$C_{18}$heterocycloalkyl" denote heteroaryl, heteroaralkyl or heterocycloalkyl substituents comprising at least 3 ring atoms, at least one of which is a hetero atom, e.g. N, O or S, and which in the case of $C_4$–$C_{19}$ heteroaralkyl groups are attached via an alkylene moiety comprising at least 1 carbon atom. Also in the present description the term "heteroaryl" includes unsaturated cyclic moieties containing heteroatoms, including furyl, benzofuryl, thienyl and the like.

The novel oxazoles and imidazoles of the invention, in particular the compounds of formulae II, II', III and III' and the specific compounds listed above are hereinafter referred to "Agents of the Invention".

The Agents of the Invention which comprise free hydroxyl groups may also exist in the form of ester, e.g. pharmaceutically acceptable, physiologically cleavable esters, and as such are included within the scope of the invention. Such pharmaceutically acceptable esters are preferably prodrug ester derivatives, such being convertible by solvolysis or cleavage under physiological conditions to the corresponding Agents of the Invention which comprise free hydroxyl groups. Suitable pharmaceutically acceptable prodrug esters are those derived from a carboxylic acid, a carbonic acid monoester or a carbamic acid, advantageously esters derived from an optionally substituted lower alkanoic acid or an arylcarboxylic acid.

Agents of the Invention may also exist in the form of salts, e.g. pharmaceutically acceptable salts, and as such are included within the scope of the invention. Pharmaceutically acceptable salts include acid addition salts with conventional acids, for example, mineral acids, e.g., hydrochloric acid, sulfuric or phosphoric acid, or organic acids, for example, aliphatic or aromatic carboxylic or sulfonic acids, e.g., acetic, propionic, succinic, glycolic, lactic, malic, tartaric, citric, ascorbic, maleic, fumaric hydroxymaleic, pyruvic, pamoic, methanesulfonic, toluenesulfonic, naphthalenesulfonic, sulfanilic or cyclohexylsulfamic acid; also amino acids, such as arginine and lysine. For compounds of the invention having acidic groups, for example, a free carboxy group, pharmaceutically acceptable salts also represent metal or ammonium salts, such as alkali metal or alkaline earth metal salts, e.g., sodium, potassium, magnesium or calcium salts, as well as ammonium salts, which are formed with ammonia or suitable organic amines.

Agents of the Invention of formula II'

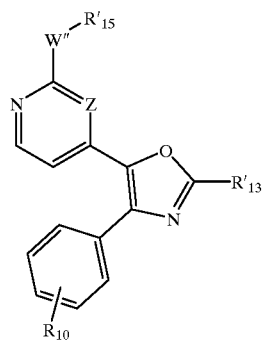

II'' wherein $R'_{13}$, $R'_{15}$, $R_{10}$ and Z are as previously defined and W'' is —NH—, may be prepared by reacting the corresponding precursor compound of formula IV or IV'

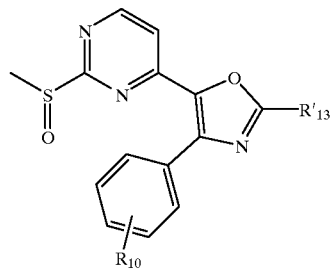

IV

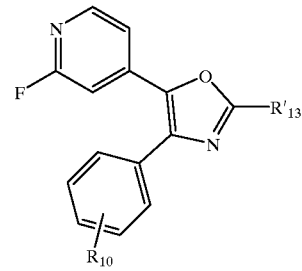

IV' wherein $R'_{13}$ and $R_{10}$ are as previously defined, with the corresponding $R'_{15}$—$NH_2$ derivative. For example, the reaction may be carried out by refluxing the reactants in an organic solvent, e.g. dichloroethane, e.g. in the presence of diethoxytrifluoroborane. Thereafter, if desired, the compound of Formula II'' obtained nay be converted into a further compound of Formula II'' or otherwise treated as required.

The precursor compound of formula IV may be prepared by controlled oxidation of the corresponding 5(2-methylthio-4-pyrimidyl)-4-phenylimidazole, e.g. employing an oxidising agent such as mCPBA (meta chloroperbenzoic acid), conveniently in an organic solvent such as methylene chloride. The corresponding 5(-4-pyrimidyl/pyridyl)-4-phenyloxazole compound may be prepared by contacting the corresponding acetophenone precursor compound of formula V or V'

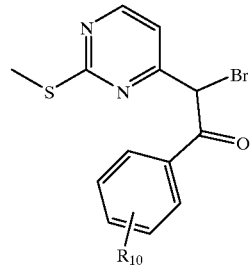

V

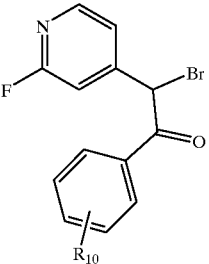

V' wherein $R_{10}$ is as defined above, with a corresponding amide of formula $R'_{13}C(O)NH_2$, typically at elevated temperature. The compounds of formula V and V' may be prepared by bromination of the corresponding acetophenone, e.g. 2-(2-methylthio-4-pyrimidyl)acetophenone. The acetophenone precursor may be prepared by reacting the corresponding N-methoxy-N-methylbenzamide with the corresponding pyrimidine, e.g. 4-methyl-2-(methylthio)pyrimidine, for instance in a THF containing organic solvent with cooling.

Thus in a further aspect the invention includes a process for the preparation of a compound of formula II"

II'

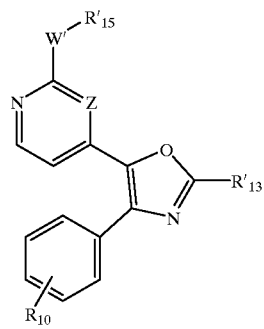

wherein $R'_{13}$, $R'_{15}$, $R_{10}$ and Z are as previously defined and W" is —NH—, which comprises reacting the corresponding precursor compound of formula IV or IV'

IV

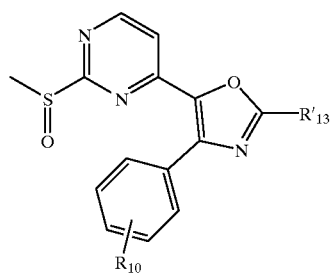

IV'

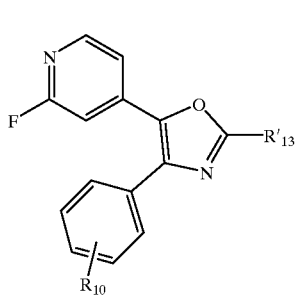

wherein $R'_{13}$, $R_{10}$ and Z are as previously defined, with the corresponding $R'_{15}$—$NH_2$ amine, and thereafter, if desired, converting the compound of formula II" obtained into a further compound of formula II" or a pharmaceutically-acceptable and -cleavable ester thereof or acid addition salt thereof.

Agents of the Invention of formula III"

III'

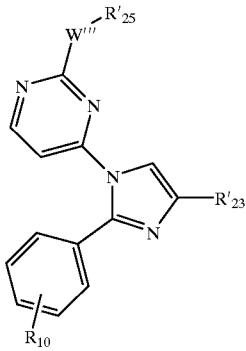

wherein $R'_{23}$, $R'_{25}$ and $R_{10}$ are as previously defined and W'" is —NH— or —O—, may be prepared by reacting the corresponding compound of formula I" in which $R'_{23}$ is halogen, e.g. Br, with the corresponding $R'_{23}$ ketone or activated $R'_{23}$ precursor, e.g. tri-alkylstannyl activated $R'_{23}$ precursor. For example, the reaction may be carried out, e.g. in the presence of reducing agent, such as BuLi or $PdCl_2(PPh_3)_2$, by refluxing the reactants, and/or with cooling, in an organic solvent, as appropriate. Thereafter, if desired, the compound of Formula III" obtained may be converted into a further compound of Formula III" or otherwise treated as required.

The compound of formula III" in which $R'_{23}$ is halogen, e.g. Br, may be prepared reacting the corresponding precursor compound of formula VI

VI

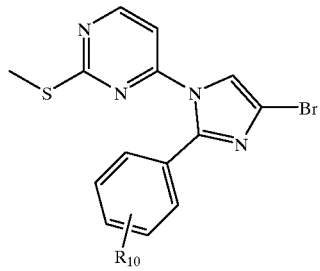

wherein $R_{10}$ is as previously defined with the corresponding $R'_{25}$—$NH_2$ or $R'_{25}$—OH derivative. For example, the reaction may be carried by refluxing the reactants in an organic solvent, e.g. dichloroethane, e.g. in the presence of diethoxytrifluoroborane.

The corresponding 1(2-methylthio-4-pyrimidyl)-2-phenyl-4-bromo-imidazole compound may be prepared by reacting the corresponding 2-phenyl-4-bromo-imidazole compound with 4-chloro-2-methylthiopyrimidine, e.g. in the presence of $KN(TMS)_2$ in an organic solvent such as DMF. The 2-phenyl-4-bromo-imidazole compound may be obtained by removal of the trimethylsilanyl-ethoxymethyl from the corresponding 1-trimethylsilanyl-ethoxymethyl-2-phenyl-4-bromo-imidazole compound, which in turn may be prepared from 4,5-dibromo compound, which in turn may be prepared by phenylation of the known compound, 2,4,5-tribromo-1-(2-trimethylsilanyl-ethoxymethyl)imidazole (Tetrahedron Letters (1998), 39(29),5171–5174); for instance as hereinafter described in the Examples.

Thus in a further aspect of the invention includes a process for the preparation of a compound of formula III"

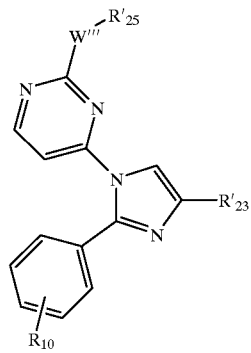

wherein R'$_{23}$, R'$_{25}$ and R$_{10}$ are as previously defined and W'" is —NH— or —O—, comprising reacting a corresponding compound of formula III" in which R'$_{23}$ is halogen, e.g. Br, with the corresponding R'$_{23}$ ketone or activated R'$_{23}$ precursor, e.g. tri-alkylstannyl activated R'$_{23}$ precursor, and thereafter, if desired, converting the compound of formula I" obtained into a further compound of formula III" or a pharmaceutically-acceptable and -cleavable ester thereof or acid addition salt thereof.

Alternative processes for preparation of Agents of the Invention are described in the Examples and are included within the scope of the present invention.

The synthesis of Agents of the Invention is further described in the following Examples.

EXAMPLES

Example 1

4-(4-Fluorophenyl)-5-(2-[1-(S)-phenylethyl]amino-4-pyrimidyl)-2-N-morpholinyloxazole a) 4-Fluoro-2-(2-methylthio-4-pyrimidyl)acetophenone

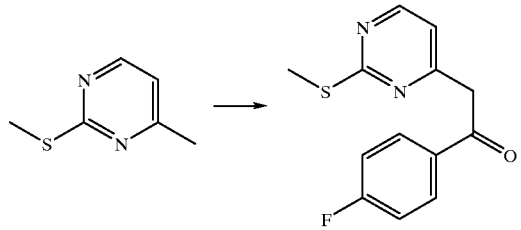

nBuLi (10 ml of a 1.6 M solution in hexane; 12 mmol) is added at −78° C. to a solution of diisopropylamine (2.48 ml; 17 mmol) in THF (15 ml) and stirred for 5 min. 4-Methyl-2-(methylthio)pyrimidine (2 g; 14.5 mmol) dissolved in THF (2 ml) is added dropwise and stirred for 30 mm at −78 C. 4-Fluoro-N-methoxy-N-methylbenzamide (2.66 g; 14.5 mmol) is dissolved in THF (3 ml) and added slowly to the reaction mixture. The mixture is warmed to r.t. within 45 min. and poured on water and extracted with ethyl acetate three times. The combined organic phases are dried over Na$_2$SO$_4$ and evaporated to dryness to yield 2.5 g (65%) of yellow crystals after recrystallisation from tert.butyl methyl ether/hexane.

1H-NMR (200 MHz CDCl$_3$): 3.00 (s, 3H): 6.30 (s, 1H); vinyl-H of enol); 7.00 (d, 1); 7.50 (dd, 2H); 8.20 (dd, 2H); 8.7 (d, 2H). Due to pH-dependent keto-enol tautomerism, signals may be duplicated.

b) 4-Fluoro-2-bromo-2-(2-methylthio-4-pyrimidyl) acetophenone

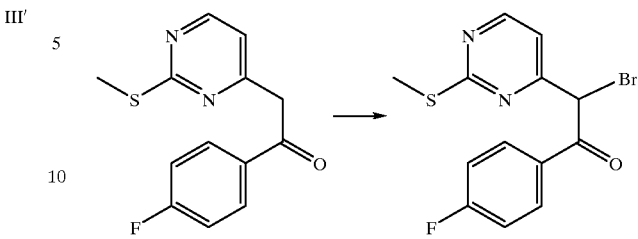

Bromine (1.22 g, 7.6 mmol) in acetic acid (5.6 ml) is added to a solution of 4-Fluoro-2-(2-methylthio-4-pyrimidyl)acetophenone (2 g; 7.6 mmol) in acetic acid (40 ml. The initially thick precipitate is almost dissolved after 20 min, filtered and the filtrate evaporated to dryness. The residue is taken up in a saturated solution of NaHCO$_3$ and extracted three times with tert.butyl methyl ether. The combined organic phases are dried over Na$_2$SO$_4$ and evaporated to dryness to yield 2.6 g (100%) of a brown oil, which is used in the next step without purification.

c) 4-(4-Fluorophenyl)-5-([2-methylthio]-4-pyrimidyl)-2-N-morpholinyloxazole

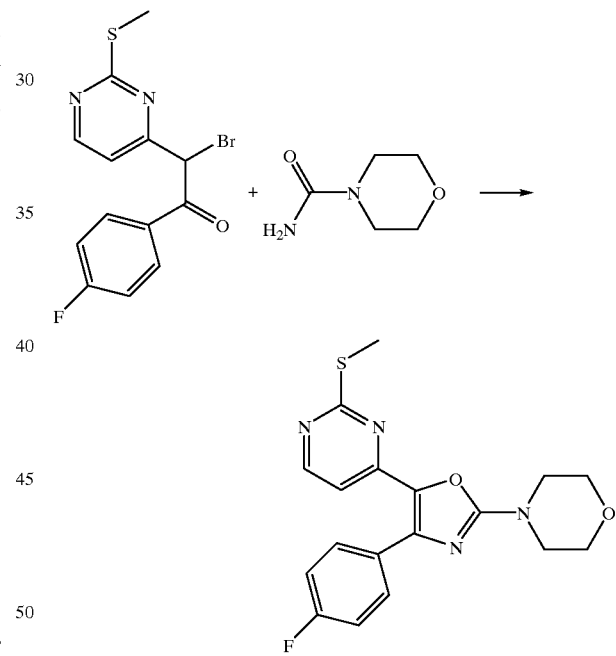

4-Fluoro-2-bromo-2-(2-methylthio-4-pyrimidyl) acetophenone (682 mg; 2 mmol) and morpholine-4-carboxylic acid amide (J. Org. Chem. 1987, 52, 3426.) (3.9 g; 30 mmol) are mixed and heated at 150 C as a melt for 4 min. The reaction mixture is partitioned between methylene chloride and 2N Na$_2$CO$_3$. The aqueous layer is extracted twice with methylene chloride. The combined organic phases are washed with water, dried over Na$_2$SO$_4$, flitered and evaporated to dryness to give a solid, which is purified by recrystallisation from acetone/hexane to yield the title compound as colorless crystals (140 mg; 19%).

1H-NMR (400 MHz; CDCl$_3$): 3.60 (dd, 4H); 3.78 (dd, 4H); 6.92 (d, 1H); 7.02 (dd, 2H); 7.90 (dd, 2H); 8.32 (d, 1H). MS (m/z) EI: 372 (M+, 100).

d) 4-(4-Fluorophenyl)-5-([2-methylsulfinyl]-4-pyrimidyl)-2-N-morpholinyloxazole

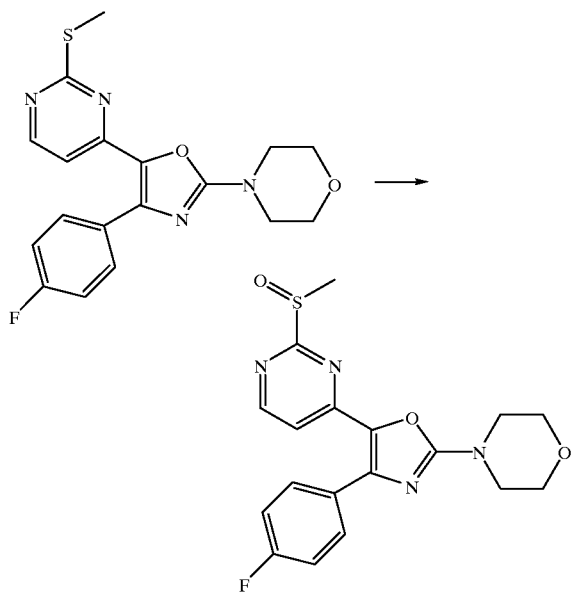

4-(4-Fluorophenyl)-5([2-methylthio]-4-pyrimidyl)-2-N-morpholinyloxazole (135 mg 0.365 mmol) is dissolved in methylene chloride, cooled to 0 C and treated with mCPBA (100 mg; 0.49 mmol) for 15 min. The reaction mixture is poured on saturated Na$_2$CO$_3$ solution and extracted with ethyl acetate three times. The combined organic phases are dried over Na$_2$SO$_4$, filtered and evaporated to dryness yielding the title compound as a yellow foam (140 mg; 95%) which is used for the next step without further purification.
e) 4-(4-Fluorophenyl)-5-(2-[1-(S) -phenylethyl]amino-4-pyrimidyl)-2-N-morpholinyloxazole

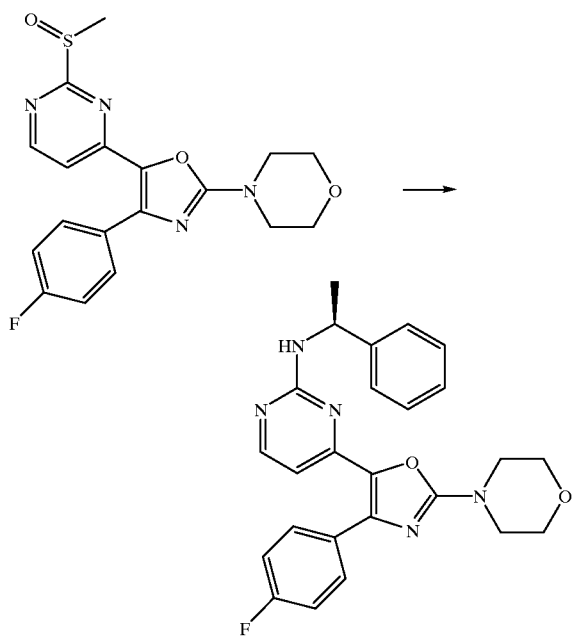

4-(4-Fluorophenyl)-5-([2-methylsulfinyl]-4-pyrimidyl)-2-N-morpholinyloxazole (140 mg; 0.36 mmol) and 1-(S)-phenylethylamine (0.7 ml) are heated at 120 C for 2 h. After evaporation of the amine, the product is purified by preparative HPLC on LiChrospher RP-18 (Gibson HPLC-system; column tube: 125 mm×25 mm ID) with MeCN/water as elution system, 40:60 to 100:0 as gradient and a flow rate of 10 ml/min the title product as colorless foam (75 mg; 44%).

1H-NMR (400 MHz; DMSO-d6): mixture of rotamers. 1.41 (bd, 3H); 3.50–3.60 (bs, 4H); 3.68–3.76 (bs, 4H); 4.81–5.10 (bs, 1H); 6.71 (d, 1H); 7.00–7.30 (m, 7H); 7.58 (bs, 1H, NH); 7.93–8.16 (bs, 2H); 8.23 (d, 1H).

MS (m/z) EI: 445 (M+, 100); 430 (50); 359 (10).

Example 2

4-(4-Fluorophenyl)-5-(2-[1-(S)-phenylethyl]amino-4-pyrimidyl)-2-N-piperidinyloxazole
a) 4-(4-Fluorophenyl)-5-([2-methylthio]-4-pyrimidyl)-2-N-piperidinyloxazole

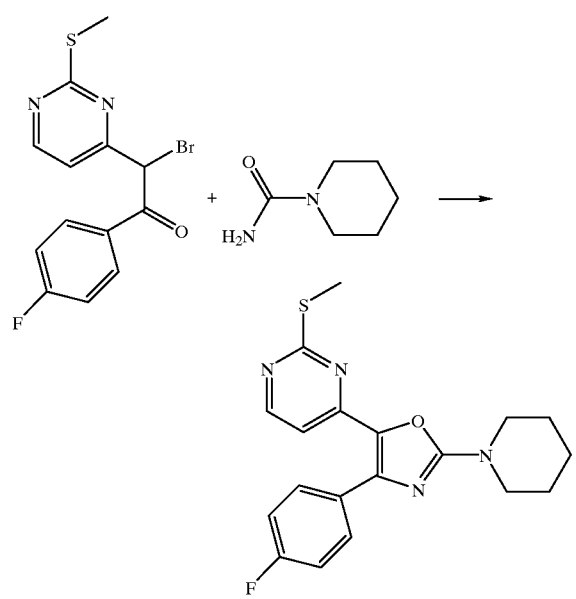

4-Fluoro-2-bromo-2-(2-methylthio-4-pyrimidyl) acetophenone (682 mg; 2 mmol) and piperidine-N-carboxylic acid amide (Pharmazie 1989, 44, 225.) (3.9 g; 30 mmol) are mixed and heated at 155 C as a melt for 5 min. The reaction mixture is partitioned between methylene chloride and 2N Na$_2$CO$_3$. The aqueous layer is extracted twice with methylene chloride. The combined organic phases are washed with water, dried over Na$_2$SO$_4$, filtered and evaporated to dryness to give a solid, which is purified by recrystallistion from TBME to yield the title compound as colorless crystals (210 mg, 28%).

MS (m/z) EI: 370 (M+, 100).

b) 4-(4-Fluorophenyl)-5-(2-[1-(S)-phenylethyl]amino-4-pyrimidyl)-2-N-piperidinyloxazole

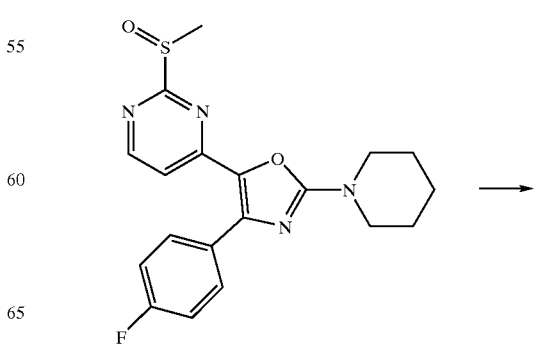

-continued

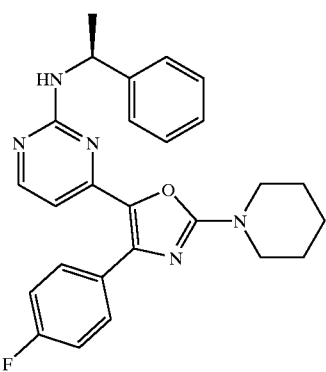

4-(4-Fluorophenyl)-5-([2-methysulfinyl]-4-pyrimidyl)-2-N-piperidinyloxazole (prepared in analogy to intermediate 1b) (220 mg; 0.566 mmol) and 1-(S)-phenylethylamine (0.9 ml) are heated at 120 C for 1 h. After evaporation of the amine, the product is purified by SiO2 chromatography (acetone/cyclohexylamine 5/95) to yield the title compound as yellow crystals (135 mg 56%).

1H-NMR (400 MHz; DMSO-d6): mixture of rotamers. 1.41 (d, 3H); 1.60 (s, 6H); 3.55 (s, 4H); 4.83–5.05 (bs, 1H); 6.65 (d, 1H); 7.03–7.31 (m, 7H); 7.53 (bs, 1H, NH); 7.92–8.15 (bs, 2H); 8.23 (d, 1H).

MS (m/z) EI: 443 (M+); 428 (40).

The following compounds of Examples 3 to 7 are prepared analogously to the compounds of Examples 1 and 2:

| Example | Compound | NMR | MS |
|---|---|---|---|
| 3 | | 1H-NMR(400 MHz; DMSO-d6): mixture of rotamers. 1.21(t, 3H); 1.41(bd, 3H); 3.55(bd, 4H); 3.60(bd, 4H); 4.09 (q, 2H); 4.82–5.05(bs, 1H); 6.70(d, 1H); 7.02–7.31(m, 7H); 7.58(bs, 1H, NH); 7.93–8.15(bs, 2H); 8.37(d, 1H). | MS (e/z) EI: 457(M+, 60); 442(10); 401(10); 387(100); 105(20). |
| 4 | | 1H-NMR(400 MHz; DMSO-d6, 120 C): 1.47 (d, 3H); 1.82–1.96(m, 2H); 2.01–2.20(m, 4H); 2.25(s, 3H); 2.75–2.95 (m, 3H); 5.02–5.11(m, 1H); 6.81(d, 1H); 7.06(s, 1H, NH); 7.18(dd, 2H); 7.23–7.30(m, 5H); 8.02 (dd, 2H); 8.32(d, 1H). | MS(e/z) EI: 457(M+, 60); 442(10); 401(10); 387(100); 105(20). |
| 5 | | 1H-NMR(400 MHz; DMSO-d6): mixture of rotamers. 1.05(t, 3H); 1.42(bd, 3H); 2.40(q, 4H); 2.49(bt, 4H); 3.58 (bt, 4H); 4.82–5.07(bs, 1H); 6.70(d, 1H); 6.90–7.42(m, 7H); 7.90–8.10 (m, 3H); 8.73(d, 1H). | MS(e/z) EI: 472(M+, 95); 457(25); 401(30); 388(100); 375(60); 360 (30); 105(60). |

| Example | Compound | NMR | MS |
|---------|----------|-----|-----|
| 6 | 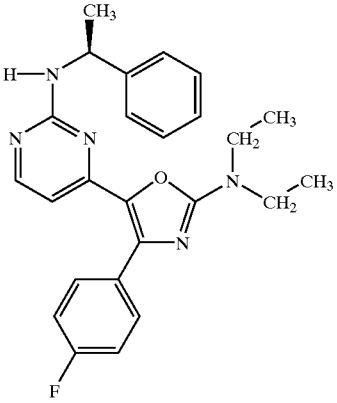 | 1H-NMR(400 MHz; DMSO-d6): mixture of rotamers. 1.20(t, 6H); 1.42(d, 3H); 3.53(q, 4H); 4.83–5.03(bs, 1H); 6.65 (d, 1H); 7.05–7.45(m, 7H); 7.53(bs, 1H); 7.92–8.13(m, 2H); 8.23(d, 1H) | MS(e/z) EI: 431(M+, 100); 416(50); 359(10); 120(50); 105(40)95 (20). |
| 7 | 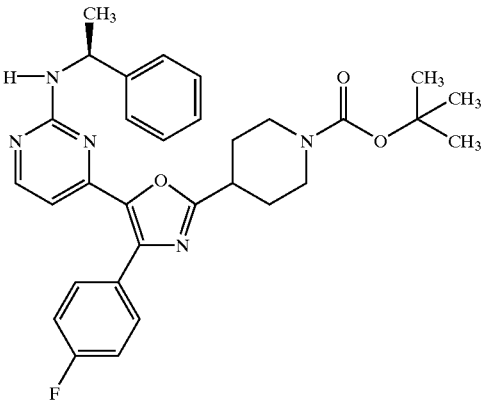 | 1H-NMR(400 MHz; CDCl₃): 1.43(s, 9H); 1.53 (bs, 3H); 1.80(bq, 2H); 2.05(bd, 2H); 2.82–3.05 (m, 3H); 4.00–4.16(m, 2H); 5.00(bs, 1H); 6.71 (d, 1H): 6.98(bt, 2H): 7.11–7.28(m, 5H); 7.83 (dd, 2H); 8.21(d, 1H). | MS(e/z) EI: 543(M+, 30); 442(50); 387(90); 105(60). |

Example 8

4-(4-Fluorophenyl)-5-(2-[1-(S)-phenylethyl]amino-4-pyrimidyl)-2-(4-NH-piperidine-1-yl)oxazole

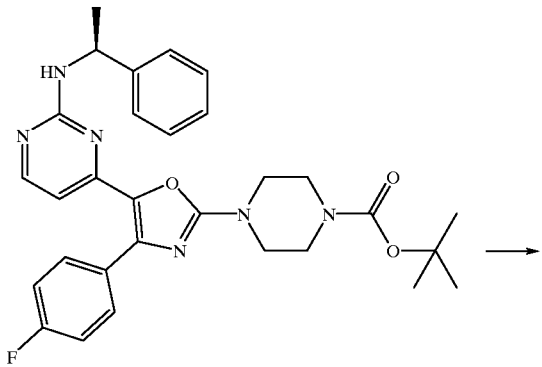

→

-continued

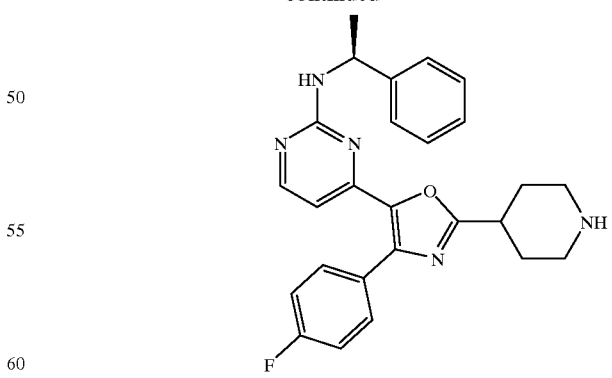

4-(4-Fluorophenyl)-5-(2-[1-(S)-phenylethyl]amino-4-pyrimidyl)-2-(4-tert.butyloxycarbonylpiperidine-1-yl) oxazole (650 mg; 1.19 mmol, the product of Example 7 above) is stirred in EtOH/HCl conc (1:1; 24 ml) for 30 min, then poured on a saturated solution of Na₂CO₃ and extracted with ethyl acetate three times. The combined organic phases are washed with water, dried over Na₂SO₄, filtered and evaporated to dryness to give a solid, which is purified by recrystallisation from TBME to yield the HCl-salt of the title compound as colorless crystals (180 mg; 33%)

1H-NMR (400 MHz; DMSO-d6) of HCl salt; mixture of rotamers: 1.42 (bs, 3H); 1.93–2.08 (m, 2H); 2.19–2.31 (m, 2H); 2.98–3.11 (m, 2H); 3.28–3.48 (m, 3H); 4.75–5.25 (bs, 1H); 6.82 (bs, 1H); 6.98–7.43 (m, 7H); 7.82 (d, 1H); 7.90–8.22 (m, 2H); 8.38 (bs, 1H); 8.95 (bs, NH2)

MS (e/z) EI: 443 (M+); 387(80); 103 (100).

Example 9

4-(4-Fluorophenyl)-5-(2-cyclopropylmethylamino-4-pyrimidyl)-2-(4-NH-piperidin-1-yl)oxazole

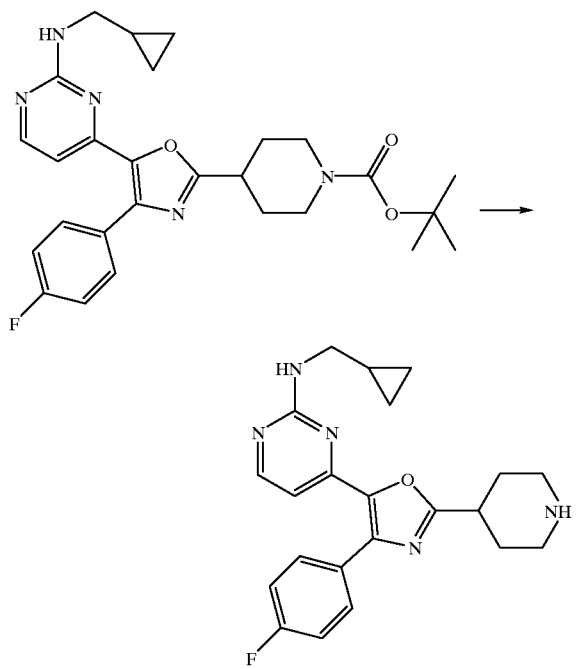

4-(4-Fluorophenyl)-5-(2-cyclopropylmethylamino-4-pyrimidyl-2-(4-tert.butyloxycarbonylpiperidine-1-yl) oxazole (prepared in analogy to example 7) (1.12 g; 2.27 mmol) is dissolved in 0° C. in CH₂Cl₂/CF₃COOH (8 ml; 1:1) and stirred for 10 min. at 10–15° C. The reaction mixture is poured on cold 2N NaOH; the precipitated solid is filtered and recrystallised from EtOH/Hexane to yield the title compound (775 mg; 87%) as colorless crystals.

1H-NMR (400 MHz; CDCl₃): 0.20 (bs, 2H); 0.53 (bd, 2H); 1.03 (bs, 1H); 1.82–1.98 (m, 2H); 2.15 (bd, 2H); 2.80 (t, 2H); 3.02–3.12 (m 1H); 3.12–3.30 (m, 4H); 5.24 (bs, 1H, NH); 6.86 (d, 1H); 7.12 (t, 2H); 8.05 (s, 2H); 8.32 (d, 1H).

MS (e/z) Cm/ES–: 392.1 (M–H, 100). MS (e/z) Cm/ES+: 394.0 (MH+, 100).

Example 10

4-(4-Fluorophenyl)-5-(2-[1-(S)-phenylethyl]amino-4-pyrimidyl)-2-(4-N-acetyl-piperidine-1-yl)oxazole

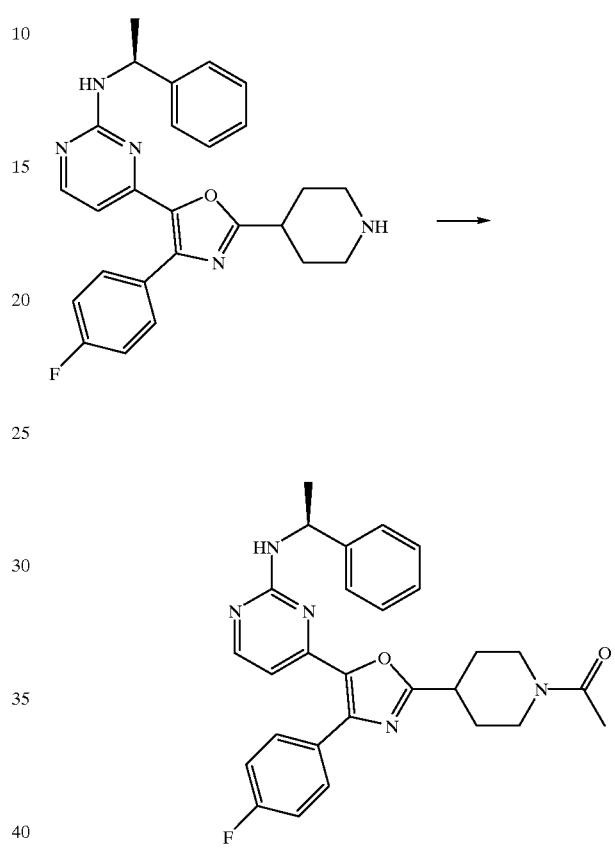

4-(4-Fluorophenyl)-5-(2-[1-(S)-phenylethyl]amino-4-pyrimidyl)-2-(4-NH-piperidine-1-yl)oxazole (44.4 mg; 0.1 mmol) is dissolved in THF/pyridine (1.0 ml/0.5 ml) and treated with acetyl chloride (0.007 ml; 0.1 mmol) for 1 h at room temperature. The reaction mixture is evaporated and partitioned between ethyl acetate and 2 N Na₂CO₃. The aqueous phase is extracted three times with ethyl acetate. The combined organic phases are washed with water, dried over Na₂SO₄, filtered and evaporated to dryness to give a foam, which is purified by SiO₂ chromatography (acetone/hexane 10/90 to 25/75) to yield the title compound (40 mg, 90%).

1H-NMR (400 MHz; DMSO-d6, 120 C): 1.48 (d, 3H); 1.71–1.97 (m, 2H); 2.04 (s, 3H); 2.07–2.15 (m, 2H); 3.05–3.21 (bs, 2H); 3.21–3.30 (m, 1H); 3.95–4.15 (bs, 2H); 5.03–5.11 (m, 1H); 6.82 (d, 1H); 7.10 (d, 1H, NH); 7.18 (dd, 2H); 7.23–7.30 (m, 5H); 8.03 (dd, 2H); 8.35 (d, 1H).

MS (e/z) EI: 485 (M+); 470 (60); 442 (20); 387 (80); 105 (55).

Example 11

4-(4-Fluorophenyl)-5-(2-[1-(S)-phenylethyl]amino-4-pyrimidyl)-2-(4-pyridyl)oxazole

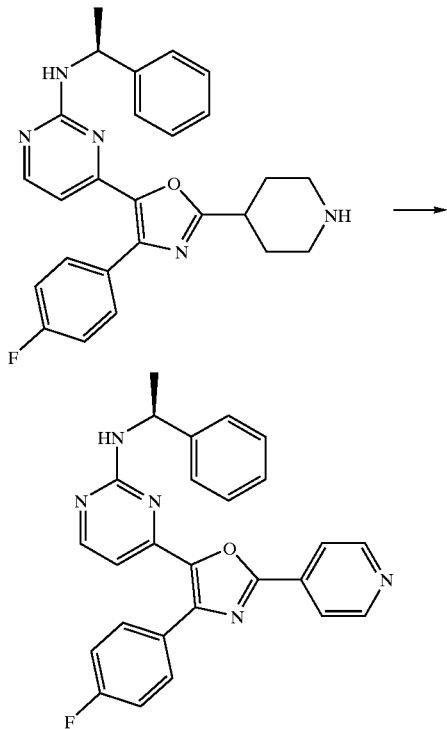

4-(4-Fluorophenyl)-5-(2-[1-(S)-phenylethyl]amino-4-pyrimidyl)-2-(4-NH-piperidine-1-yl)oxazole (44.4 mg; 0.1 mmol) is dissolved in xylenes (5 ml) and treated with 10% Pd/C (20 mg) at 125 C while blowing air through the reaction mixture for 12 h. The mixture is filtered, evaporated to dryness and purified by $SiO_2$ chromatography (acetone/cyclohexane 20/80) to yield the title compound as a yellow foam (10 mg; 23%).

MS (e/z) EI: 437 (M+; 50); 422 (60).

Example 12

4-(4-Fluoropheny1-5-(2-[1-(S)-phenylethyl]amino-4-pyrimidyl)-2-(1-piperazinyl)oxazole

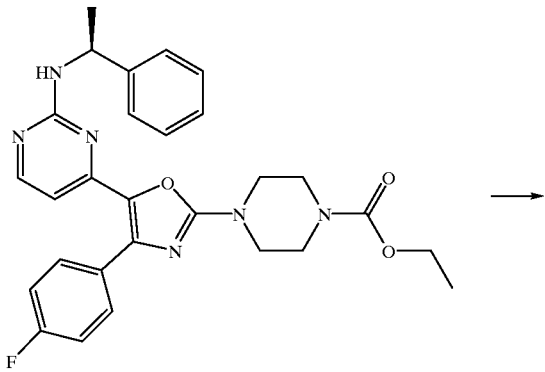

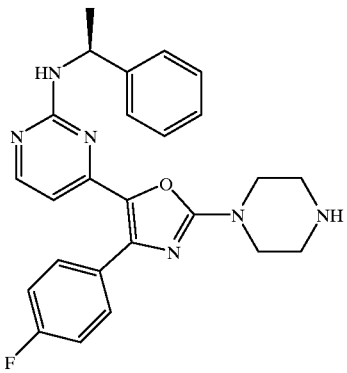

4-(4-Fluorophenyl)-5-(2-[1-(S)-phenylethyl]amino-4-pyrimidyl)-2-(4-ethoxy-carbonylpiperazin-1-yl)oxazole (130 mg; 0.251 mmol in $CHCl_3$ (2.6 ml) is treated with trimethylsilyl iodide (0.113 ml; 0.83 mmol) at 60 C. After 3 h a second portion of trimethylsilyl iodide (0.113 ml; 0.83 mmol) is added and the reaction heated at 60 C for 21 h. 6 M HCl in 1-propanol (3 ml) is added to the reaction mixture, stirred until dissolution is complete and then poured on a saturated solution of $Na_2CO_3$.

The aqueous phase is extracted three times with ethyl acetate. The combined organic phases are washed with water, dried over $Na_2SO_4$, filtered and evaporated to dryness to give a foam, which was purified by $SiO_2$ chromatography (TBME/MeOH/$NH_3$ conc 90/9/1 to 85/15/1.5) to yield the title compound as a yellow foam (80 mg; 72%).

1H-NMR (400 MHz; DMSO-d6). Mixture of rotamers: 1.40 (d, 3H); 2.79–2.83 (m, 4H); 3.52 (m, 4H); 4.80–5.05 (bs, 1H); 6.67 (d, 1H); 7.03–7.33 (m, 7H); 7.53 (bs, 1H, NH); 7.91–8.15 (bs, 2H); 8.23 (d, 1H).

MS (e/z) EI: 445 (MH+, 75).

Example 13

4-(4-Fluorophenyl)-5-(2-[1-(S)-phenylethyl]amino-4-pyrimidyl)-2-(1-amino-1-methyl)ethyloxazole a) 4-(4-Fluorophenyl)-5-(2-methylthio-4-pyrimidyl)-2-(1-N-benzyloxy-carbonyl)amino-1-methyl)ethyloxazole

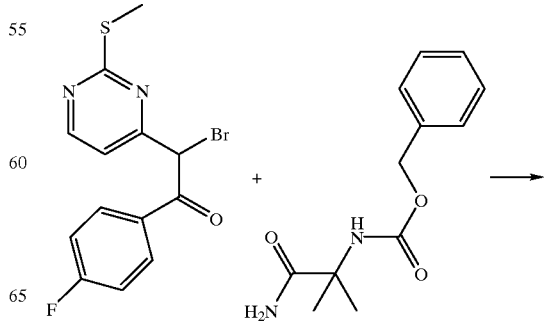

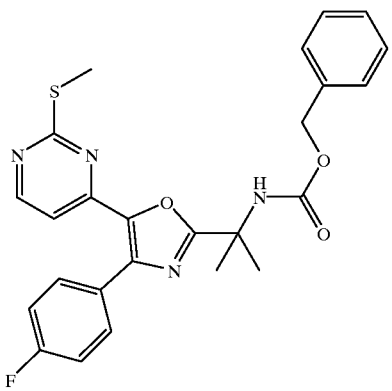

4-Fluoro-2-bromo-2-(2-methylthio-4-pyrimidyl) acetophenone (2.39 g; 7 mmol) and N-carbobenzyloxy-2-methyl-alanine amide (14 g, 41 mmol) are refluxed in xylenes (35 ml) for 7 h. The reaction mixture is evaporated and purified via SiO$_2$ chromatography (acetone/cyclohexane 10/90) to yield the title compound (900 mg, 27%).

b) 4-(4-Fluorophenyl)-5-(2-methylsulfinyl-4-pyrimidyl)-2-(1-N-benzyloxy-carbonyl)amino-1-methyl)ethyloxazole

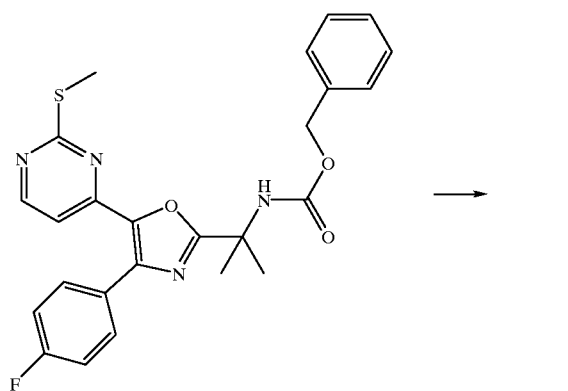

4-(4-Fluorophenyl)-5-(2-methylthio-4-pyrimidyl)-2-(1-N-benzyloxy-carbonyl)amino-1-methyl)ethyloxazole (960 mg, 2 mmol) is dissolved in methylene chloride (20 ml), cooled to 0 C and treated with mCPBA (490 mg; 2 mmol 70%) for 30 min at 0 C. The reaction mixture is poured on 2 N Na$_2$CO$_3$ and extracted with ethyl acetate 3 times. The combined organic phases are washed with water, dried over Na$_2$SO$_4$, filtered and evaporated to dryness to give a foam, which is used for the next step without further purification.

c) 4-(4-Fluorophenyl)-5-(2-cyclopropylmethylamino-4-pyrimidyl)-2-(1-N-benzyloxycarbonyl)amino-1-methyl)ethyloxazole

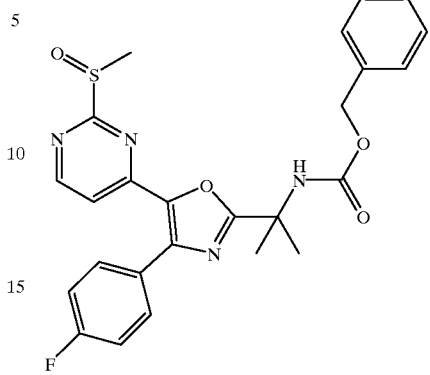

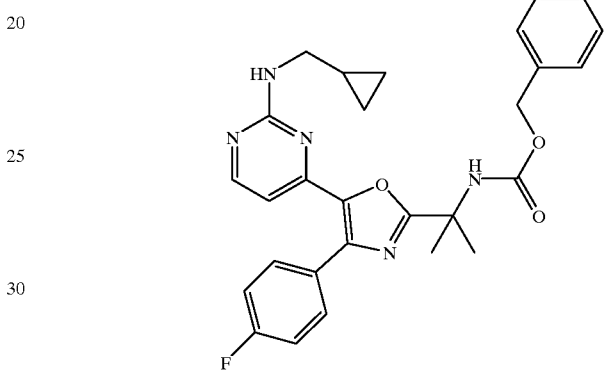

4-(4-(Fluorophenyl)-5-(2-methylsulfinyl-4-pyrimidyl)-2-(1-N-benzyloxy-carbonyl)amino-1-methyl)ethyloxazole (900 mg; 1.8 mmol) and cyclopropylmethylamine (2 ml) are refluxed for 1 h. The reaction mixture is evaporated and purified via SiO$_2$ chromatography (acetone/cyclohexane 10/90 to 20/80) yielding the title compound as a yellow foam (670 mg; 73%).

1H-NMR (400 MHz; DMSO-d6): Mixture of rotamers: 0.03–0.18 (bs, 2H); 0.31–41 (bs, 2H); 0.87–1.01 (bs, 1H); 1.68 (s, 6H); 2.94–3.09 (m, 2H); 5.03 (s, 2H); 6.70 (d, 1H); 7.20–7.40 (m, 8H); 8.04–8.22 (bs, 3H); 8.34 (d, 1H).

MS (e/z) EI: 501 (M+, 20); 410 (20); 309 (50); 91 (100).

d) 4-(4-Fluorophenyl)-5-(2-[1-(S)-phenylethyl]amino-4-pyrimidyl)-2-(1-amino-1-methyl)ethyloxazole

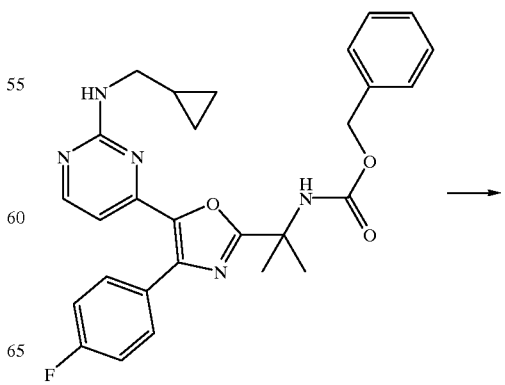

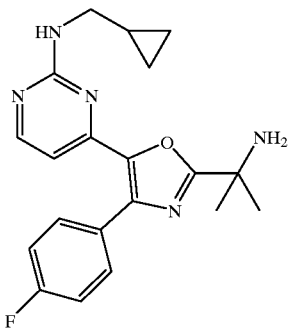

4-(4-Fluorophenyl)-5-(2-cyclopropylmethylamino-4-pyrimidyl)-2-(1-(N-benzyloxycarbonyl)amino-1-methyl)ethyloxazole (620 mg; 1.25 mmol) is dissolved in EtOH (100 ml) and hydrogenated at 1 atm over 10% Pd/C (1.3 g). Hydrogen uptake is complete after 1 h. Pd/C is filtered off, the solvent evaporated and the resulting product purified via SiO$_2$ chromatography (ethyl acetate/EtOH/NH$_3$ conc 95/4.5/0.5 to 80/18/2) to yield the title compound (260 mg, 57%)

1H-NMR (400 MHz; DMSO-d6): Mixture of rotamers: 0.03–0.13 (bs, 2H); 0.31–0.41 (bs, 2H); 0.86–1.03 (bs, 1H); 1.51 (s, 6H); 2.30 (bs, 2H, NH2); 3.03 (bs, 2H); 6.93 (d, 1H); 7.27 (dd, 2H); 7.33 (bt, 1H, NH); 8.08–8.16 (bs, 2H); 8.47 (d, 1H).

MS (e/z) ESI: 368.2 (MH+, 100).

Example 14

4-(4-Fluorophenyl)-5-(2-[1-(S)-phenylethyl]amino-4-pyrimidyl)-2-(1-hydroxy-4-methylpiperidine-1-yl)oxazole a) 4-Fluoro-2-(2-fluoropyridin-4-yl)acetophenone

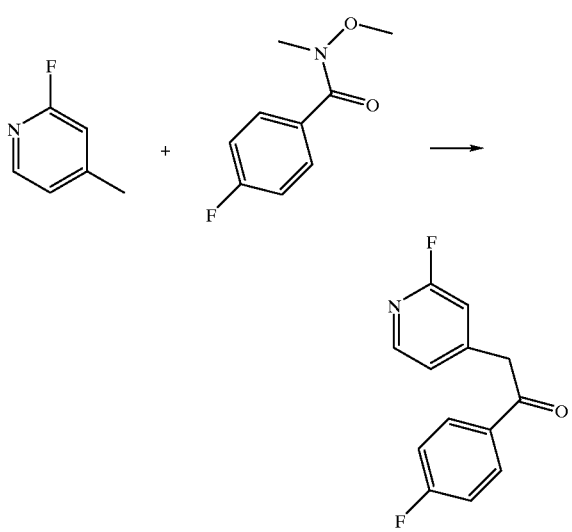

Diisopropylamine (0.93 ml; 6.55 mmol) in THF (6 ml) is cooled to −78 C and treated with nBuLi (3.8 ml; 6.08 mmol of a 1.6 M solution hexane). 2-Fluoro-4-methylpyridine (620 mg, 5.4 mmol) is added dropwise and stirred under argon for 30 min. 4-Fluoro-N-methoxy-N-methylbenzamide (1 g, 5.46 mmol) is added dropwise in THF (0.5 ml) and the reaction mixture allowed to warm up to room temperature within 10 min. then poured on a saturated solution of NaCl and extracted with TBME three times. The combined organic phases are washed with water, dried over Na$_2$SO$_4$, filtered and evaporated to dryness to yield the title compound as pale yellow crystals. Purification by recrystallisation from hot TBME rendered the desired compound as white solid (630 mg; 50%).

1H-NMR (200 MHz; CDCl$_3$): 4.35 (s, 2H); 6.88 (s, 1H); 7.08–7.30 (m, 3H); 7.99–8.15 (dd, 2H); 8.20 (d, 1H).

MS (e/z) ESI: 233 (M+, 5); 123 (100).

b) 4-Fluoro-2-bromo-(2-fluoropyridin-4-yl)acetophenone

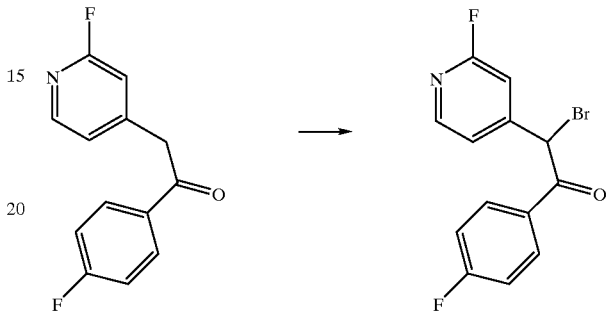

4-Fluoro-2-(2-fluoropyridin-4-yl)acetophenone (0.5 g; 2.1 mmol) dissolved in acetic acid (4 ml) is treated with bromine (0.34 g; 2.1 mmol) in acetic acid (1 ml) at room temperature for 2.5 h under stirring. The light brown solution is evaporated to dryness, dissolved in ether and extracted three times with diethyl ether. The combined organic phases are washed with a saturated solution of NaHCO$_3$, dried over Na$_2$SO$_4$, filtered and evaporated to dryness to yield the title compound as pale yellow oil (0.67 g; 100%).

1H-NMR (200 MHz; CDCl$_3$): 6.15 (s, 1H); 7.10–7.38 (m, 4H); 8.08 (dd, 2H); 8.23 (d, 1H).

MS (e/z) ESI: 232 (M-Br); 204 (10); 203 (12); 123 (100).

c) 4-(4-Fluorophenyl)-5-(2-fluoropyridin-4-yl)oxazole

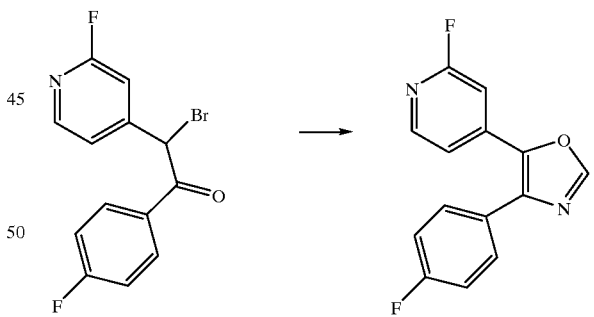

4-Fluoro-2-bromo-(2-fluoropyridin-4-yl)-acetophenone (6 g; 19.23 mmol) is dissolved in formamide (100 ml, treated with H$_2$SO$_4$conc (60 drops) and heated to 145 C for 6 min and 125 C for 15 min. The reaction mixture is poured on 2 N Na$_2$CO$_3$ and extracted with TBME 3 times. The combined organic phases are washed with water, dried over Na2SO4, filtered and evaporated to dryness and purified via SiO$_2$ chromatography (acetone/hexane 1/9) to yield the title compound as a white solid (1.92 g; 39%).

1H-NMR (400 MHz; DMSO-d6): 7.29 (s, 1H); 7.48 (t, 2H); 7.45 (d, 1H); 7.69 (dd, 2H); 8.32 (d, 1H); 8.74 (s, 1H).

MS (e/z) EI: 258 (M+, 100); 230 (20); 202 (40).

d): 4-(4-Fluorophenyl)-5-(2-[1-(S)-phenylethyl] aminopyridin-4-yl)oxazole

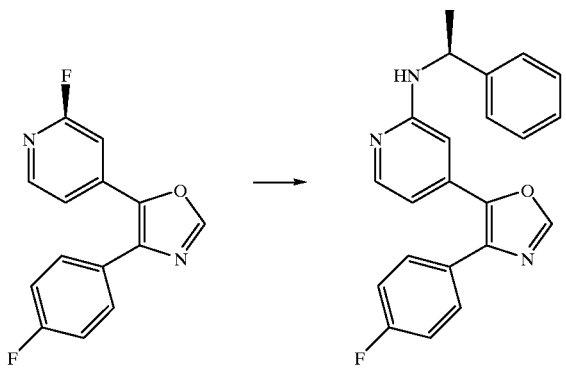

4-4-(Fluorophenyl)-5-(2-fluoropyridin-4-yl)oxazole (50 mg; 0.19 mmol) and S-(1)-phenylethylamine (0.5 ml) is heated to 180 C for 1.5 h, evaporated and purified via SiO₂ chromatography to yield the title compound as a colorless foam (34 mg; 50%).

1H-NMR (400 MHz; DMSO-d6): 1.40 (d, 3H); 4.96 (bt, 1H); 6.53 (d, 1H); 6.68 (s, 1H); 7.11–7.40 (m, 8H); 7.63 (dd, 2H); 7.95 (d, 1H); 8.06 (s, 1H).

MS (e/z) EI: 359 (M+, 100); 344 (90); 272 (40); 120 (40); 105 (50).

e) 4-(4-Fluorophenyl)-S-(2-[1-(S)-phenylethyl]amino-4-pyrimidyl)-2-(1-hydroxy-4-methylpiperidine-1-yl)oxazole

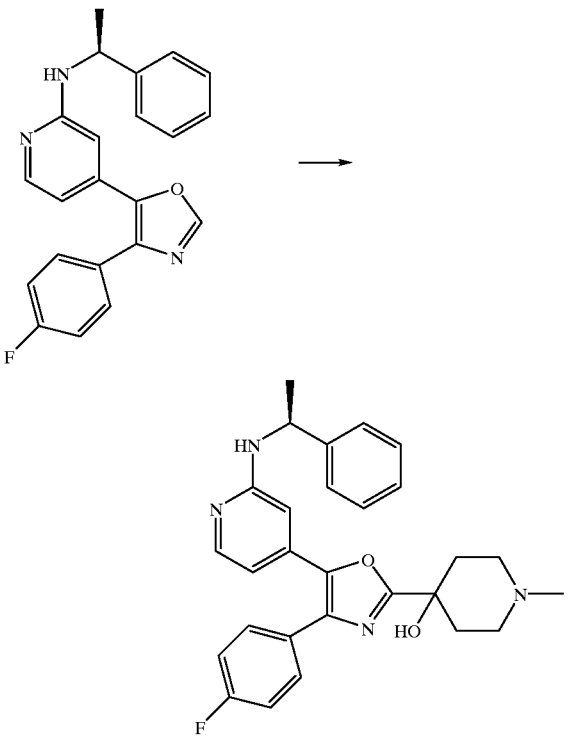

4-(4-Fluorophenyl)-5-(2-[1-(S)-phenylethyl] aminopyridin-4-yl)oxazole (100 mg; 0.278 mmol) is dissolved in THF (1.4 ml and cooled to −40 C. nBuLi (0.48 ml; 0.8 mmol of a 1.6 M solution in hexane) is added at −40 C dropwise while stirring under argon. After 10 min N-methyl-4-piperidone (0.09 ml; 0.75 mmol) is added and stirring continued for 10 min. The reaction mixture is poured on a saturated solution of NaCl and extracted with TBME 3 times. The combined organic phases are washed with water, dried over Na₂SO₄, filtered and evaporated to dryness and purified via SiO₂ chromatography (TBME/MeOH/NH₃conc 100/0/0 to 80/20/1) to yield the title compound as a slightly yellow foam (26 mg; 20%).

1H-NMR (400 MHz; DMSO-d6) mixture of rotamers: 1.20–1.33 (m, 2H); 1.40 (d, 3H); 1.97–1.98 (bd, 2H); 2.12 (s, 0.9H); 2.17 (s, 2.1H); 2.30–2.53 (m, 4H); 4.91–5.03 (m, 1H); 5.67 (s, 1H, OH); 6.50 (d, 1H); 6.69 (s, 1H); 7.10–7.42 (m, 8H); 7.61 (dd, 2H); 7.93 (d, 1H).

MS (e/z) EI: 472 (M+, 25); 454 (20; 71 (100).

Example 15

4-(4-Fluorophenyl)-2-(1-hydroxy-4-methyl) piperidine-1-yl)-5-(2-[cyclopropylmethyl]amino-4-pyridyl)oxazole a) 4-(4-Fluorophenyl)-2-(1-hydroxy-4-methyl)piperidine-1-yl)-5-(2-fluoro-4-pyridyl)oxazole

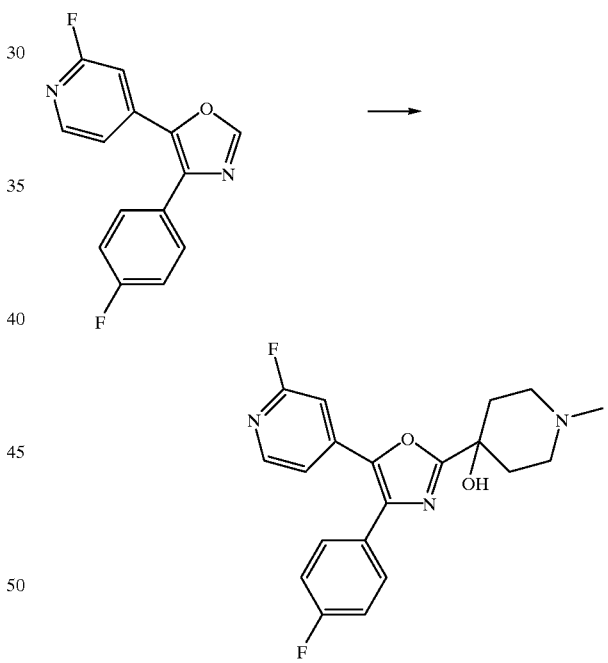

4-(4-Fluorophenyl)-5-(2-fluoropyridin-4-yl)oxazole (100 mg, 0.38 mmol) is dissolved in THF (1.4 ml), cooled under argon and stirring to −40 C and with nBuLi (0.242 ml; 0.387 mmol of a 1.6 M solution in hexane) for 5 min. N-methyl-4-piperidone is then added and the reaction stirred for another 5 min at −40 C., poured on a saturated solution of NaCl and extracted TBME 3 times. The combined organic phases are washed with water, dried over Na2SO4, filtered and evaporated to dryness and purified via SiO₂ chromatography (TBME/MeOH/NH₃conc 95/5/0.5 to 90/10/1) to yield the title compound as colorless crystals (95 mg, 67%).

MS (e/z) EI: 371 (M+, 20); 354 (10), 301 (20).

b) 4-(4-Fluorophenyl)-2-(1-hydroxy-4-methyl)piperidine-1-yl)-5-(2-[cyclopropylmethyl]amino-4-pyridyl)oxazole

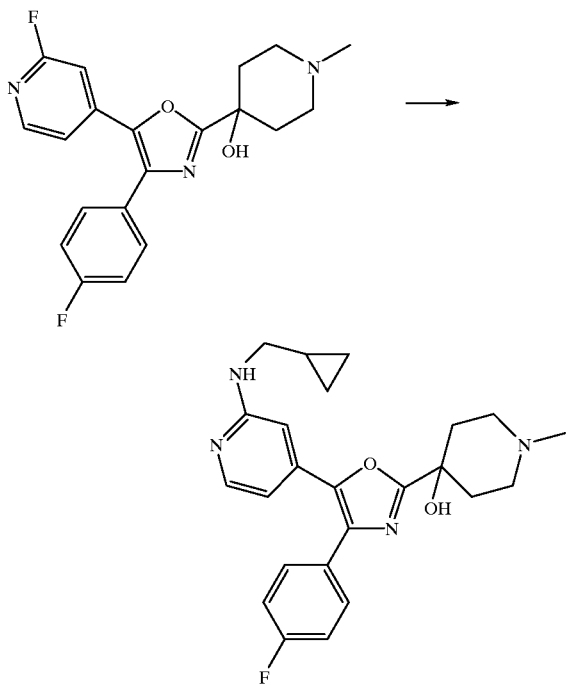

4-(4-Fluorophenyl)-2-(1-hydroxy-4-methyl)piperidine-1-yl)-5-(2-fluoro-4-pyridyl)oxazole (90 mg; 0.245 mmol) and (aminomethyl)cyclopropane (4 ml) are heated in a sealed steel cylinder at 190 C for 1.5 h, the amine evaporated and the residue purified via SiO$_2$ chromatography (TBME/MeOH/NH$_3$conc 90/10/1) to yield the title compound (61 mg: 60%).

1H-NMR (400 MHz; DMSO-d6): 0.17 (bq, 2H); 0.43 (bq, 2H); 0.95–1.05 (m, 1H); 1.88–1.98 (bd, 2H); 2.07–2.18 (m, 2H); 2.19 (s, 3H); 2.46–2.50 (bs, 4H); 3.08–3.12 (m, 2H); 5.68 (s, 1H, OH); 6.51 (d, 1H); 6.68 (s, 1H); 6.87 (t, 1H, NH); 7.32 (t, 2H); 7.65 (dd, 2H); 7.97 (d, 1H).

MS (e/z) EI: 422 (M+, 30); 404 (30); 352 (30); 71 (100)

Example 16

4-(4-Fluorophenyl)-2-(1-hydroxy-4-ethyl)piperidine-1-yl)-5-(2-cyclohexyl amino-4-pyridyl)oxazole

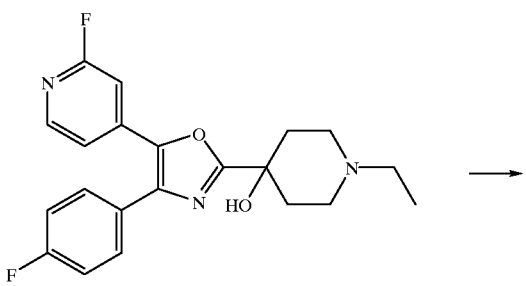

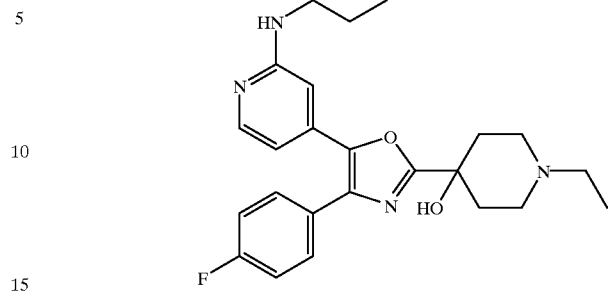

The title compound is prepared according to the procedure above and obtained as colorless crystals in 83% yield.

1H-NMR (400 MHz; CDCl$_3$): 1.16 (t, 3H); 1.16–1.40 (m, 6H); 1.61–1.81 (m, 2H); 1.92–2.06 (m, 4H); 2.40 (dt, 2H); 2.48–2.61 (m, 4H); 2.78 (bd, 2H); 2.92 (s, 1H, OH); 3.36 (m, 1H); 4.53 (d, 1H, NH); 6.45 (s, 1H); 6.67 (d, 1H); 7.13 (t, 2H); 7.63 (dd, 2H); 8.08 (d, 1H).

MS (e/z) EI: 464 (M+, 60); 447 (50); 446 (55).

Example 17

4-(4-Fluorophenyl)-2-(1-hydroxy-4-ethyl)piperidine-1-yl)-5-(2-cyclohexyl amino-4-pyridyl)oxazole

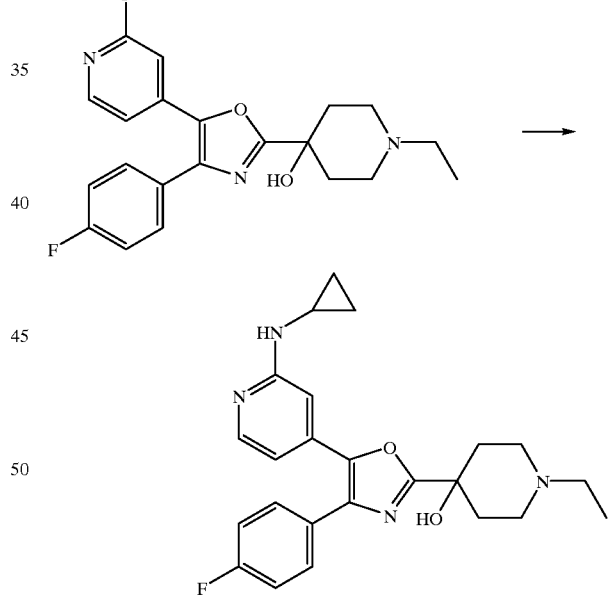

The title compound is prepared according to the procedure above and obtained as cream colored crystals 48% yield.

1H-NMR (400 MHz; CDCl$_3$): 0.48(m, 2H); 0.66 (m, 2H); 1.13 (t, 3H); 2.02 (bd, 2H); 2.34–2.46 (m, 3H); 2.49–2.62 (m, 4H); 2.78 (bd, 2H); 3.06 (s, 1H, OH); 5.17 (s, 1H, NH); 6.79 (dd, 1H); 6.87 (s, 1H); 7.13 (t, 2H); 7.68 (dd, 2H); 8.08 (d, 1H).

MS (e/z) EI: 422 (M+, 50); 405 (28); 404 (30); 338 (28); 85 (100).

Example 18

4-(4-Fluorophenyl)-2-(4-NH-piperidine-1-yl)-5-(2-(1-(S)-phenylethyl)amino-4-pyridyl)oxazole a) 4-(4-Fluorophenyl)-(2-(4-N-tert.butyloxy carbonyl)piperidine-1-yl)-5-(2-fluoro-4-pyridyl)oxazole

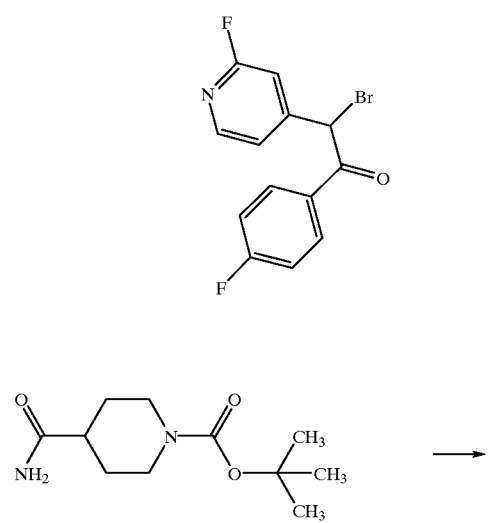

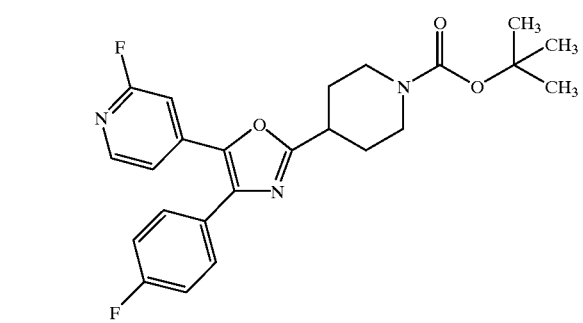

4-Fluoro-2-bromo-(2-fluoropyridin-4-yl)acetophenone (2.1 g; 4.76 mmol) and 1-tert.butyloxycarbonyl piperidine-4-carboxylic acid amide (6 g, 26.3 mmol) are mixed and heated as a melt at 162 C for 20 min. The reaction mixture is dissolved in MeOH (ca 10 ml) and combined with TBME (130 ml). The precipitate is filtered off, the filtrate evaporated to dryness and with EtOH/HClconc (2 ml/2 ml) for 10 min, poured on water and extracted three times with TBME. The aqueous phase is adjusted to pH~10 by adding a saturated solution of $Na_2CO_3$ and extracted with ethyl acetate three times. The combined organic phases are washed with water, dried over $Na_2SO_4$, filtered and evaporated to dryness and yielded the piperidine NH analogue of the title compound (177 mg; 0.52 mmol; 8%), which is treated with $(BOC)_2O$ (150 mg; 0.68 mmol) in THF (2 ml) for 1 h at room temperature. The reaction mixture is evaporated to yield the title compound as a colorless foam (270 mg), which is directly used for the next step without purification.

b) 4-(4-Fluorophenyl)-2-(4-N-tert.butyloxy carbonyl)piperidine-1-yl)-5-[2-(S)-phenylethyl]amino-4-pyridyl)oxazole

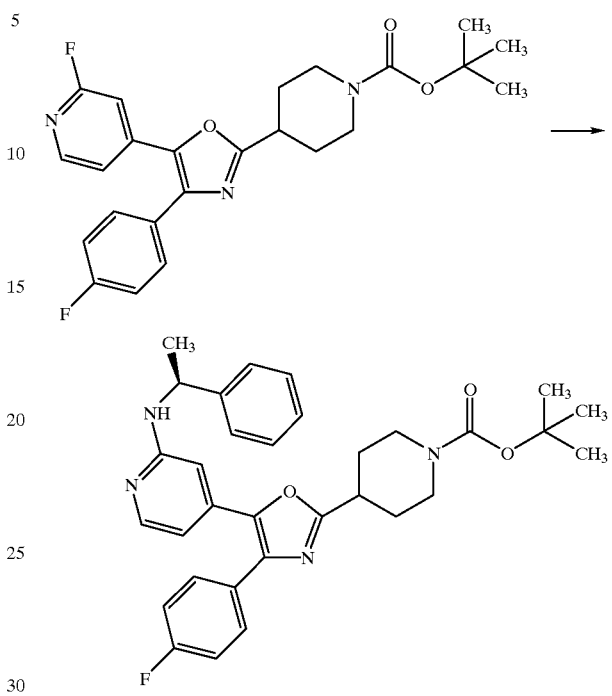

4-(4-(Fluorophenyl)-2-(4-N-tert.butyloxy carbonyl)piperidin-1-yl)-5-(2-fluoro-4-pyridyl)oxazole (270 mg) and 1-(S)phenylethylamine (3 ml) are heated to 185 C for 2.5 h, evaporated and purified by $SiO_2$ chromatography (TBME/hexanes 1/1 to 100/0) to yield the title compound as a colorless foam (145 mg; 52%).

1H-NMR (400 MHz; DMSO-d6) mixture of rotamers: 1.40–1.45 (s, 12H); 1.56–1.71 (m, 2H); 2.00–2.08 (bd, 2H); 2.90–3.05 (bs, 2H); 3.08–3.19 (m, 1H); 3.90–4.02 (bd, 2H); 4.90–5.00 (bs, 1H); 6.49 (d, 1H); 6.66 (s, 1H); 7.13–7.32 (m, 8H); 7.60 (dd, 2H); 7.91 (d, 1H).

MS (e/z) EI: 542 (M+, 100); 485 (30); 441(30); 386(60); 120(60); 105 (60); 57(75).

c) 4-(4-Fluorophenyl)-2-(4-NH-piperidine-1-yl)-5-(2-(1-(S)-phenylethyl)amino-4-pyridyl)oxazole

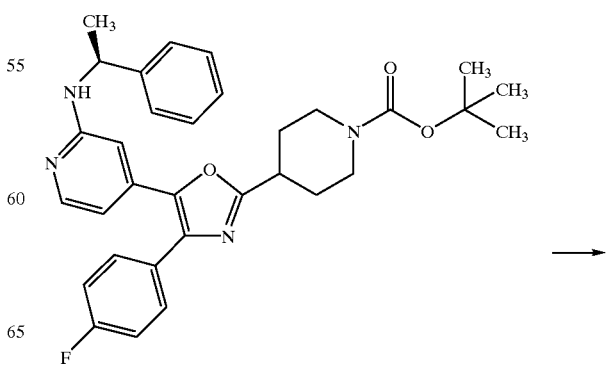

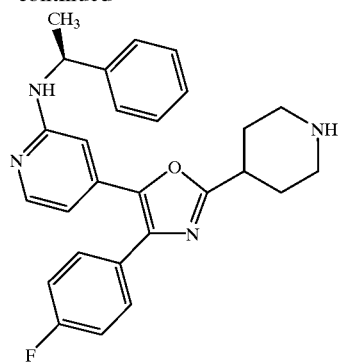

4-(4-Fluorophenyl)-2-(4-N-tert.butyloxy carbonyl)piperidine-1-yl-5-[2-(1-(S)-phenylethyl]amino-4-pyridyl)oxazole (140 mg; 0.258 mmol) is dissolved in EtOH/HCl conc (4 ml; 1:1) and treated at room temperature for 5 min. Water is added and the reaction mixture extracted with TBME twice. The combined organic phases are mixed with a saturated solution of $Na_2CO_3$ and extracted with ethyl acetate three times. The combined organic phases are dried over $Na_2SO_4$ and evaporated to yield the title compound as a colorless foam (90 mg; 80%).

1H-NMR (400 MHz; DMSO-d6) mixture of rotamers: 1.42 (d, 3H); 1.58–1.70 (m, 2H); 1.92–2.03 (m, 2H); 2.08–2.30 (bs, 1H, NH); 2.55–2.65 (dd, 2H); 2.92–3.03 (m, 3H); 4.90–5.00 (m, 1H); 6.48 (d, 1H); 6.66 (s, 1H); 7.15–7.33 (m, 8H); 7.58 (dd, 2H); 7.90 (d, 1H).

MS (e/z) EI: 442 (M+, 70); 386 (100); 105 (55).

Example 19

4-(4-Fluorophenyl)-2-(4-NH-piperidine-1-yl)-5-(2-cyclopropylmethylamino-4-pyridyl)oxazole a) 4-(4-Fluorophenyl)-2-(4-N-tert.butyloxy carbonyl)piperidine-1-yl)-5-(2-cyclopropylmethyl)amino-4-pyridyl)oxazole

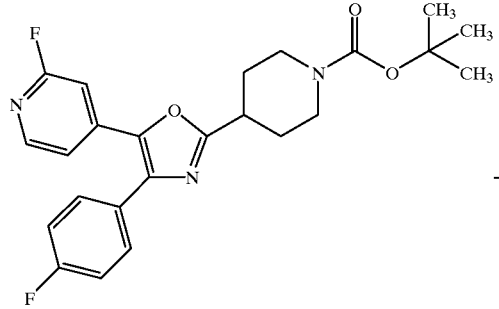

4-(4-Fluorophenyl)-2-(4-N-tert.butyloxy carbonyl)piperidine-1-yl)-5-(2-fluoro-4-pyridyl)oxazole (200 mg; 0.45 mmol) and aminomethyl)cyclopropane (2 ml) are refluxed for 3.5 h, evaporated and purified by $SiO_2$ chromatography (TBME/hexanes 4/6) to yield the title compound as a colorless foam (190 mg, 85%).

b) 4-(4-Fluorophenyl)-2-(4-NH-piperidine-1-yl)-5-(2-cyclopropylmethylamino-4-pyridyl)oxazole

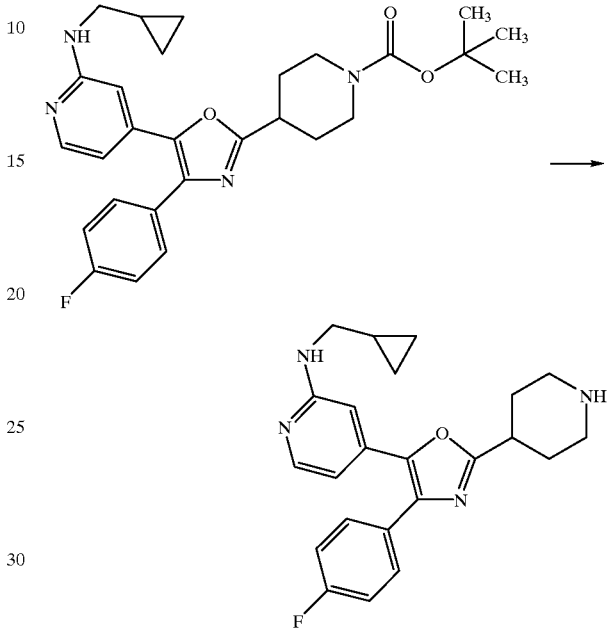

is treated with EtOH/HCl conc in analogously as for compound 14.

1H-NMR (400 MHz; DMSO-d6): 0.19 (dd, 2H); 0.45 (dd, 2H); 0.95–1.06 (m, 1H); 1.58–1.71 (dq, 2H); 1.92–2.01 (dd, 2H); 2.08–2.28 (bs, 1H, NH); 2.61 (dt, 2H); 2.93–3.03 (m, 3H); 3.10 (t, 2H); 6.50 (d, 1H); 6.67 (s, 1H); 6.82 (t, 1H, NH); 7.30 (t, 2H); 7.65 (dd, 2H); 7.97 (d, 1H).

MS (e/z) ESI: 393.2 (MH+, 60).

Example 20

4-(4-Fluorophenyl)-2-(4-N-(2-hydroxy-2-methyl)propylpiperidine-1-yl)-5-(2-cyclopropylmethylamino-4-pyridyl)oxazole

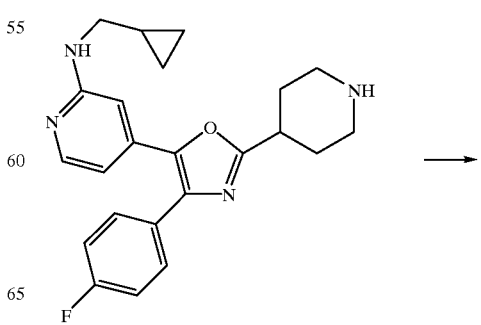

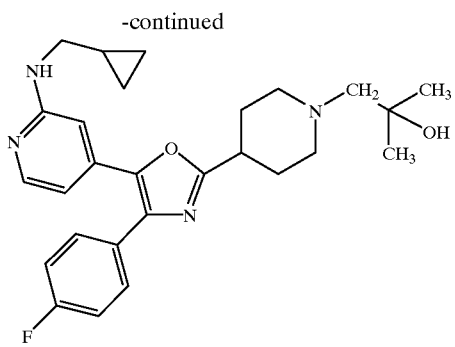

4-(4-Fluorophenyl)-2-(4-NH-piperidine-1-yl)-5-(2-[cyclopropylmethyl]amino-4-pyridyl)oxazole (76 mg; 0.19 mmol) and isobutylene oxide (0.1 ml; 1.4 mmol) are dissolved in ethanol and heated in a closed vessel to 80 C for 2 h. Evaporation to dryness and purification via SiO$_2$ chromatography rendered the title compound as a white solid (51 mg; 57%).

1H-NMR (400 MHz; DMSO-d6): 0.18 (dd, 2H); 0.44 (dq, 2H); 0.93–1.05 (m, 1H); 1.11 (s, 6H); 1.84 (dq, 2H); 1.99 (bd, 2H); 2.21 (s, 2H); 2.28 (bt, 1H); 2.82–2.91 (m, 1H); 2.97 (bd, 2H); 3.10 (t, 2H); 4.07 (s, 1H, OH); 6.49 (d 1H); 6.66 (s, 1H); 6.82 (t, 1H, NH); 7.31 (t, 2H); 7.63 (dd, 2H); 7.97 (d, 1H).

MS (e/z) ESI: 465.3 (MH+).

Example 21

4-(4-Fluorophenyl)-2-(4-NH-piperidine-1-yl)-5-(2-cyclohexylamino-4-pyridyl)oxazole a) 4-(4-Fluorophenyl)-2-(4-N-tert.butyloxy carbonyl)piperidine-1-yl)-5-(2-cyclohexyl)amino-4-pyridyl)oxazole

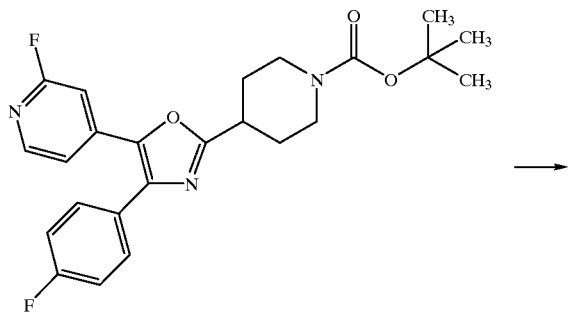

4-(4-(Fluorophenyl-2-(4-N-tert.butyloxy carbonyl)piperidine-1-yl)-5-(2-fluoro-4-pyridyl)oxazole (100 mg; 0.226 mmol) is refluxed in cyclohexylamine (2 ml) for 4 h, evaporated and purified by SiO$_2$ chromatography (TBME/hexanes 4/6) to yield the title compound (74 mg; 63%).

b) 4-(4-Fluorophenyl)-2-(4-NH-piperidine-1-yl)-5-(2-cyclohexylamino-4-pyridyl)oxazole

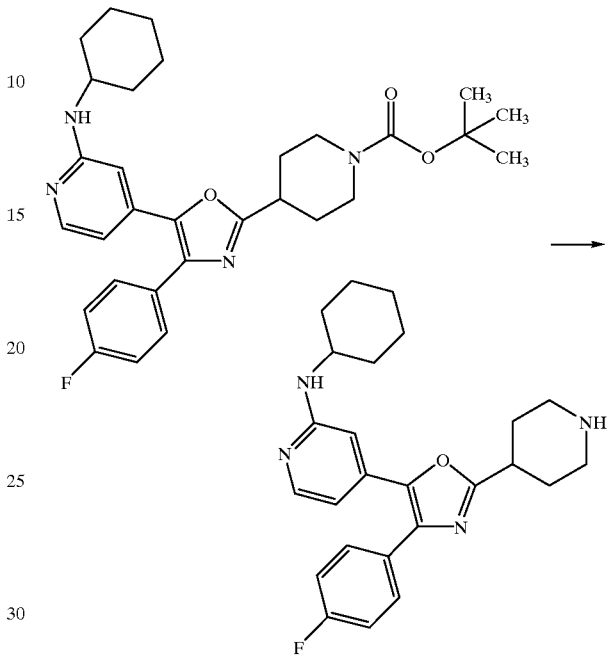

4-(4-Fluorophenyl)-2-(4-N-tert.butyloxy carbonyl)piperidine-1-yl)-5-(2-cyclohexyl)amino-4-pyridyl)oxazole (70 mg; 0.13 mmol) is treated analogously as for compound 14 to yield the title compound as pale yellow crystals (41 mg; 74%).

1H-NMR (400 MHz; DMSO-d6): 1.11–1.33 (m, 5H); 1.53–1.75 (m, 5H); 1.97 (bd, 2H); 1.96 (bd, 2H); 2.05–2.21 (bs, 1H, NH); 2.61 (dt, 2H); 2.92–3.03 (m, 3H); 3.53–3.65 (m, 1H); 6.47 (d, 1H); 6.58 (d, 1H, NH); 6.61 (s, 1H); 7.30 (t, 2H); 7.63 (dd, 2H); 7.95 (d, 1H).

MS (e/z) ESI: 421.3 (MH+, 70).

Example 22

4-(4-Fluorophenyl-2-(4-N-(2-hydroxy-2-methyl)propylpiperidine-1-yl)-5-(2-(1-(S)-phenylethyl)amino-4-pyridyl)oxazole

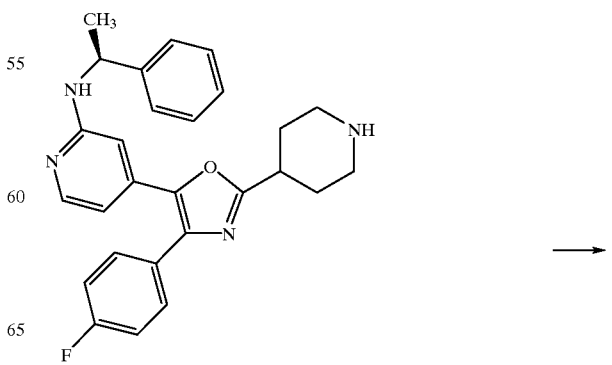

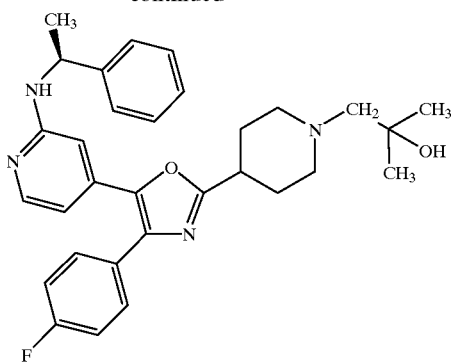

4-(4-(Fluorophenyl)-2-(4-NH-piperidine-1-yl)-5-(2-(1-(S)-phenylethyl)amino-4-pyridyl)oxazole (45 mg; 0.11 mmol) is treated analogously as for compound 14 with isobutylene oxide to render the title compound (34 mg; 66%) as a colorless foam.

1H-NMR (400 MHz; DMSO-d6): 1.11 (s, 6H); 1.42 (d, 3H); 1.83 (bq, 2H); 1.98 (bd, 2H); 2.22 (s, 2H); 2.28 (bt, 2H); 2.81–2.91 (m, 1H); 2.99 (bd, 2H); 4.07 (s, 1H, OH); 4.90–5.02 (m, 1H); 6.48 (d, 1H); 6.67 (s, 1H); 7.15–7.24 (m, 2H); 7.25–7.33 (m, 6H); 7.60 (dd, 2H); 7.92 (d, 1H).

MS (e/z) EI: 499 (M-CH3, 5); 455 (100).

Example 23

4-(4-Fluorophenyl)-2-(4-N-(2-hydroxy-2-methyl)propylpiperidine-1-yl)-5-(2-cyclohexylamino-4-pyridyl)oxazole

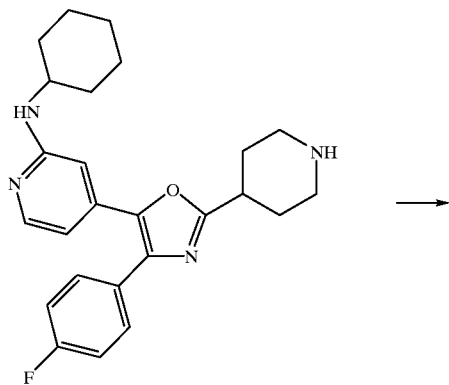

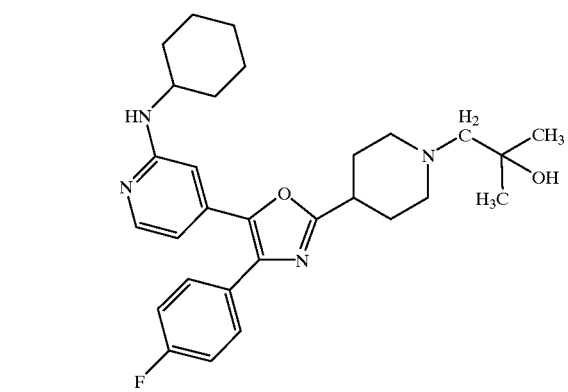

The title compound is prepared according to the procedure above and obtained as colorless crystals in 95% yield.

1H-NMR (400 MHz; CDCl3): 1.21. (s, 6H); 1.12–1.42 (m, 6H); 1.62–1.71 (m, 1H); 1.71–1.81 (m, 2H); 1.95–2.16 (m, 5H); 2.39 (s, 2); 2.52 (t, 2H); 2.85–2.95 (m, 1H); 3.05 (bd, 2H); 3.18 (s, 1H, OH); 3.31–3.42 (m, 1H); 4.50 (d, 1H, NH); 6.45 (s, 1H); 6.70 (d, 1H); 7.12 (t, 2H); 7.63 (dd, 2H); 8.05 (d, 1H).

MS (e/z) ESI: 493.4 (MH+, 20); 247.3 (100).

Example 24

4-(4-Fluorophenyl)-2-(4-N-(2-hydroxy-2-methyl)propylpiperidine-1-yl)-5-(2-cyclopropylamino-4-pyridyl)oxazole

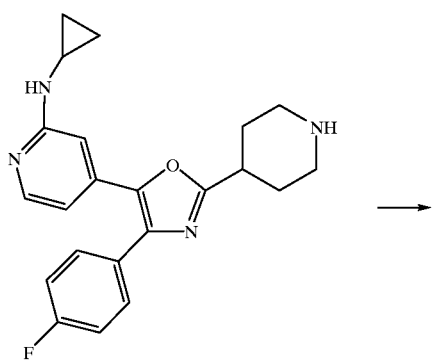

The title compound is prepared according to the procedure above and obtained as colorless crystals in 95% yield.

1H-NMR (400 MHz; CDCl3): 0.52 (bq, 2H); 0.68 (bq, 2H); 1.21 (s, 6H); 2.00–2.20 (m, 4H); 2.40 (s, 3H); 2.53 (bt, 2H); 2.88–2.98 (m, 1H); 3.04 (bd, 2H); 3.20 (s, 1H, OH); 5.03 (s, 1H, NH); 6.83 (d, 1H); 6.88 (s, 1H); 7.13 (t, 2H); 7.67 (dd, 2H); 8.08 (d, 1H).

MS (e/z) ESI: 451.2 (MH+, 25); 226.1 (100); 217.2 (50).

Example 25

4-(4-Fluorophenyl)-2-(4-N-(2-hydroxy-2-methyl)propylpiperidine-1-yl)-5-(2-(1-(S)-phenylethyl)amino-4-pyrimidyl)oxazole

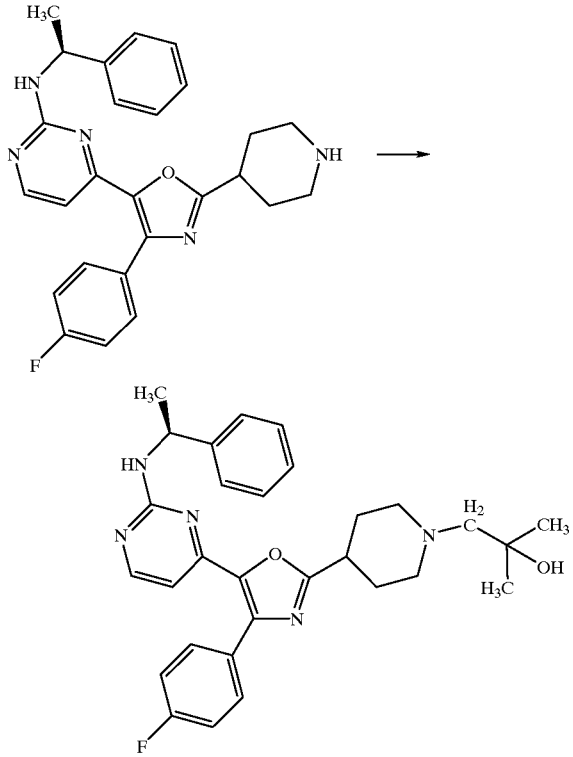

The title compound is prepared according to the procedure above from 4-(4-fluorophenyl)-5-(2-[1-(S)-phenylethyl]amino-4-pyrimidyl)-2-(4-NH-piperidine-1-yl)oxazole (Example 7) and obtained as colorless crystals in 85% yield.

1H-NMR (400 MHz; CDCl$_3$): 1.18 (s, 6H); 1.52 (d, 3H); 1.98–2.17 (m, 4H); 2.38 (s, 2H); 2.52 (bt, 2H); 2.87–2.97 (m, 1H); 3.05 (d, 2H); 3.16 (bs, 1H, OH); 5.08 (bs, 1H); 5.40 (d, 1H, NH); 6.85 (d, 1H); 7.07 (t, 2H); 7.23–7.36 (m, 5H); 7.95 (dd, 2H); 8.32 (d, 1H).

MS (e/z) ESI: 516.3 (MH+, 75); 258.7 (100).

Example 26

3-Bromo-2-(4-fluorophenyl)-1-(2-[1-(S)-phenylethyl]amino-4-pyrimidyl)imidazole a) 4,5-Dibromo-2-(4-fluorophenyl-1-(2-trimethylsilanyl-ethoxymethyl)imidazole

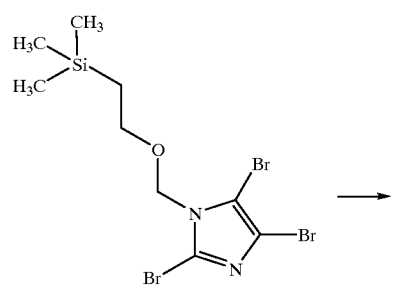

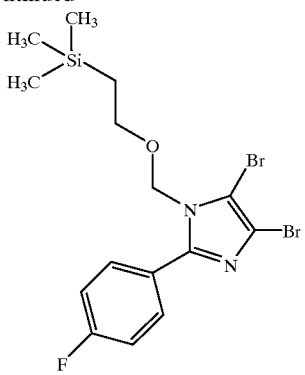

2,4,5-Tribromo-1-(2-trimethylsilanyl-ethoxymethyl)imidazole (Tetrahedron Lett. (1998), 39(29), 5171–5174) (12.2 g; 28.2 mmol), 4-fluorophenyl-boronic acid (4.34 g; 31.02 mmol) and Pd(PPh3)4 (1.6 g; 1.4 mmol) are dissolved in 1,2-dimethoxy-ethane (122 ml) and saturated Na$_2$CO$_3$ solution (36.5 ml) and refluxed for 24 h. Water is added to the reaction mixture and the aqueous phase extracted three times with ethyl acetate. The combined organic phases are washed with 2N Na$_2$CO$_3$ and saturated NaCl-solution, dried over Na$_2$SO$_4$, filtered and evaporated to dryness. Purification over SiO$_2$ (Cyclohexane/EtOAc 99.7:0.3>90:10) yields the desired product as a white solid (9.9 g; 78%).

1H-NMR (400 MHz; DMSO-d6): 0.00 (s, 9H); 0.85 (t, 2H); 3.52 (t, 2H); 5.33 (s, 2H); 7.39 (dd, 2H); 7.78 (dd, 2H).
MS (m/z) EI: 450 (MH+; 20).

b) 4-Bromo-2-(4-fluorophenyl)-1-(2-trimethylsilanyl-ethoxymethyl)imidazole

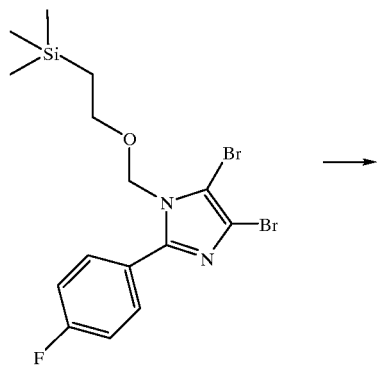

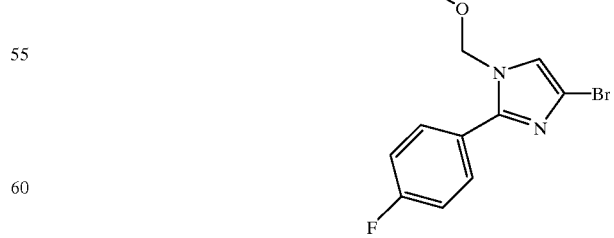

4,5-Dibromo-2-(4-fluorophenyl)-1-(2-trimethylsilanyl-ethoxymethyl)imidazole (10.8 g; 25 mmol) are dissolved in THF (108 ml) and cooled to −78 C under argon. N-BuLi (15.6 ml; 1.6 M) is added under stirring within 15 min. After 30 min at −78 C, isopropanol (7.8 ml; 0.1 mol) is introduced dropwise and the mixture warmed to room temperature. Water is added to the reaction mixture and the aqueous phase extracted three times with ethyl acetate. The combined organic phases are washed with saturated NaCl-solution, dried over Na2SO4, filtered and evaporated to dryness, yielding the title compound as colorless oil (9.1 g; 95%).

1H-NMR (400 MHz; DMSO-d6): 0.00 (s, 9H); 0.86 (t, 2H); 3.58 (t, 2H); 5.33 (s, 2H); 7.35 (dd, 2H); 7.68 (s, 1H); 7.82 (dd, 2H).

MS (m/z) EI: 372 (M+).

c) 4-Bromo-2-(4-fluorophenyl)-1-H-imidazole

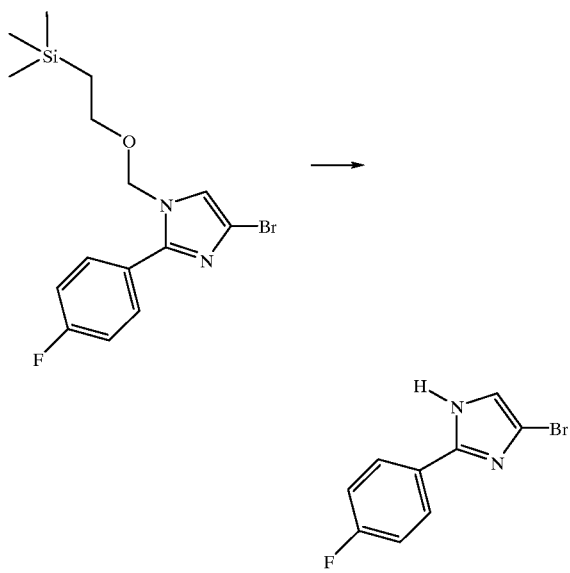

4-Bromo-2-(4-fluorophenyl)-1-(2-trimethylsilanyl-ethoxymethyl)imidazole (3.4 g; 9 mmol) is dissolved in EtOH (34 ml) and HCl conc. (37%; 34 ml) and heated to 55 C for 1 h. Water is added to the reaction mixture and the aqueous phase extracted three times with ethyl acetate. The combined organic phases are washed with 2N Na2CO3 and saturated NaCl-solution, dried over Na2SO4, filtered and evaporated to dryness to yiled the title compound as colorless crystals (2.1 g, 92%).

1H-NMR (400 MHz; DMSO-d6): 7.32 (dd, 2H); 7.42 (s, 1H); 7.93 (dd, 2H).

MS (m/z) EI: 242 (M+; 90), 240 (90), 161 (75), 134 (100), 107 (60).

d) 4-Bromo-2-(4-fluorophenyl)-1-(4-(2-methylthio)pyrimidyl)imidazole

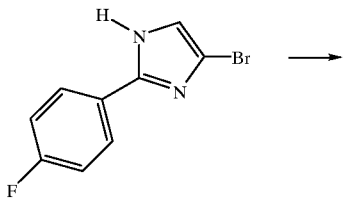

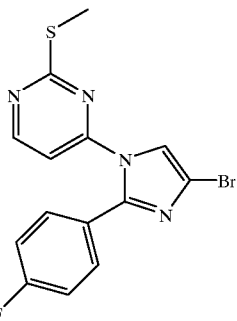

4-Bromo-2-(4-fluorophenyl-1-H-imidazole (1.2 g; 4.9 mmol) is dissolved in DMF (20 ml) and cooled to 0 C under argon. KN(TMS)₂ (10.5 ml of a 0.5 M solution in toluene; 5.22 mmol) is added dropwise under stirring. After stirring for 15 min at 0 C, 4-chloro-2-methylthiopyrimidine (837 mg; 5.22 mmol) in DMF (1 ml) is added dropwise and the reaction mixture gradually warmed to room temperature and heated at 80 C for 12 h. The reaction mixture is poured on saturated NaCl solution and extracted with TBME three tines. The combined organic phases are dried over Na₂SO₄, filtered, evaporated to dryness and purified by SiO₂ chromatography (TBME/hexanes 2:8 to 3:7) to yield the title compound as yellow crystals (1.35 g; 74%).

1H-NMR (400 MHz; DMSO-d6): 2.15 (s, 3H); 7.18 (d, 1H); 7.27 (dd, 2H); 7.48 (dd, 2H); 8.10 (s, 1H); 8.72 (d, 1H).

MS (m/z) CI: 365 (100); 363 (M+; 100).

e) 4-Bromo-2-(4-fluorophenyl)-1-(4-(2-methylsulfinyl)pyrimidyl)imidazole

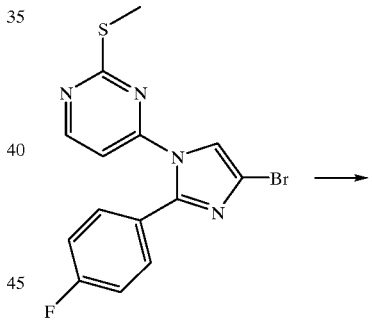

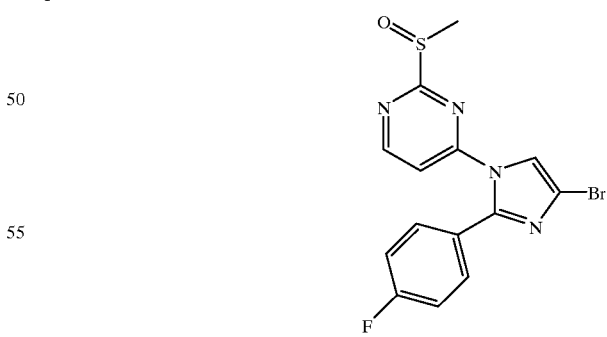

4-Bromo-2-(4-fluorophenyl-(1-(4-(2-methylthio)pyrimidyl)imidazole (1.35 g; 3.7 mmol) is dissolved in methylene chloride (20 ml) and cooled to 0 C. mCPBA (70% in water, 1.18 g 4.8 mmol) dissolved in methylene chloride (10 ml) is added dropwise and stirring continued for 5 min at 0 C. The reaction mixture is poured on saturated Na₂CO₃ solution and extracted with ethyl acetate three times. The combined organic phases were dried over Na₂SO₄, filtered and evaporated to dryness yielding the title compound as light brown foam (1,3 g; 92%) which was used for the next step without further purification.

1H-NMR (400 MHz; DMSO-d6): 2.70 (s, 3H); 7.28 (dd, 2H); 7.53 (dd, 2H); 7.58 (d, 1H); 8.18 (s, 1H); 9.10 (d, 1H)

MS (m/z) EI: 382 (100; M+), 380 (100).

f) 4-Bromo-2-(4-fluorophenyl)-1-(2-[1-(S)-phenylethyl]amino-4-pyrimidyl)imidazole

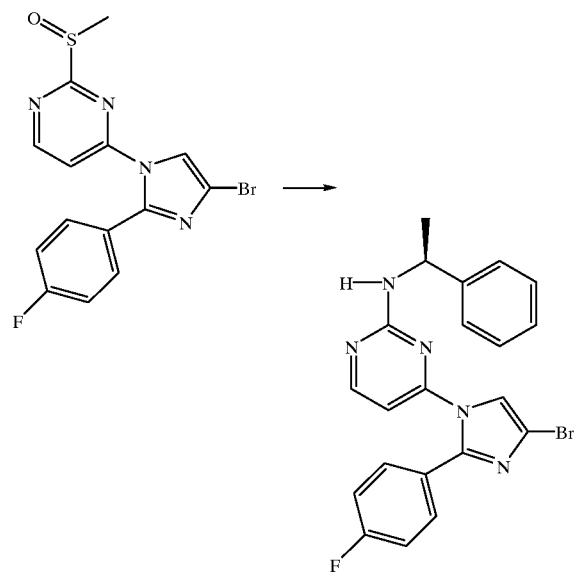

4-Bromo-2-(4-fluorophenyl)-1-(4-(2-methylsulfinyl)pyrimidyl)imidazole (1.3 g; 3.4 mmol) is dissolved in S-(–)-1-phenylethylamine (6 ml) and heated at 120 C for 15 min. After evaporation of the amine, the residue is purified by SiO₂ chromatography (TBME/hexanes 4:6) to yield the title compound as pale brown foam (0.94 g; 62%).

1H-NMR (400 MHz DMSO-d6: tautomeric mixture with broad signals. 1.28 (bs, 1.8H); 1.42 (bs, 1.2H); 4.42 (bs, 0.7H); 5.13 (bs, 0.3H); 6.38 (bs, 0.3H); 6.5 bs, 0.7H); 7.15–7.32 (m, 7H); 7.45 (bt, 2H); 7.80 (bs, 1H); 8.10 (bd, 1H); 8.47 (bs, 1H).

MS (m/z) EI: 382 (100; M+), 380 (100).

Example 27

4-Bromo-2-(4-fluoromethylphenyl)-1-(2-cyclohexylamino-4-pyrimidyl)imidazole

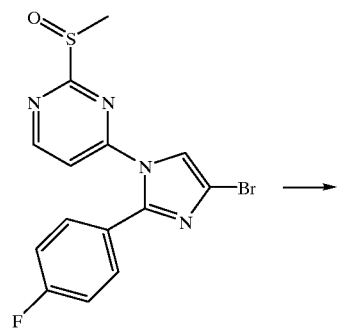

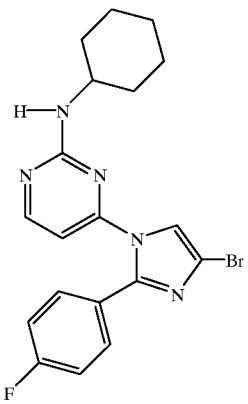

The title compound is prepared according to the procedure described above and obtained as colorless crystals in 76% yield.

Example 28

Similar to Example 26 a) to f) above a 2-(3-trifluoromethylphenyl-product and corresponding intermediates are prepared according to the procedure described above.

a) 4,5-Dibromo-2-(3-trifluoromethylphenyl)-1-(2-trimethylsilyl-ethoxymethyl)imidazole

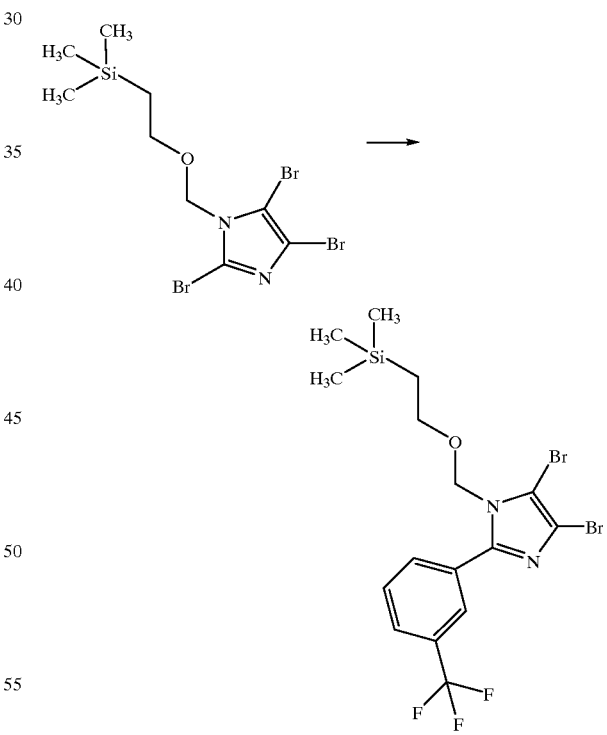

The title compound is prepared according to the procedure above using 3-trifluoromethylphenylboronic acid and obtained as a viscous oil in 64% yield after purification over SiO₂.

1H-NMR (200 MHz; CDCl₃): 0.00 (s, 9H); 0.98 (t, 2H); 3.70 (t, 2H); 5.25 (s, 2H); 757 (t, 1H); 7.69 (d, 1H); 8.01 (d, 1H); 8.12 (d, 1H).

MS (m/z) EI: 500 (M+; 20), 457 (70), 442 (50), 376 (25), 350 (20), 103 (35).

b) 4-Bromo-2-(3-trifluoromethylphenyl)-1-(2-trimethylsilyl-ethoxymethyl)imidazole.

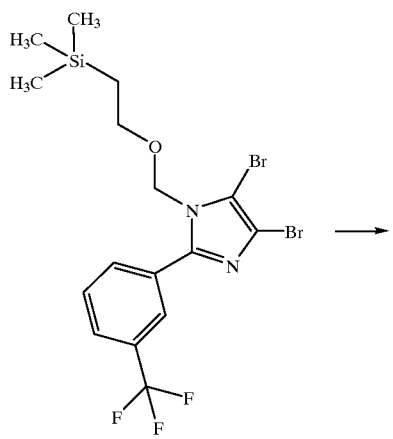

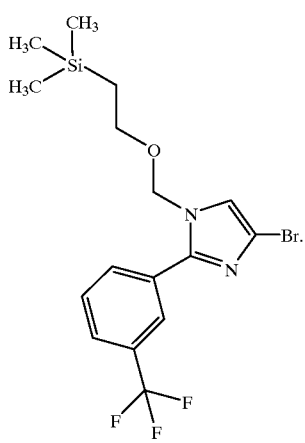

The title compound is prepared according to the procedure above, obtained as a viscuous oil in quantitative yield and used in the next step without further purification.

1H-NMR (200 MHz; CDCl₃): 0.00 (s, 9H); 0.96 (t, 2H); 3.61 (t, 2H); 522 (s, 2H); 7.10 (s, 1H); 7.57 (dd, 1H); 7.68 (d, 1H); 8.00 (d, 1H); 8.10 (s, 1H).

MS (m/z) CI: 424 (20), 423 (80), 422 (40), 421 (MH+; 90), 403 (100), 401 (95), 393 (80), 391 (60), 378.9 (80), 376.9 (80), 364.9 (100), 362.9 (100).

c) 4-Bromo-2-(3-trifluoromethylphenyl)-1-H-imidazole

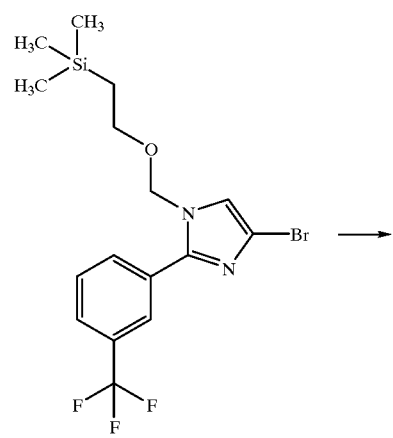

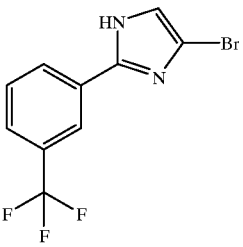

The title compound is prepared according to the procedure described above and obtained as slightly yellow crystals in 94% yield.

1H-NMR (400 MHz; CDCl₃): 7.17 (s, 1H); 7.58 (dd, 1); 7.65 (d, 1H); 8.02 (d, 1H); 8.10 (s, 1H).

MS (m/z) ESI: 292 (M+1; 100), 291 (M+; 100).

d) 4-Bromo-2-(3-trifluoromethylphenyl)-1-(4-(2-methylthio)pyrimidyl)imidazole

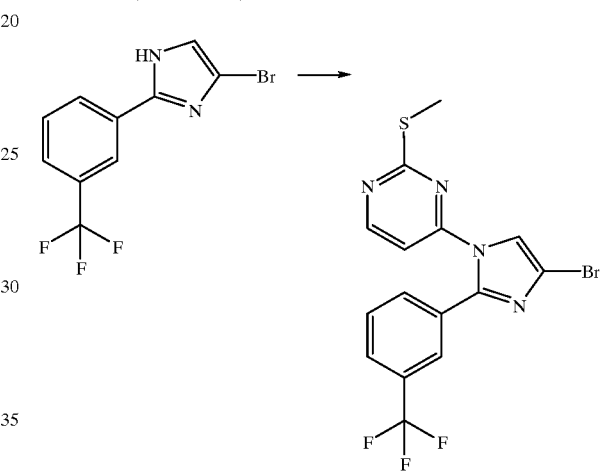

The title compound is prepared according to the procedure described above and obtained as slightly yellow crystals in 61.3% yield.

1H-NMR (400 MHz; CDCl₃): 2.40 (s, 3H); 6.58 (d, 1H); 7.55 (dd, 1H); 7.61 (d, 1H); 7.67 (s, 1H); 7.73 (d, 1H); 7.85 (s, 1H); 8.49 (d, 1H).

MS (m/z) EI: 416 (M+, 100); 414 (100); 335 (60); 164 (45).

e) 4-Bromo-2-(3-trifluoromethylphenyl)-1-(4-(2-methylsulfinyl)pyrimidyl)imidazole

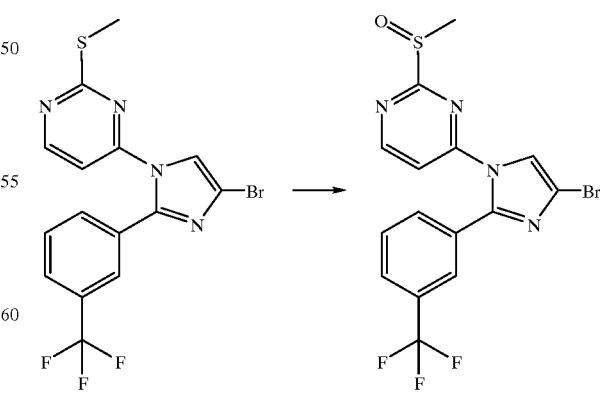

The title compound is prepared according to the procedure described above and obtained as slightly yellow crystals in 90% yield.

1H-NMR (400 MHz; CDCl₃): 2.92 (3H); 6.97 (d, 1H); 7.58–7.68 (m, 2H); 7.78 (d, 1H); 7.83 (bs, 2H); 8.84 (d, 1H).

MS (m/z) CI: 433 (98); 431 (M+, 100); 413 (80); 411 (75).

f) 4-Bromo 2-(3-trifluoromethylphenyl)-1-(2-cyclopentylamino-4-pyrimidyl)imidazole

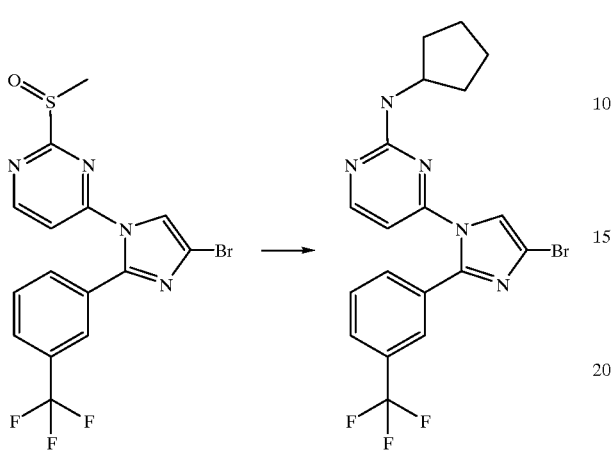

The title compound is prepared according to the procedure described above and obtained as slightly yellow crystals in 78% yield.

1H-NMR (400 MHz; CDCl₃): 1.30–2.22 (m, 8H); 3.75–4.00 (bs, 1H); 5.10–5.45 (bs, NH, 1H); 6.17 (bs, 1H); 7.51 (dd, 1H); 7.55 (s, 1H); 7.65 (d, 1H); 7.69 (d, 1H); 7.86 (s, 1H); 8.23 (d, 1H).

MS (m/z) EI: 452 (M+, 100); 450 (100); 384 (70); 382 (70); 372 (30); 304 (35); 94 (85).

Example 29

4-Bromo-2-(3-trifluoromethylphenyl)-1-(2-cyclopropylamino-4-pyrimidyl)imidazole

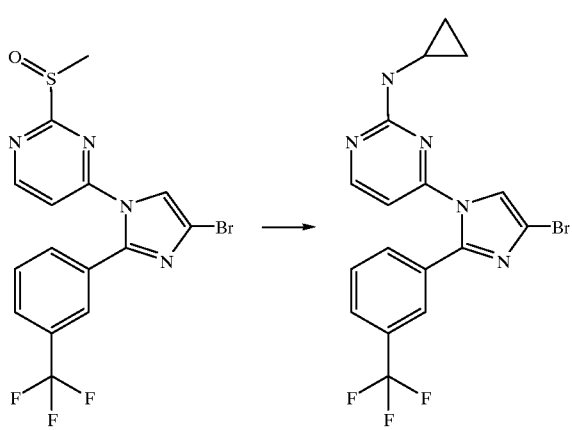

The title compound is prepared according to the procedure described above and obtained as slightly yellow crystals in 73% yield.

1H-NMR (400 MHz; CDCl₃): 0.50 (bs, 2H); 0.78 (bs, 2H); 2.52–2.77 (bs, 1H); 5.50 (bs, 1H); 6.24 (d, 1H); 7.52 (dd, 1H); 7.58 (s, 1H); 7.67 (d, 1H); 7.71 (d, 1H); 7.88 (s, 1H); 8.30 (d, 1H).

MS (m/z) CI: 426 (98); 424 (M+, 100); 406 (23); 404 (25).

Example 30

2-(4-Fluorophenyl)-4-(1-methyl-4-hydroxypiperidin-4-yl-1-(2-[1-(S)-phenylethyl]amino-4-pyrimidyl)imidazole

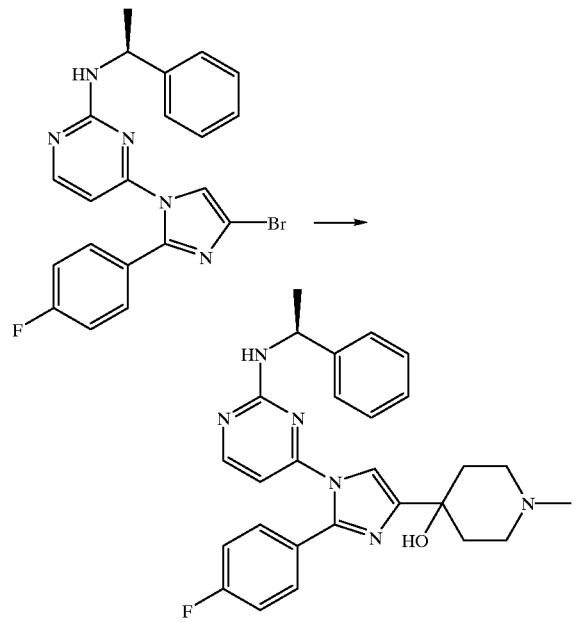

4-Bromo-2-(4-fluorophenyl)-1-(2-[1-(S)-phenylethyl]amino-4-pyrimidyl)imidazole (100 mg; 0.228 mmol) are dissolved in THF (1.4 ml) and cooled to −78 C under argon. BuLi (0.29 ml of a 1.6 M solution in hexane; 0.456 mmol) is introduced and stirring continued for 10 min., N-methyl-4-piperidone (0.027 ml; 0.228 mmol) is added at −78 C and after 2 min the reaction mixture is poured on saturated NaCl solution and extracted with TBME three times. The combined organic phases are dried over Na₂SO₄, filtered and evaporated to dryness. Purification via SiO₂ chromatography (TBME/MeOH/NH₃conc. 90/10/1 to 80/20/1) yielded the title compound as colorless crystals (20 mg; 19%)

1H-NMR (400 MHz; DMSO-d6, 120 C): 1.42 (d, 3H); 2.00 (bd, 2H); 2.23–2.35 (m, 2H); 2.70 (s, 3H; NMe); 3.12 (bs, 4H); 4.78–4.91 (m, 2H); 6.32 (d, 2H); 7.11–7.50 (m, 9H); 8.27 (, 1H).

MS (m/z) EI: 472 (M+); 454 (100); 402 (40); 359 (20); 105 (60); 71 (95).

Example 31

2-(4-Fluorophenyl)-4-(1-methyl-4-hydroxypiperidin-4-yl-1-(2-cyclohexylamino-4-pyrimi-dinyl)imidazole

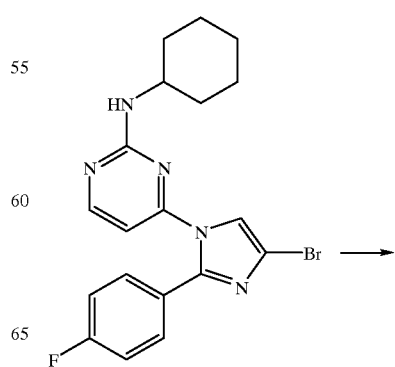

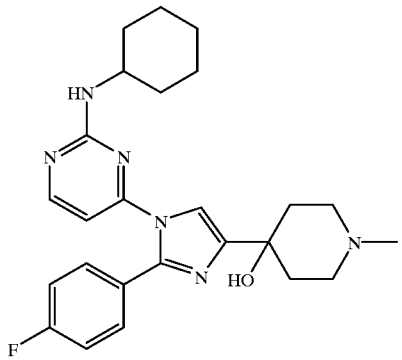

The title compound is prepared according to the procedure described above and obtained as slightly yellow crystals in 46% yield.

1H-NMR (400 MHz; DMSO-d6, 120 C): 1.15–1.28 (m, 6H); 1.48 (m, 1H); 1.65–1.82 (m, 6H); 2.08–2.18 (m, 3H); 2.22 (s, 3H); 2.30–2.40 (m, 1H); 2.42–2.50 (m, 1H); 3.42 (m, 1H); 4.03 (bs, 1H, OH); 6.37 (d, 1H); 6.58 (bd, 1H, NH); 7.15 (d, 1H); 7.18 (d, 1H); 7.43–7.49 (m, 3H); 8.26 (d, 1H).

MS (m/z) EI: 449 (M−1, 100).

Example 32

2-(3-Trifluoromethylphenyl)-4-(1-methyl-4-hydroxypiperidin-4-yl)-1-(2-cyclopropylamino-4-pyrimidyl)imidazole

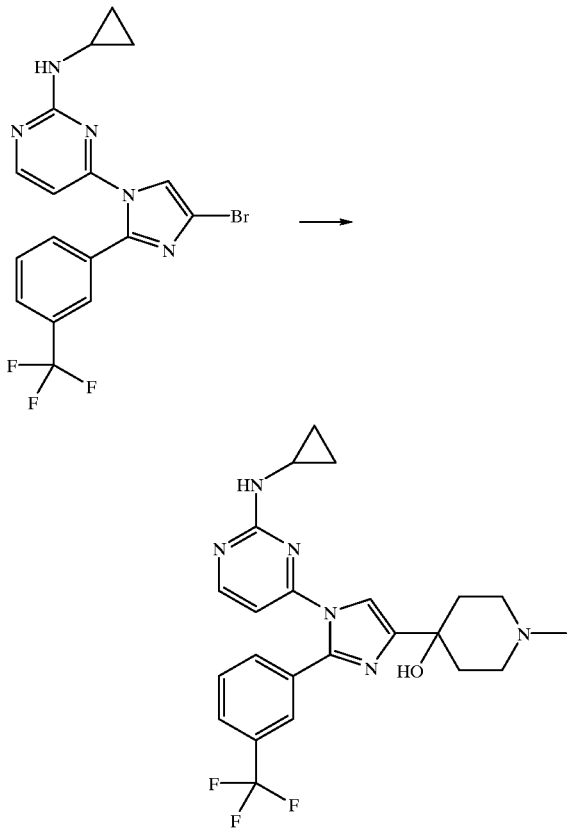

The title compound is prepared according to the procedure described above (except that a 4:1 THF/isopentane mixture was used as solvent and nBuLi was added at −100° C.) and obtained as colorless crystals in 43% yield.

1H-NMR (400 MHz; CDCl3): 0.50 (bs, 2H); 0.78 (bs, 2H); 1.78 (bs, 1H); 2.05 (bd, 2H); 2.12–2.23 (m, 2H); 2.48 (s, 3H); 2.57 (bt, 2H); 2.69–2.82 (m, 3H); 5.50 (bs, 1H, NH); 6.22 (d, 1H); 7.43 (s, 1H); 7.53 (dd, 1H); 7.67 (t, 2H); 7.83 (s, 1H); 8.28 (d, 1H).

MS (m/z) Cm/ES−: 457 (M−1, 100). MS (m/z) Cm/ES+: 459 (MH+, 100).

Example 33

2-(3-Trifluoromethylphenyl)-4-(1-methyl-4-hydroxypiperidin-4-yl)-1-(2-cyclopentylamino-4-pyrimidyl)imidazole

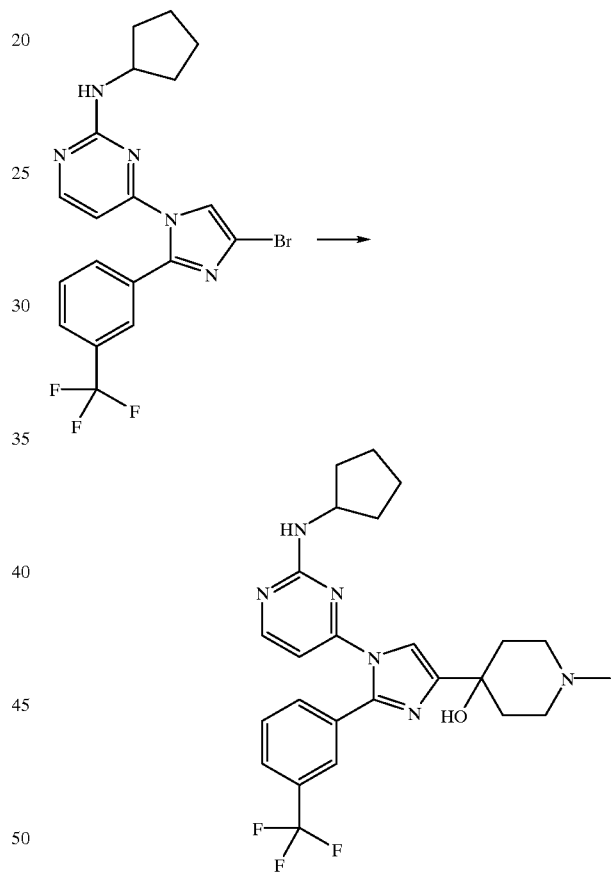

The title compound is prepared according to the procedure described above (THF/isopentane mixture was used as solvent and nBuLi was added at −100° C.) and obtained as colorless viscous oil in 42% yield. Crystallisation as fumarate salt was performed from acetone providing colorless crystals with m.p. 189–193° C.

1H-NMR fumarate (400 MHz; DMSO-d6, 120° C.): 1.32–1.50 (m, 3H); 1.60–1.77 (m, 3H), 1.85 (bd, 2H); 2.18 (m, 2H); 2.32 (s, 3H), 2.53–2.67 (m, 4H); 3.78 (m, 1H); 6.48 (d, 1H); 6.63 (s, 2H, CH of fumarate); 6.78 (m, 1H); 7.51 (s, 1H); 7.61 (bt, 1H); 7.71 (bt, 2H); 8.31 (d, 1H).

MS (m/z) Cm/ES+: 487 (MH+, 40); 469 (100), 426 (15).

Example 34

2-(4-Fluorophenyl)-1-(2-[1-(S)-phenyl-ethyl]amino-4-pyrimidyl) 4-vinylimidazole

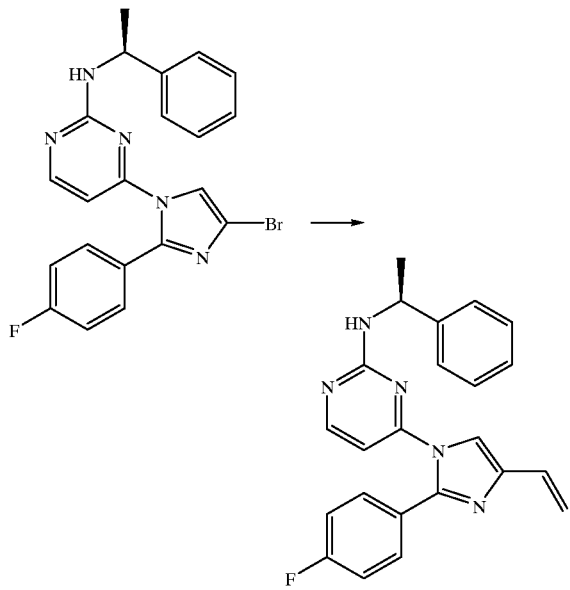

4-Bromo-2-(4-fluorophenyl)-1-(2-[1-(S)-phenylethyl]amino-4-imidazole (109 mg; 0.25 mmol), vinyltributylstannane (95 mg; 0.3 mmol) and PdCl$_2$(PPh$_3$)$_2$ (17 mg; 0.025 mmol) are dissolved in xylenes (5 ml) and refluxed for 3 h. After filtration and evaporation, the reaction mixture is purified by preparative HPLC on LiChrospher RP-18 (Gilson HPLC-system; column tube: 125 mm×25 mm ID) with MeCN/water as elution system, 40:60 to 100:0 as gradient and a flow rate of 10 ml/min. to yield the title product as white foam (35 mg; 36%).

1H-NMR (400 MHz; DMSO-d6, 120 C): 1.41 (d 3H); 4.88 (m, 1H); 5.19 (dd, 1H); 5.83 (dd, 1H); 6.32 (d, 1H); 6.65 (dd, 1H); 7.13–7.21 (m, 3H); 7.25–7.32 (m, 4H); 7.39 (bd, 1H); 7.47–7.51 (m, 2H); 7.58 (s, 1H); 8.27 (d, 1H).

MS (m/z) ESI: 386.2 (MH+).

Example 35

2-(4-Fluorophenyl)-1-(2-[1-(S)-phenyl-ethyl]amino-4-pyrimidyl) 4-(4-pyridyl)imidazole

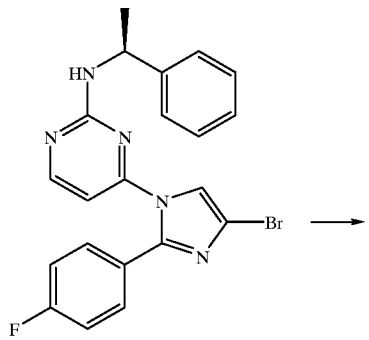

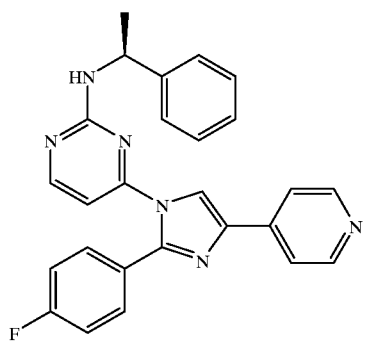

4-Bromo-2-(4-fluorophenyl)-1-(2-[1-(S)-phenylethyl] amino-4-pyrimidyl)imidazole (1.0 g; 2.28 mmol), 4-trimethylstannylpyridine (660 mg; 2.74 mmol) and PdCl$_2$(PPh$_3$)$_2$ (160 mg; 0.228 mmol) are dissolved in xylenes (23 ml) and refluxed for 4 h. The reaction mixture is poured on saturated Na$_2$CO$_3$ solution and extracted with ethyl acetate three times. The combined organic phases were dried over Na$_2$SO$_4$, filtered, evaporated to dryness and purified via SiO$_2$ chromatography (TBME/MeOH/NH$_3$conc 99/9/0.1) to yield the title compound as a yellow foam (780 mg; 68%).

1H-NMR (400 MHz; DMSO-d6): mixture of rotamers, broad signals: 1.30 (bs, 2.1H); 1.45 (bs, 0.9H); 4.45 (bs, 0.7H); 5.18 (bs, 0.3H); 6.48 (0.3H); 6.56 (bs, 0.7H); 7.20 (bd, 2H); 7.26–7.32 (m, 5H); 7.53 (bs, 2H); 7.32 (bs, 2H); 8.15 (d, 1H); 8.40 (bs, 2H); 8.60 (d, 2H).

MS (m/z) EI: 436 (M+, 100); 421 (95);

The compounds of Examples 36 to 39 and the precursor a) of Example 40 are similarly prepared by coupling 4-Bromo-2-(4-fluorophenyl)-1-(2-[1-(S)-phenylethyl]amino-4-pyrimidyl)imidazole with heteroarylstannanes as described above:

Example 36

2-(4-Fluorophenyl)-1-(2-[1-(S)-phenyl-ethyl]amino-4-pyrimidyl) 4-(2-pyridyl)imidazole 1H-NMR (400 MHz; DMSO-d6, mixture of rotamers at room temperature): 1.25–1.36 (bd, 3H); 4.45 (bs, 1H); 6.62 (bs, 1H); 7.15–7.32 (m, 8H); 7.55 (bs, 2H); 7.86 (dt, 1H); 7.98 (d, 1H); 8.07 (d, 1H); 8.20 (bs, 1H); 8.35 (bs, 1H); 8.58 (d, 1H).

MS (m/z) EI: 436 (M+, 100); 421 (60); 240 (20); 225 (40); 211 (30); 105 (30).

Example 37

2(4-Fluorophenyl)-1-(2-[1-(S)-phenyl-ethyl]amino-4-pyrimidyl) 4-(3-pyridyl)imidazole 1H-NMR (400 MHz; DMSO-d6, 120° C.): 1.48 (d, 3H); 4.88 (m, 1H); 6.42 (d, 1H); 7.19 (t, 3H); 7.23–7.33 (m, 4H); 7.41 (m, 2H); 7.50–7.53 (m, 2H); 8.08 (s, 1H); 8.16 (dd, 1H); 8.31 (d, 1H); 8.48 (dd, 1H); 9.06 (d, 1H).

MS (m/z) EI: 436 (M+, 90); 421 (60).

Example 38

2-(4-Fluorophenyl)-1-2-[1-(S)-phenyl-ethyl]amino-4-pyrimidyl) 4-(2-thienyl)imidazole 1H-NMR (400 MHz; DMSO-d6, 120° C.): 1.45 (d, 3H); 4.89 (m, 1H); 6.38 (d, 1H); 7.10 (dd, 1H); 7.20 (m, 3H); 7.28–7.36 (m, 3H); 7.38–7.48 (m, 3H); 7.50–7.55 (m, 2H); 7.82 (s, 1H); 8.30 (d, 1H).

MS (m/z) ESI: 442 (MH+, 100).

Example 39

2-(4-Fluorophenyl)-1-(2-[1-(S)-phenyl-ethyl]amino-4-pyrimidyl) 4-(2-furyl)imidazole 1H-NMR (400 MHz; DMSO-d6, 120° C.): 1.42 (d, 3H); 4.90 (m, 1H); 6.40 (d, 1H); 6.52 (s, dd 1H); 6.68 (d, 1H); 7.20 (t, 3H); 7.25–7.35 (m, 4H); 7.52 (m, 2H); 7.61 (d, 1H); 7.78 (s, 1H); 8.30 (d, 1H).

MS (m/z) ESI: 426 (MH+, 100).

Example 40

2-(4-Fluorophenyl)-1-(2-[1-(S)-phenyl-ethyl]amino-4-pyrimidyl) 4-(2-amino)pyrimidylimidazole
a) 2-(4-Fluorophenyl)-1-(2-[1-(S)-phenyl-ethyl]amino-4-pyrimidyl) 4-(2-methylthio) pyrimidylimidazole
b) 2-(4-Fluorophenyl)-1-(2-[1-(S)-phenyl-ethyl]amino-4-pyrimidyl) 4-(2-methylsulfinyl)pyrimidylimidazole

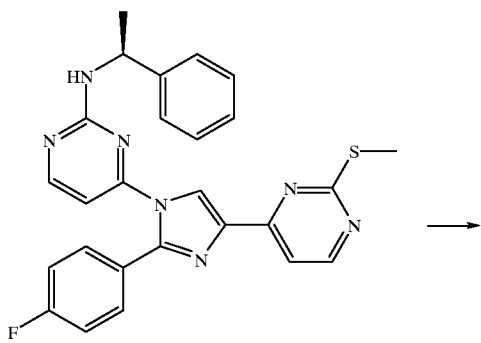

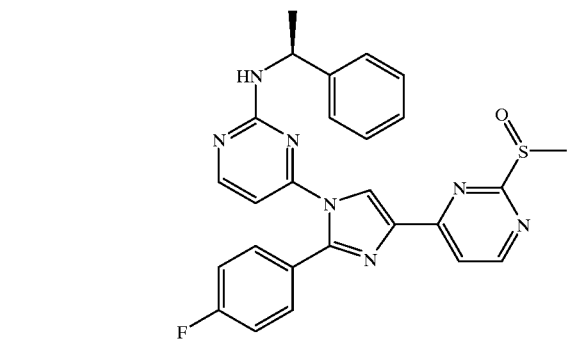

2-(4-Fluorophenyl)-1-(2-[1-(S)-phenyl-ethyl]amino-4-pyrimidyl) 4-(2-methylthio)pyrimidylimidazole (483 mg; 1 mmol) is dissolved in methylene chloride (24 ml) and treated at 0 C with mCPBA (70% in water, 286 mg; 1.4 mmol) in methylene chloride (2.9 ml). After 30 min at 0 C the reaction mixture is poured on 2N Na$_2$CO$_3$ and extracted with methylene chloride three times. The combined or phases are dried over Na$_2$SO$_4$, filtered and evaporated to yielding the sulfoxide as a pale yellow foam (530 mg), which is used without further purification.

c) 2-(4-Fluorophenyl)-1-(2-[1-(S)-phenyl-ethyl]amino-4-pyrimidyl) 4-(2-amino)pyrimidylimidazole

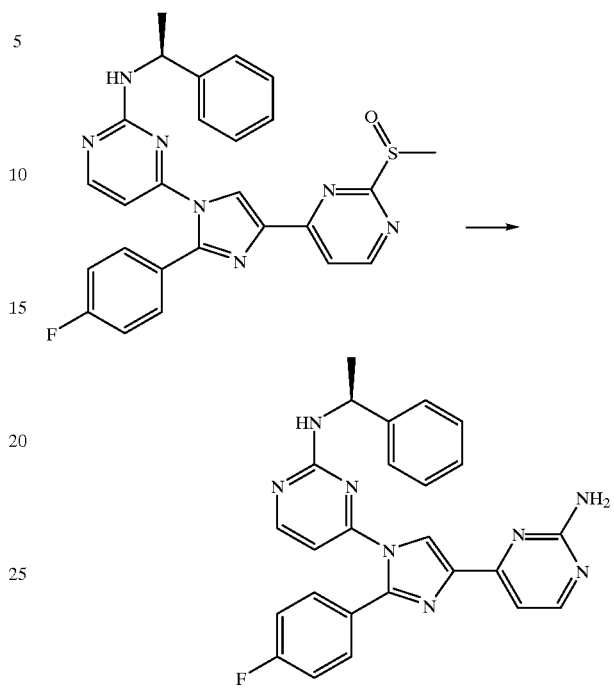

2-(4-Fluorophenyl)-1-(2-[1-(S)-phenyl-ethyl]amino-4-pyrimidyl) 4-(2-methylsulfinyl) pyrimidylimidazole (50 mg; 0.1 mmol) is transferred into a steel cylinder, dissolved in THF (10 ml), cooled to −78 C and saturated with NH$_3$. The reaction mixture is heated to 80 C for 3 h and gives after evaporation of the solvent and purification by preparative HPLC on LiChrospher RP-18 (Gilson HPLC-system: column tube: 125 mm×25 mm ID) with MeCN/water as elution system, 40:60 to 100:0 as gradient and a flow rate of 10 ml/min the title product as colorless crystals (13 mg, 31%).

MS (m/z) EI: 453 (30); 452 (M+, 100); 437 (70).

Example 41

2-(4-Fluorophenyl)-1-(2-[1-(S)-phenyl-ethyl]amino-4-pyrimidyl) 4-(2-hydroxy)pyrimidylimidazole

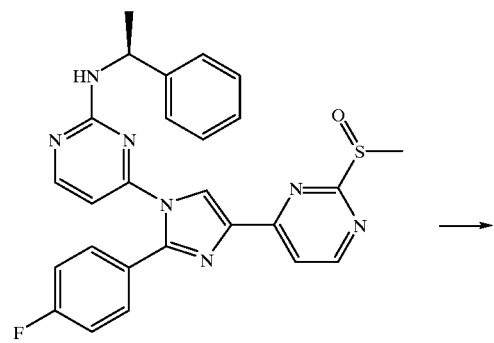

-continued

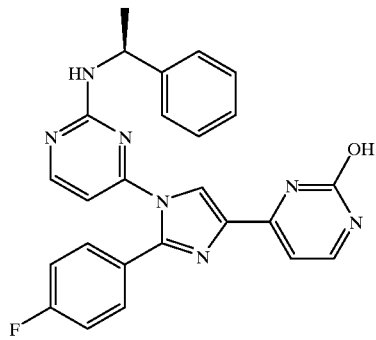

The sulfoxide (50 mg; 0.1 mmol) is dissolved in dioxan/water (5 ml 5/1) and tretaed 3 N KOH (0.1 ml) for 1 h at room temperature. The reaction mixture is acidified with 2 N HCl and extracted twice with ethyl acetate. The combined organic phases are dried over Na$_2$SO$_4$, filtered, evaporated to dryness and purified by preparative HPLC on LiChrospher RP-18 (Gilson HPLC-system; column tube: 125 mm×25 mm ID) with MeCN/water as elution system, 40:60 to 100:0 as gradient and a flow rate of 10 ml/min to yield the title product as colorless crystals (20 mg, 44%).

1H-NMR (400 MHz; DMSO-d6, 120 C): 1.44 (s, 3H); 4.85–4.92 (m, 1H); 6.48 (d, 1H); 6.97 (d, 1H); 7.17–7.23 (m, 3H); 7.28–7.35 (m, 4H); 7.48–7.58 (m, 3H); 7.96 (bd, 1H, NH); 8.33 (d, 2H).

MS (m/z) EI: 453 (M+, 100); 438 (75).

Example 42

2-(4-Fluorophenyl)-1-(2-[1-(S)-phenyl-ethyl]amino-4-pyrimidyl) 4-(2-N-morpholinyl)pyrimidylimidazole

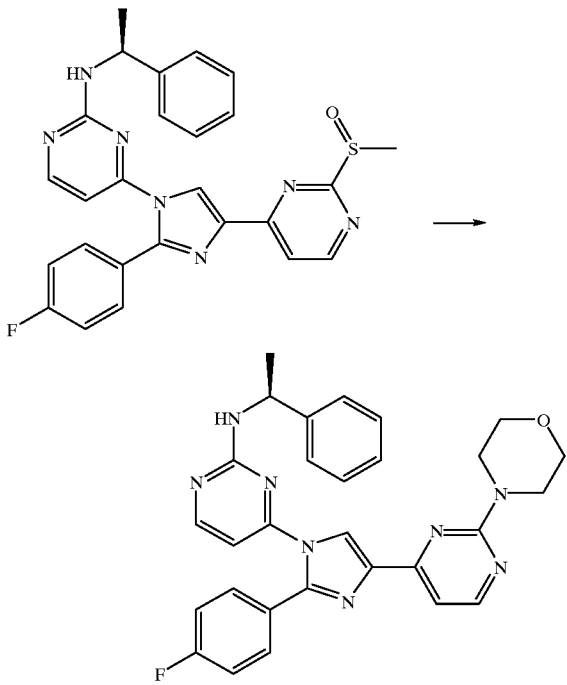

2-(4-Fluorophenyl)-1-(2-[1-(S)-phenyl-ethyl]amino-4-pyrimidyl) 4-(2-methylsulfinyl)pyrimidylimidazole (50 mg; 0.1 mmol) and morpholine (0.5 ml) are heated at 80 C for 30 mm. The reaction mixture is evaporated to dryness and purified by preparative HPLC on LiChrospher RP-18 (Gilson HPLC-system; column tube: 125 mm×25 mm ID) with MeCN/water as elution system, 40:60 to 100:0 as gradient and a flow rate of 10 ml/min to yield the title product as colorless crystals (25 mg; 48%).

1H-NMR (400 MHz; DMSO-d6): mixture of rotamers, broad signals: 1.31 (bs, 2.1H); 1.45 (bs, 0.9H); 3.72 bs, 4H); 3.80 (bs, 4H); 4.48 (bs, 0.7H); 5.18 (bs, 0.3H); 6.29 (bs, 0.3H); 6.57 (bs, 0.7H); 7.13–7.43 (m, 8H); 7.50 (bs, 2H); 8.15 (d, 1H); 8.19–8.42 (m, 2H); 8.43 (d, 1H).

MS (m/z) EI: 522 (M+, 100); 492 (70); 491 (70); 477 (60); 465 (50); 105 (20).

Example 43

2-(4-Fluorophenyl)-1-(2-[1-(S)-phenyl-ethyl]amino-4-pyrimidyl)-4-(3-thienyl)imidazole

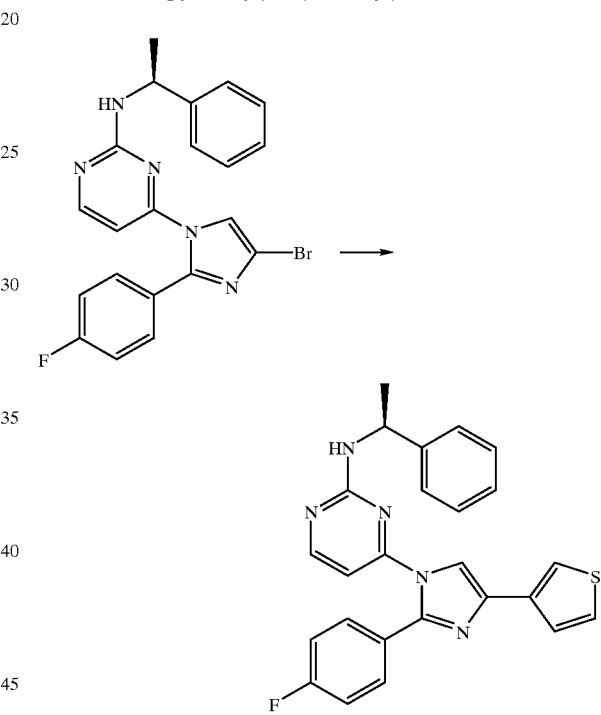

4-Bromo-2-(4-fluorophenyl)-1-(2-[1-(S)-phenylethyl]amino-4-pyrimidyl)imidazole (109 mg, 0.25 mmol), thiophene-3-boronic acid (35 mg; 0.27 mmol) and Pd(PPh3)4 (14 mg, 0.0125 mmol) are dissolved in dioxane (1.25 ml) and saturated Na$_2$CO$_3$ solution (0.33 ml, 0.5 mmol) and heated to 80 C for 18 h. The reaction mixture is poured on saturated Na$_2$CO$_3$ solution and extracted with ethyl acetate three times. The combined organic phases are dried over Na$_2$SO$_4$, filtered and evaporated and purified via preparative HPLC on LiChrospher RP-18 (Gilson HPLC-system; column tube: 125 mm×25 mm ID) with MeCN/water as elution system, 40:60 to 100:0 as gradient and a flow rate of 10 ml/min to yield the title product as colorless crystals (62 mg, 60%).

1H-NMR (400 MHz; DMSO-d6, 120 C): 1.41 (d, 3H); 4.82–4.93 (m, 1H); 6.40 (d, 1H); 7.16–7.22 (m, 3H), 7.26–7.35(m, 4H); 7.40 (d, 1H, NH); 7.50–7.58 (m, 4H); 7.71 (d, 1H); 7.84 (s, 1H); 8.30 (d, 1H).

MS (m/z) EI: 441 (M+, 100); 426 (40).

The following compounds of Examples 44 to 49 are similarly prepared by coupling 4-bromo-2-(4-fluorophenyl)-(2-[1-(S)-phenylethyl]amino-4-pyrimidyl)imidazole with aryl and heteroaryl boronic acids:

Example 44

2-(4-Fluorophenyl)-1-(2-[1-(S)-phenyl-ethyl]amino-4-pyrimidyl)-4-(2-benzofuryl)imidazole

Example 45

2-(4-Fluorophenyl)-1-(2-[1-(S)-phenyl-ethyl]amino-4-pyrimidyl)-4-(5-chlorothien-2-yl)imidazole

Example 46

2-(4-Fluorophenyl)-1-(2-[1-(S)-phenyl-ethyl]amino-4-pyrimidyl)-4-(4-methoxyphenyl)imidazole

Example 47

2-(4-Fluorophenyl)-1-(2-[1-(S)-phenyl-ethyl]amino-4-pyrimidyl)-4-(4-fluorophenyl)imidazole

Example 48

2-(4-Fluorophenyl)-1-(2-[1-(S)-phenyl-ethyl]amino-4-pyrimidyl)-4-(3-chloro-4-fluorophenyl)imidazole

Example 49

2-(4-Fluorophenyl)-1-(2-[1-(S)-phenyl-ethyl]amino-4-pyrimidyl)-4-(3-chloro phenyl)imidazole
(AAL395)

Example 50

2-(4-Fluorophenyl)-1-(2-[1-(S)-phenyl-ethyl]amino-4-pyrimidyl)-4-methyleneaminoguanidinyl-imidazole a) 2-(4-Fluorophenyl)-1-(2-[1-(S)-phenyl-ethyl]amino-4-pyrimidyl)-4-(3-formyl)-imidazole

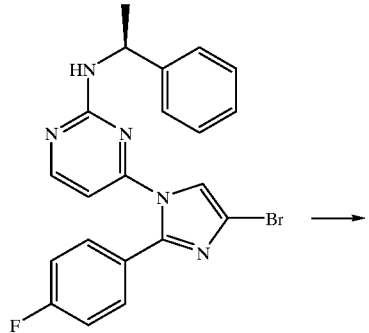

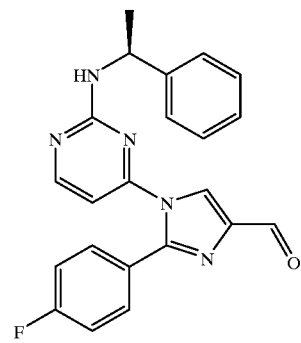

4-Bromo-2-(4-fluorophenyl)-1-(2-[1-(S)-phenylethyl] amino-4-pyrimidyl)imidazole (200 mg; 0.45 mmol) is dissolved in THF (2.8 ml), cooled to −78 C and treated with nBuLi (0.57 ml of a 1.6 M solution in hexane; 0.9 mmol) for 10 min. Dimethylformamide (0.039 ml; 0.5 mmol0 is added and stirred for 10 min. The reaction mixture is poured on saturated NaCl solution and extracted with TBME three times. The combined organic phases are dried over $Na_2SO_4$, filtered and evaporated and purified via preparative HPLC on LiChrospher RP-18 (Gilson HPLC-system; column tube: 125 mm×25 mm ID) with MeCN/water as elution system, 40:60 to 100:0 as gradient and a flow rate of 10 ml/min to yield the title product as white foam (36 mg; 20%).

1H-NMR (400 MHz; DMSO-d6): mixture of rotamers, broad signals: 1.30 (bs, 2.1H); 1.45 (bs, 0.9H); 4.45 (bs. 0.7H); 5.15 (bs, 0.3H); 6.45 (bs, 0.3H); 6.58 (bs, 0.7H); 7.12–7.21 (bd, 2H); 7.24–7.40 (m, 4H); 7.50 (bs, 2H); 8.18 (bd, 1H); 8.4 (bd, 1H, NH), 9.88 (s, 1H).

MS (m/z) EI: 387 (M+, 100); 372 (85), 105 (25).

b) 2-(4-Fluorophenyl)-1-(2-[1-(S)-phenyl-ethyl]amino-4-pyrimidyl)-4-methyleneaminoguanidinyl-imidazole

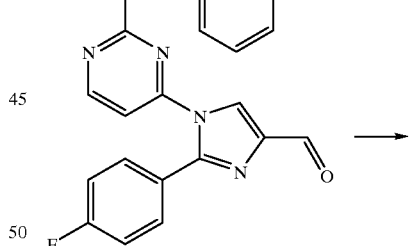

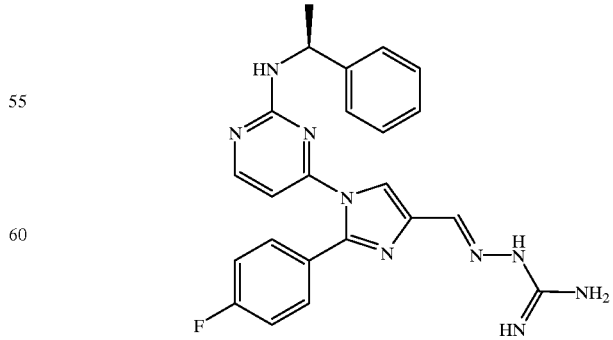

2-(4-Fluorophenyl)-1-(2-[1-(S)-phenylethyl]amino-4-pyrimidyl)-4-(3-formyl)imidazole (26 mg, 0.068 mmol) is dissolved in EtOH (0.5 ml) and 5.5 N HCl in isopropanol (0.5 ml) and treated with aminoguanidine-hydrogencarbonate (18.5 mg, 0.13 mmol). The reaction mixture is diluted with MeOH (1.5 ml) and left at room temperature over night and is poured on saturated Na₂CO₃ solution and extracted with ethyl acetate three times. The combined organic phases are dried over Na₂SO₄, filtered and evaporated and purified via SiO₂ chromatography (TBME/MeOH/NH₃conc 80/20/2) to yield the title compound as white crystals (7 mg; 23%).

MS (m/z) EI: 443 (M+, 100); 246 (50); 105 (65).

Example 51

2-(4-Fluorophenyl)-1-(2-(1-(S)-phenylethyl)amino-4-pyrimidyl)-4-(4-ethoxycarbonyl)piperidine-1-yl Imidazole a) 4-(4-Ethoxycarbonyl-1-hydroxypiperidine-1-yl)-2-(4-fluorophenyl)-1-(2-(trimethylsilyl) Ethoxymethylimidazole

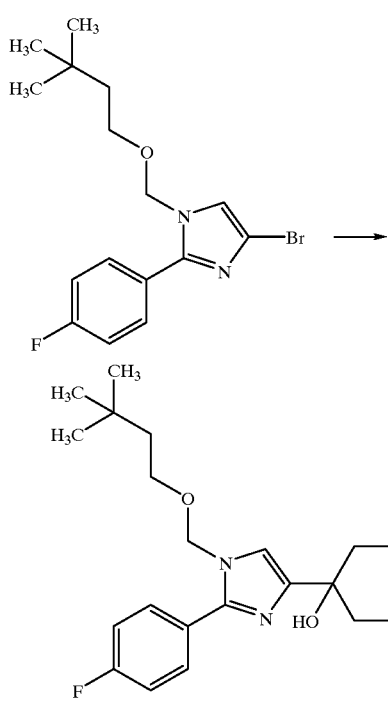

nBuLi (8.25 ml of a 1.6 M solution in hexane; 13.2 mmol) is added under argon within 10 min to a precooled and stirred solution (−78 C) of 4-bromo-2-(4-fluorophenyl-(2-(trimethylsilyl) ethoxy-methyl)imidazole (4.45 g; 12 mmol) in THF (50 ml). Stirring is continued for 15 min at −78 C. N-Ethoxycarbonyl-4-piperidone (2.35 ml, 15.6 mmol) is introduced within 2 min. After 30 min at −78 C, the reaction is warmed to 0 C within 30 min, poured on ice-water and extracted three times with ethyl acetate. The combined organic phase are washed with a saturated solution of NaCl, dried over Na₂SO₄, filtered and evaporated to dryness. Purification over SiO₂ (cyclohexane/acetone 99/1 to 92/8) yields the title compound (2.5 g; 45%) as colorless foam.

NMR: −0.03 (s, 9H); 0.86 (t, 2H); 1.19 (t, 3H); 1.66 (bd, 2H); 1.88–1.97 (m, 2H); 3.19–3.37 (bd, 2H); 3.58 (t, 2H); 3.72 (bd, 2H); 4.05 (q, 2H); 4.95 (s, 1H, OH); 5.31 (s, 2H); 7.30 (s, 1H); 7.32 (t, 2H); 7.80 (dd, 2H).

MS (m/z): 463 (M+, 60); 435 (45); 335 (70); 277 (70); 189 (40); 73 (100).

b) 4-(4-Ethoxycarbonyl-1-hydroxypiperidine-1-yl)-2-(4-fluorophenyl)-1H-imidazole

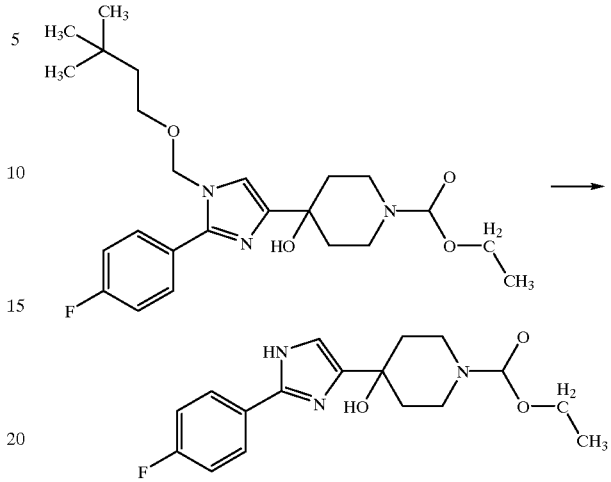

2-(4-Fluorophenyl)-1-(2-(trimethylsilyl)ethoxymethyl)-4-(4-ethoxycarbonyl-1-hydroxypiperidine-1-yl)imidazole (13.2 g; 28.6 mmol) dissolved in EtOH/HClconc (1:1; 290 ml) is heated at 50 C for 1 h, poured on 2N NH₄OH and extracted three times with ethyl acetate. The combined organic phases are washed with a saturated solution of NaCl, dried over Na₂SO₄, filtered and evaporated to dryness to yield the title compound (11 g), which after recrystallization from TBME gave the product in high purity (4.7 g; 49%).

1H-NMR (400 MHz; DMSO-d6): Tautomeric mixture. 1.21 (t, 3H); 1.68 (bd, 2H); 1.80–1.98 (m, 2H); 3.27 (bs, 2H); 3.69–3.83 (m, 2H); 4.06 (q, 2H); 4.85 (s, 1H, OH); 7.09 (s, 1H); 7.28 (dd, 2H); 7.93 (dd, 1.2H); 8.02 (dd, 0.8H); 12.20 (s, 0.6H, NH); 12.30 (s, 0.4H, NH).

MS (m/z; ESI): 334.2 (MH+, 100).

c) 4-(Ethoxycarbonylpiperid-1-ene-1-yl)-2-(4-fluorophenyl)-1H-imidazole

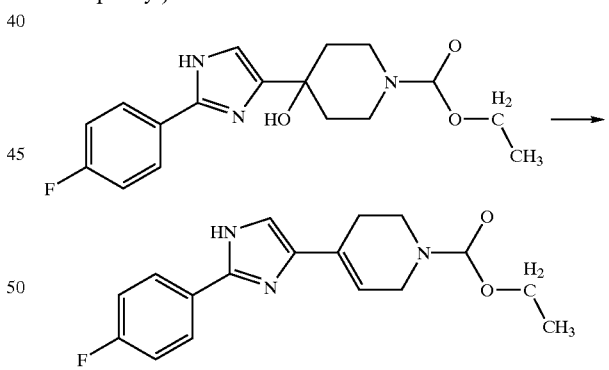

4-(4-Ethoxycarbonyl)-1-hydroxypiperidine-1-yl-2-(4-fluorophenyl-1H-imidazole (4.6 g, 13.8 mmol), imidazole (1.13 g; 16.56 mmol), tert.-butyldimethylchlorsilane (2.5 g; 16.56 mmol) are dissolved in DMF (70 ml) and heated at 70 C for 24 h. The reaction mixture is evaporated, water added and the aqueous phase extracted with ethyl acetate three times. The combined organic phases are washed with a saturated solution of NaCl, dried over Na₂SO₄ filtered and evaporated to dryness to yield the crystalline product, which is purified by recrystallization from TBME and gives the title compound in high purity (3.1 g; 71%).

1H-NMR (400 MHz; DMSO-d6): NMR: mixture of tautomers. 1.21 (t, 3H); 2.41 (bs, 2H); 3.60 (bt, 2H); 4.05 (bt, 2H); 4.10 (q, 2H); 6.24 (bs, 0.3H); 6.32 (bs, 0.7H); 7.30 (dd, 2H); 7.98 (dd, 1.4M); 8.05 (dd, 0.6H).

MS (m/z; EI): 315 (M+, 65); 286 (100); 242 (45).

d) 4-(4-Ethoxycarbonylpiperidine-1-yl)-2-(4-fluorophenyl)-1H-imidazole

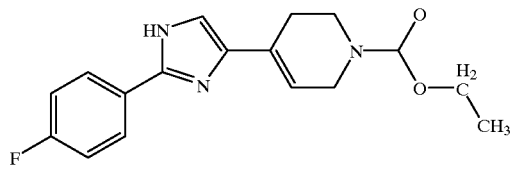

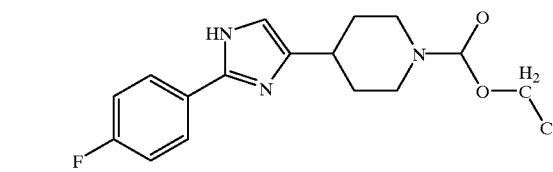

4-(4-Ethoxycarbonylpiperid-1-ene-1-yl-2-(4-fluorophenyl)-1H-imidazole (3.7 g; 11.7 mmol) and 10% Pd/C (0.9 g) are dissolved in acetic acid (117 ml) and hydrogenated until hydrogen uptake is complete (1 h). The reaction mixture is evaporated, 2N NH$_4$OH added and the aqueous phase extracted with ethyl acetate three times. The combined organic phases are washed with a saturated solution of NaCl, dried over Na$_2$SO$_4$, filtered and evaporated to dryness to yield the crystalline product (3.5 g; 96%), which is used without further purification.

1H-NMR (400 MHz; DMSO-d6): NMR: mixture of tautomers. 1.16–1.23 (m, 3H); 1.40–1.60 (m, 2H); 1.88–1.98 (m, 2H); 2.66–2.75 (m, 1H); 2.80–3.00 (m, 2H); 3.98–4.10 (m, 4H); 6.72 (s, 0.4H); 6.96 (s, 0.6H); 7.23–7.30 (m, 2H); 7.90–7.97 (m, 2H), 12.20 (s, 0.4H); 12.25 (s, 0.6H).

MS (m/z; EI): 317 (M+, 20); 244 (20); 189 (100).

e) 4-(4-Ethoxycarbonylpiperidine-1-yl)-2-(4-fluorophenyl)-1-((2-methylthio)-4-pyrimidyl)imidazole

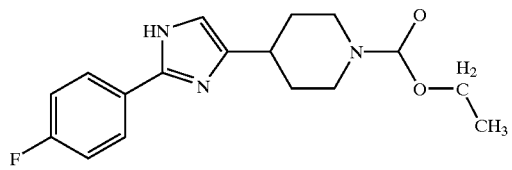

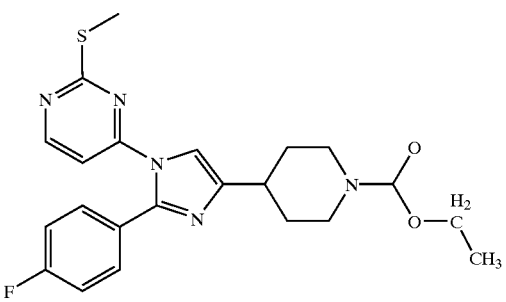

4-(4-Ethoxycarbonylpiperidine-1-yl-2-(4-fluorophenyl)-1H-imidazole (2.65 g; 8.4 mmol) is dissolved in DMF (53 ml) and cooled to 0 C. KN(TMS)2 (1.68 g; 9.24 mmol) in toluene (18.5 ml) is added at 0–10 C within 10 min and stirred for 30 min. 4-Chloro-2-methylthiopyrimidine (1.48 g; 9.24 mmol) in DMF (9 ml) is added at 10 C with 10 min and the reaction mixture stirred at room temperature for 1 h, then at 75 C for 18 h, poured on water and extracted three times with ethyl acetate. The combined organic phases are washed with a saturated solution of NaCl, dried over Na$_2$SO$_4$, filtered and evaporated to dryness. Purification over SiO$_2$ (acetone/cyclohexane 1/9 to 3/7) yields the title compound as a yellow foam (2.6 g; 70%).

1H-NMR (400 MHz; DMSO-d6, 120C): 1.20 (t, 3H); 1.46–1.59 (dq, 2H); 1.95–2.03 (bd, 2H); 2.13 (s, 3H); 2.72–2.82 (tt, 1H); 2.86–3.03 (bs, 2H); 4.06 (q, 2H); 7.11 (d, 1H); 7.24 (t, 2H); 7.46 (dd, 2H); 7.63 (s, 1H); 8.68 (d, 1H).

MS (m/z; EI): 441 (30); 368 (20); 313 (100).

f) 4-(4-Ethoxycarbonylpiperidine-1-yl)-2-(4-fluorophenyl)-1-(2-methylsulfinyl)-4-pyrimidyl)imidazole

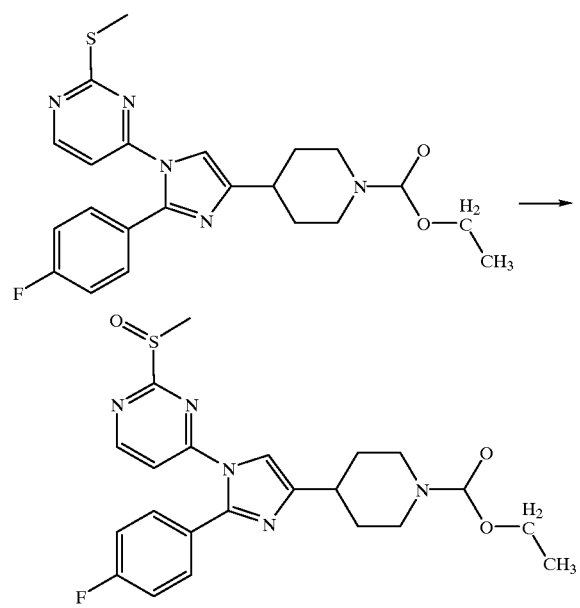

4-(4-Ethoxycarbonylpiperidine-1-yl)-2-(4-fluorophenyl)-1-((2-methylthio)-4-pyrimidyl)imidazole (4.2 g; 9.52 mmol) is dissolved in methylene chloride (95 ml) and cooled to 0 C. mCPBA (70% in water, 2.6 g, 12.85 mmol) dissolved in methylene chloride (26 ml) is added within 15 min and the reaction mixture stirred for 15 min at 0 C. 2N Na$_2$CO$_3$ (100 ml) is added and extracted three times with methylene chloride. The combined organic phases are washed with a saturated solution of NaCl, dried over Na$_2$SO$_4$, filtered and evaporated to dryness to yield the title compound (4.3 g, 98%) which is used without further purification.

g) 2-(4-Fluorophenyl)-1-(2-(1-(S)-phenylethyl)amino-4-pyrimidyl)-4-(4-ethoxycarbonyl)piperidine-1-yl Imidazole

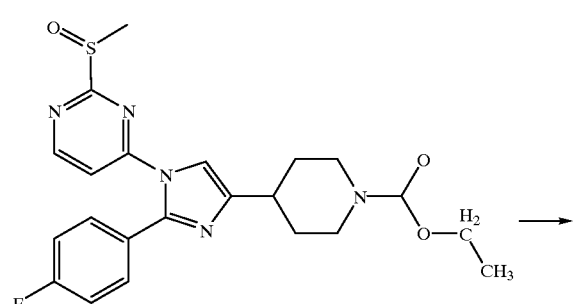

-continued

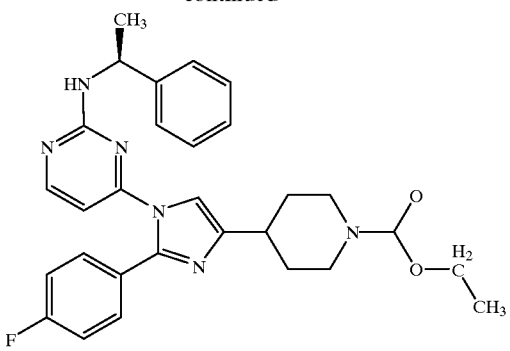

4-(4-Ethoxycarbonylpiperidine-1-yl)-2-(4-fluorophenyl)-1-((2-methylsulfinyl)-4-pyrimidyl)imidazole (4.3 g; 9.52 mmol) and 1-(S)-phenylethylamine (4.3 ml) are heated at 120 C for 1 h, evaporated to dryness and purified via SiO$_2$ chromatography (acetone/cyclohexane 1/9 to 2/8) to yield the title compound as colorless foam (4.4 g; 90%).

1H-NMR (400 MHz; DMSO-d6) mixturs of rotamers. 1.19 (t, 3H); 1.3 (bd, 3H); 1.40–1.54 (bq, 2H); 1.93–2.01 (bd, 2H); 2.68–2.80 (bt, 1H); 2.96–3.03 (bs, 2H); 4.00–4.10 (m, 4H); 4.43 (bs, 0.7H); 5.13 (bs, 0.3H); 6.20 (bs, 0.3H); 6.48 (bs, 0.7H); 7.13–7.47 (m, 10H); 8.00 (d, 1H); 8.28 (bs, 1H, NH).

MS (m/z; ESI): 515.3 (M+, 100).

Example 52

2-(4-Fluorophenyl)-1-(2-(1-(S)-phenylethyl)amino-4-pyrimidyl)-4-piperidine-1-yl Imidazole

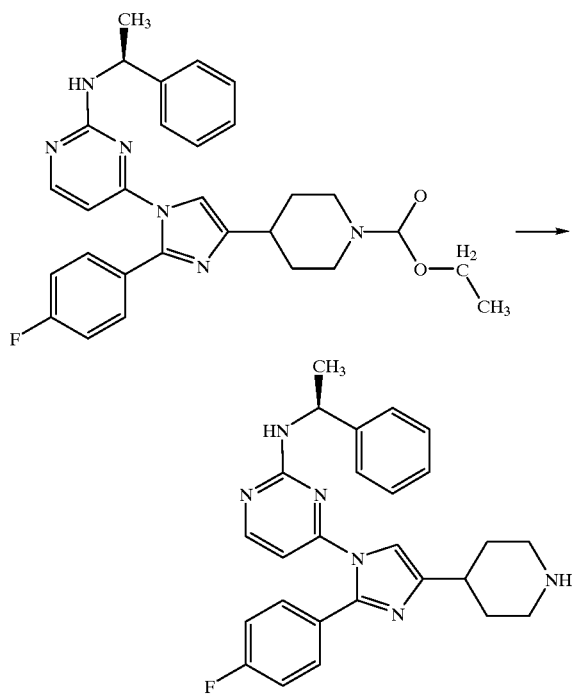

2-(4-Fluorophenyl-1-(2-(1-(S)-phenylethyl)amino-4-pyrimidyl)-4-(4-ethoxycarbonyl)piperidine-1-yl imidazole (4.4 g, 856 mmol) and trimethylsilyliodide (4.4 ml; 32.3 mmol) are dissolved in CHCl$_3$ (85 ml) and heated at 60 C for 3 h. After cooling to room temperature, the reaction mixture is acidified with 6M HCl (35 ml) and the water phase washed twice with TBME. The combined aqueous phases are treated with a saturated solution of Na$_2$CO$_3$ and extracted twice with methylene chloride. The combined organic phases are washed with a saturated solution of NaCl, dried over Na$_2$SO$_4$, filtered and evaporated to dryness. Purification over SiO$_2$ (TBME/MeOH/NH$_3$conc 90/9/1 to 79/27/3) yields the title compound as a white foam (3.1 g; 82%).

1H-NMR (400 MHz; DMSO-d6, 120 C): 1.41 (d, 3H); 1.69–1.82 (dq, 2H); 2.08 (bd, 2H); 2.71–2.81 (bt, 1H); 2.87 (t, 2H); 3.26 (bd, 2H); 4.30–4.40 (m, 1H); 6.30 (d, 1H); 7.10–7.48 (m, 10H); 8.23 (d, 1H).

MS (m/z; ESI): 443.2 (MH+).

Example 53

2-(4-Fluorophenyl)-1-(2-(1-(S)-phenylethyl)amino-4-pyrimidyl)-4-(4-formyl)-piperidine-1-yl Imidazole

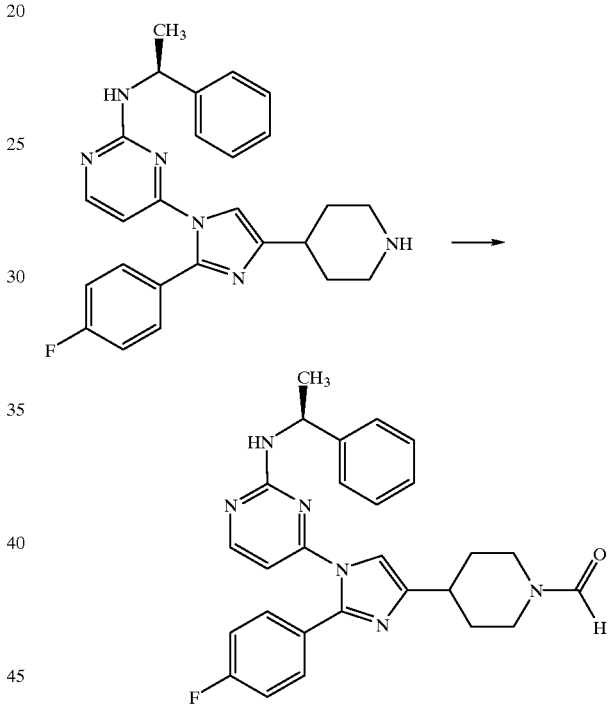

Imidazole (16.2 mg; 0.237 mmol) is dissolved in DMF (0.021 ml; 0.277 mmol) and treated with Me$_3$SiCl (0.03 ml; 0.237 mmol) for 20 min at room temperature. 2-(4-Fluorophenyl)-1-(2-(1-(S)-phenylethyl)amino-4-pyrimidyl)-4-piperidine-1-yl imidazole (35 mg; 0.079 mmol) is dissolved in DMF (0.025 ml) and added to the preformed formylation reagent and stirred at room temperature for 24 h. The reaction mixture is poured on a saturated Na$_2$CO$_3$ solution and extracted three tines with TBME. The combined organic phases are washed with a saturated solution of NaCl, dried over Na$_2$SO$_4$, filtered and evaporated to dryness.

1H-NMR (400 MHz; DMSO-d6): mixture of rotamers. 1.24–1.58 (m, 5H); 1.97–2.10 (bt, 2H); 2.79 (dt, 1H); 285 (bt, 1H); 3.18 (dt, 1H); 3.75 (bd, 1H); 4.21 (bd, 1H); 4.45 (bs, 0.7H); 5.15 (bs, 0.3H); 6.20 (bs, 0.3H); 6.40 (bs, 0.7H); 7.15–7.32 (m, 8H); 7.42 (bt, 2H); 8.01 (d, 1H); 8.05 (s, 1H); 8.28 (bs, 1H).

MS (m/z; ESI): 471.2 (MH+).

Example 54

2-(4-Fluorophenyl)-1-(2-(1-(S)-phenylethyl)amino-4-pyrimidyl)-4-(4-(2-hydroxy-2-methyl)propylpiperidine-1-yl Imidazole

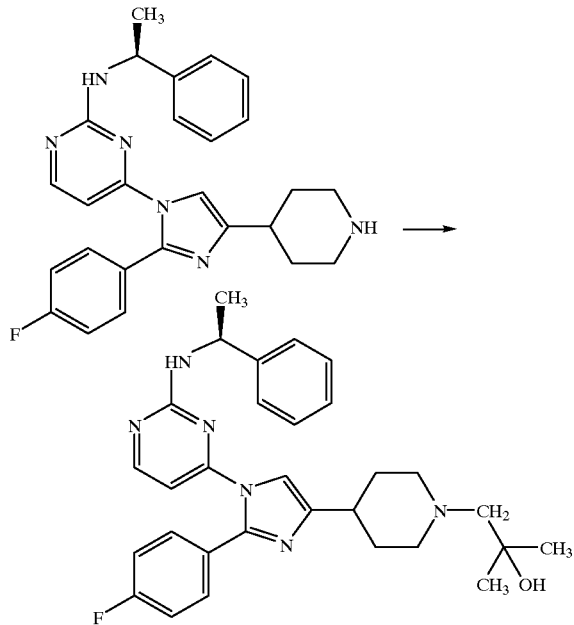

2-(4-Fluorophenyl)-1-(2-(1-(S)-phenylethyl)amino-4-pyrimidyl)-4-piperidine-1-yl imidazole (35 mg; 0.079 mmol) is dissolved in EtOH (0.5 ml) and heated with isobutylene oxide (0.023 ml; 0.31 mmol) at 90 C for 3 h. The reaction mixture is evaporated to dryness and purified via SiO$_2$ chromatography (TBME/MeOH/NH$_3$conc 97/3/0.3 to 96/4/0.4) to yield the title compound as a yellow foam (34 mg; 83%).

1H-NMR (400 MHz; DMSO-d6) mixture of rotamers. 1.10 (s, 3H); 1.11 (s, 3H); 1.22–1.34 (m, 3H): 1.57–1.71 (m, 2H); 1.83–1.92 (bd, 2H); 2.22 (m, 4H); 3.00 (bd, 2H); 2.43–2.52 (bt, 1H); 4.05 (s, 1H, OH); 4.45 (bs, 1H); 6.18 (bs, 0.3H); 6.40 (bs, 0.7H); 7.13–7.32 (m, 8H); 7.43 (bt, 2H); 8.00 (d, 1H, NH); 8.28 (bs, 1H).

MS (m/z; ESI): 515.3 (MH+, 100); 258 (80).

Example 55

2-(4-Fluorophenyl)-1-(2-cyclopentyl)amino-4-pyrimidyl)-4-(2-hydroxy-2-methyl)propylpiperidine-1-yl Imidazole

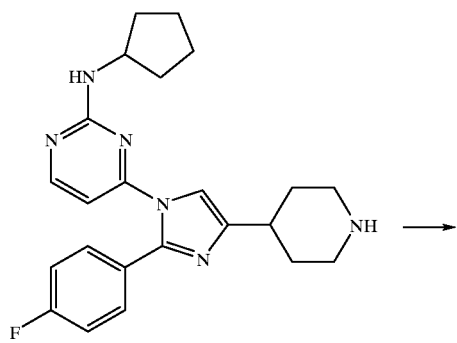

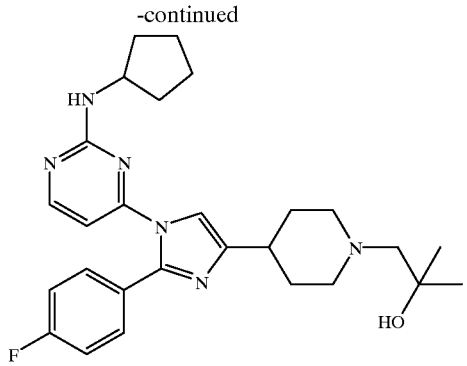

The title compound is prepared according to the procedures described above and is obtained as colorless crystals in 73% yield.

1H-NMR (400 MHz; DMSO-d6, 180° C.): 1.28 (s, 6H); 1.40–1.60 (m, 4H); 1.66–1.76 (m, 2H), 1.80–1.91 (m, 2H); 1.95–2.20 (m, 4H); 2.55–3.00 (m, 5H); 3.30–3.40 (m, 2H); 3.95–4.05 (m, 1H); 6.33 (d, 1H); 7.11 (dd, 2H); 7.35 (s, 1H); 7.48 (dd, 2H); 8.25 (d, 1H).

MS (m/z; ESI): 479 (MH+, 60); 240 (100); 231 (80).

Example 56

2-(4-Fluorophenyl)-1-(2-(1-(S)-phenylethyl)amino-4-pyrimidyl)-4-(4-methyl)-piperidine-1-yl Imidazole

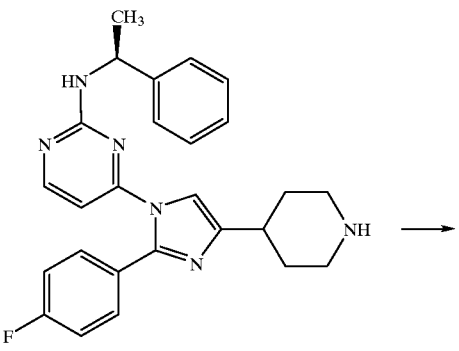

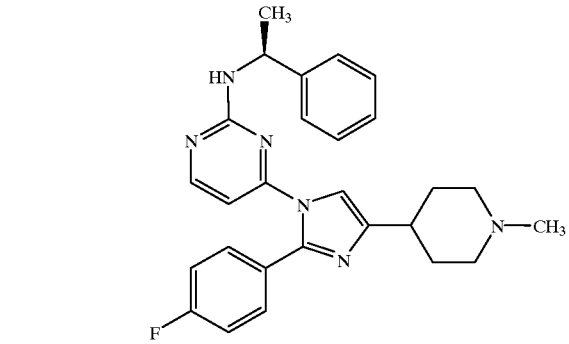

2-(4-Fluorophenyl)-1-(2-(1-(S)-phenylethyl)amino-pyrimidyl)-4-piperidine-1-yl imidazole (35 mg; 0.079 mmol) in acetonitrile (0.5 ml) and formaldehyde (35% in water; 0.010 ml; 0.126 mmol) are treated with NaCNBH$_3$ (6 mg; 0.095 mmol). After stirring for 5 min, HOAc (0.0045 ml; 0.079 mmol) is added and stirring continued for 2 h at room temperature. The reaction mixture is poured on 1N HCl and washed with TBME. The aqueous phase is treated with a saturated solution of Na$_2$CO$_3$ until the pH becomes basic and extracted three times with TBME. The combined organic phases are washed with a saturated solution of NaCl, dried over Na$_2$SO$_4$, filtered and evaporated to dryness. Purification over SiO$_2$ (TBME/MeOH/NH$_3$conc 90/9/1) yields the title compound as a white foam (14.6 mg, 40%).

1H-NMR (400 MHz; DMSO-d6, 120 C): 1.41 (d, 3H); 1.62–1.74 (dq, 2H); 1.92–2.00 (bd, 2H); 2.12–2.10 (dt, 2H); 2.21 (s, 3H); 2.43–2.52 (bt, 1H); 2.79–2.90 (m, 2H); 4.82–4.91 (m, 1H); 6.29 (d, 1H); 7.11–7.48 (m, 8H); 7.45 (dd, 2H) 8.23 (d, 1H).

MS (m/z; ESI): 457.2 (MH+, 75); 229.2 (100).

Example 57

2-(4-Fluorophenyl)-1-(2-(1-(S)-phenylethyl)amino-4-pyrimidyl)-4-(1-hydroxy-4-tert.butyloxycarbonyl)piperidine-1-yl Imidazole

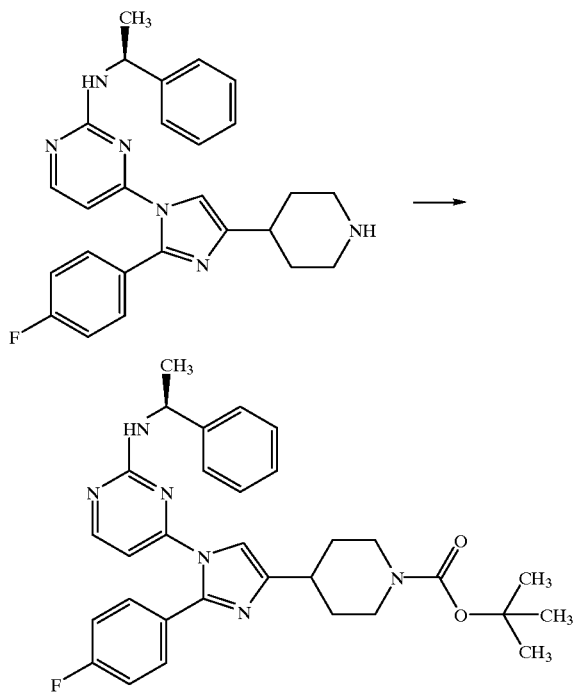

4-Bromo-2-(4-fluorophenyl-1-(2-(S)-phenylethyl)amino-4-pyrimidyl)imidazol (250 mg; 0.57 mmol) is dissolved in THF (3 ml), cooled to –78 C under argon and treated with nBuLi (1.6M solution in hexane; 0.713 ml; 1.14 mmol) at this temperature. After 10 min at –78 C, N-tert.butyloxypiperidine-4-one (114 mg; 0.57 mmol) is added in THF (0.8 ml). Stirring is continued for 5 mm at –78 C, then the reaction mixture poured on a saturated solution of NaCl in water and extracted with TBME three times. The combined organic phases are washed with a saturated solution of NaCl, dried over Na$_2$SO$_4$, filtered and evaporated to dryness. Purification over SiO$_2$ (TBME/hexane 1/1 to 8/2) yielded the title compound as a colorless foam (154 mg; 49%).

1H-NMR (400 MHz; DMSO-d6, 120 C): 1.41 (d, 3H); 1.49 (s, 9H); 1.76 (bd, 2H); 2.00 (dt, 2H); 3.32 (dt, 2H); 3.60–3.71 (m, 2H); 4.49 (s, 1H, OH); 4.81–4.92 (m, 1H); 6.31 (d, 1H); 7.10–7.22 (m, 4H); 7.23–7.31 (m, 4H); 7.48 (bd, 1H, NH); 7.41–7.50 (m, 2H); 8.25 (d, 1H).

MS (m/z; ESI): 559.3 (MH+, 100); 541 (15); 503.3 (70); 485.3 (20).

Example 58

2-(4-Fluorophenyl)-1-(2-(1-(S)-phenylethyl)amino-4-pyrimidyl)-4-(1-hydroxy)piperidine-1-yl Imidazole

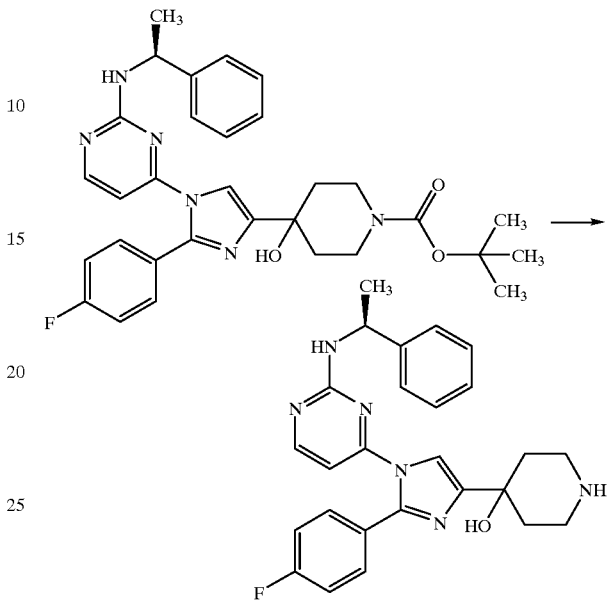

2-(4-Fluorophenyl)-1-(2-(1-(S)-phenylethyl)amino-4-pyrimidyl)-4-(1-hydroxy-4-tert-butyloxycarbonyl)piperidine-1-yl imidazole (105 mg; 0.188 mmol) is treated with EtOH/HClconc (4 m; 1:1) for 10 min at room temperature. The reaction mixture is washed twice with TBME, the aqueous phase is made alkaline by adding a saturated solution of Na$_2$CO$_3$ and extracted three times with TBME. The combined organic phases are washed with a saturated solution of NaCl, dried over Na$_2$SO$_4$, filtered and evaporated to dryness, yielding the title compound as a white foam (72 mg; 84%).

1H-NMR (400 MHz; DMSO-d6) mixture of rotamers. 1.25–1.36 (m, 3H); 1.61 (bd, 2H); 1.95 (bt, 2H); 2.65–2.72 (m, 2H); 2.89 (bt, 2H); 4.48 (bs, 1H); 4.71 (s, 1H, OH); 6.48 (s, 1H); 7.15–7.48 (m, 8H); 7.43 (bs, 2H); 8.02 (d, 1H, NH); 8.28 (s, 1H).

MS (m/z; ESI): 459.2 (MH+, 100); 360.1 (10); 250.7(50); 230.1 (60).

Example 59

2-(4-Fluorophenyl)-1-(2-(1-(S)-phenylethyl)amino-4-pyrimidyl)-4-(3a-hydroxy-N-tert.butyloxycarbonylnortropan-3b-yl)imidazole

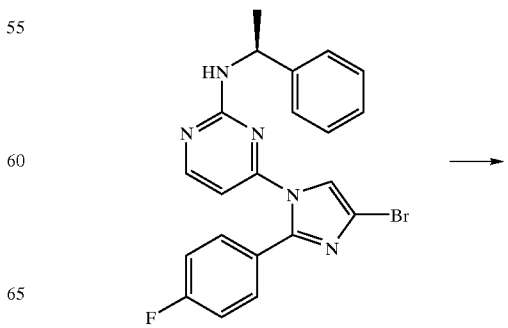

-continued

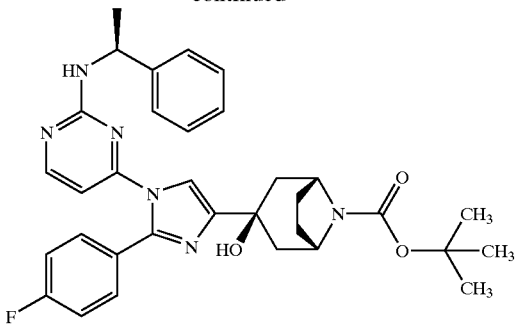

4-(Bromo-2-(4-fluorophenyl)-1-(2-(1-(S)-phenylethyl) amino-4-pyrimidyl)imidazol (150 mg, 0.342 mmol) is dissolved in THF (3 ml), cooled to −78 C under argon and treated with nBuLi (1.6M solution in hexane; 0.428 ml; 0.685 mmol) at this temperature. After 10 min at −78 C, N-tert. Butyloxy nortropinone (77 mg, 0.34 mmol) is added in THF (0.8 ml). Stirring is continued for 5 min at −78 C, then the reaction mixture poured on a saturated solution of NaCl in water and extracted with TBME three times. The combined organic phases are washed with a saturated solution of NaCl, dried over $Na_2SO_4$, filtered and evaporated to dryness. Purification over $SiO_2$ (acetone/hexane 15/85) yields the title compound as a colorless foam (67 mg, 34%).

1H-NMR (400 MHz; DMSO-d6) NMR mixture of rotamers. 1.31 (bs, 3H); 1.43 (s, 9H); 1.68–1.88 (m, 4H); 2.21–2.49(m, 4H); 4.11 (bs 2H), 4.50 (bs, 1H); 4.97 (s, 1H, OH); 6.18 (bs, 0.3H); 6.48 (bs, 0.7H); 7.15–7.35 (m, 8H); 7.37–7.45 (m, bt, 2H); 8.20 (bs, 1H); 8.28 (bs, 1H).

MS (m/z; ESI): 585.3 (MH+, 100).

Example 60

2-(4-Fluorophenyl)-1-(2-(1-(S)-phenylethyl)amino-4-pyrimidyl)-4-(3a-hydroxy-nortropan-3b-yl) imidazole

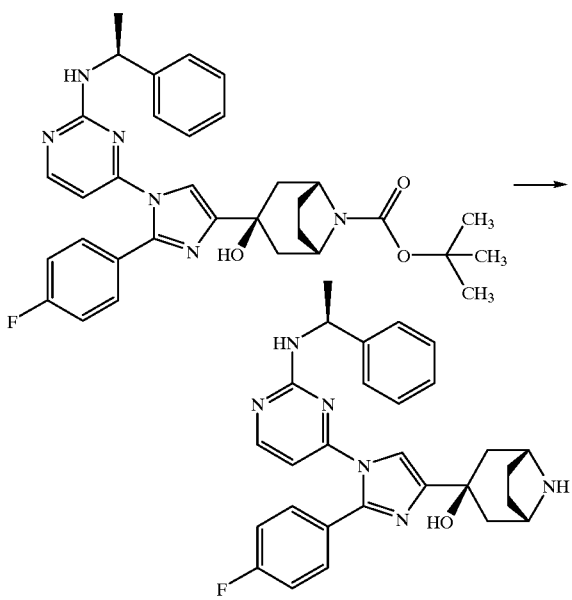

2-(4-Fluorophenyl)-1-(2-(1-(S)-phenylethyl)amino-4-pyrimidyl-(3a-hydroxy-N-tert.butyloxy-carbonylnortropan-3b-yl) imidazole (54 mg; 0.098 mmol) is dissolved in EtOH/HClconc (4 ml; 1:1) and stirred at room temperature for 10 min. Water is added and the aqueous phase washed once with TBME, adjusted to pH>10 by adding a saturated solution of $Na_2CO_3$ and extracted three times with TBME. The combined organic phases were washed with a saturated solution of NaCl, dried over $Na_2SO_4$, filtered and evaporated to dryness to yield the title compound as a white foam (44 mg, 98%).

1H-NMR (400 MHz; DMSO-d6) NMR mixture of rotamers. 1.23–1.48 (m, 3H); 1.58–1.66 (M, 2H); 1.77 (d, 2H); 2.18 (bd, 2H); 2.22 (d, 2H); 3.41 (bs, 2H); 4.48 (bs, 1H); 4.63 (s, 1H, OH); 6.13 (bs, 0.3H); 6.48 (bs, 0.7); 7.16 (m, 8H); 7.40–7.47 (bt, 2H); 8.00 (d, 1H); 8.26 (bs, 1H).

MS (m/z; ESI): 485 (MH+, 100); 284.3 (20); 263.7 (10).

Example 61

2-(4-Fluorophenyl)-1-(2-(1-(S)-phenylethyl)amino-4-pyrimidyl)-4-(4-acetyl)piperidine-1-yl Imidazole

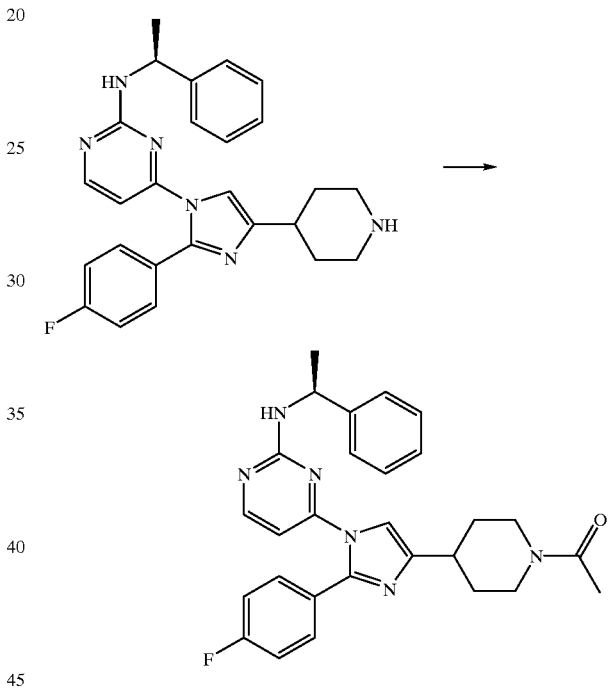

2-(4-Fluorophenyl)-1-(2-(1-(S)-phenylethyl)amino-4-pyrimidyl)-1-yl imidazole (20 mg; 0.045 mmol) dissolved in THF (0.5 ml), NEt3 (0.006 ml; 0.045 mmol) and DMAP (0.5 mg, 0.0045 mmol is treated with acetylchloride (0.0032 ml; 0.045 mmol) for 10 min at room temperature. The reaction mixture poured on a saturated solution of $Na_2CO_3$ and extracted with TBME three times. The combined organic phases are washed with a saturated solution of NaCl, dried over $Na_2SO_4$, filtered and evaporated to dryness. Purification over $SiO_2$ (acetone/hexane 1/1 to 1/0) yields the title compound as a colorless solid (12 mg; 57%).

1H-NMR (400 MHz; DMSO-d6, 120 C): 1.42 (d, 3H); 1.51–1.67 (bq, 2H); 1.99 (bs, 2H); 2.05 (s, 3H); 2.88 (bs, 1H); 3.02 (bs, 2H); 3.95–4.20 (bs, 2H); 4.30–4.40 (m, 1H); 6.30 (d, 1H); 7.10–7.32 (m, 8H); 7.35 (d, 1H; NH); 7.45 (dd, 2H); 8.25 (d, 1H).

MS (m/z; ESI): 485.3 (MH+).

The Agents of the Invention, as defined above, e.g., of formula I, particularly as exemplified, in free or pharmaceutical acceptable acid addition salt form, exhibit pharmacological activity and are useful as pharmaceuticals, e.g. for therapy, in the treatment of diseases and conditions as hereinafter set forth.

In particular Agents of the Invention possess p38 MAP kinase (Mitogen Activated Protein Kinase) inhibiting activity. Thus the Agents of the Invention act to inhibit production of inflammatory cytokines, such as TNF-α and IL-1, and also to potentially block the effects of these cytokines on their target cells. These and other pharmacological activities of the Agents of the invention as may be demonstrated in standard test methods for example as described below:

p38 MAP Kinase Assay

The substrate (GST-ATF-2; a fusion protein comprising amino acids 1–109 of ATF-2 and the GST protein obtained by expression in E. coli) is coated onto the webs of microtiter plates (50 μl/well; 1 μg/ml in PBS/0.02% Na azide) overnight at 4° C. The following day, the microtiter plates are washed four times with PBS/0.5% Tween 20/0.02% Na azide and are blocked with PBS/2% BSA/0.02% Na Azide for 1 h at 37° C. Plates are washed again 4 times with PBS/0.5% Tween 20/0.02% Na azide. The kinase cascade reaction is then started by adding the following reactants in 10 μl aliquots to a final reaction volume of 50 μl.

1. Agents of the Invention titrated from 10 to 0.001 μM in 10-fold dilutions or solvent (DMSO) or $H_2O$.
2. Kinase buffer (5×); pH 7.4; 125 mM Hepes (Stock at 1M; Gibco #15630-056), 125 mM β-glycerophosphate (Sigma #G-6251):125 mM $MgCl_2$ (Merck #5833); 0.5 mM Sodium orthovanadate (Sigma #5-6508), 10 mM DTT (Boehringer Mannheim #708992). The (5×) kinase buffer must be prepared fresh the day of the assay from 5× stock solutions kept at RT. DTT is kept at −20° C. and is added as the last reagent.
3. His-p38 MAP kinase (10 ng/well; Novartis—a fusion protein comprising full length murine p38 MAP kinase and a His tag, obtained by expression in E. coli)
4. cold ATP (final concentration 120 μM; Sigma #A-9187)
5. Water After 1 h at 37° C. the kinase reaction is terminated by washing the plates four times as previously described. Phosphorylated GST-ATF-2 is then detected by adding:

1. the PhosphoPlus ATF-2 (Thr71) Antibody (50 μl/well; 1/1000 final dilution in PBS/2% BSA/0.02% Na Azide; New England Biolabs #9221L) for 90 min at RT.
2. Biotin labelled goat-anti-rabbit IgG (50 μl/well; 1/3000 final dilution in PBS/2% BSA/0.02% Na Azide; Sigma #B-9642) for 90 min at RT.
3. Streptavidin-alkaline phosphatase (50 μl/well; 1/5000 dilution in PBS/2% BSA/0.02% Na Azide; Jackson Immunoresearch #016-050-84) for 30 min at RT.
4. Substrate (100 μl/well; Sigma 104 Phosphatase substrate tablets, 5 mg/tablet; #104-105; 1 mg/ml in substrate buffer, Diethanolamine (97 ml/l; Merck #803116)+ $MgCl_2.6H_2O$ (100 mg/l; Merck #5833)+Na Azide (0.2 g/l)+ HCl 1M to pH 9.8) 30 min at RT.

After step 1, 2 and 3 the microtiter plates are washed four times with PBS/0.5% Tween 20/0.02% Na azide. After step 4, the plates are read in a Bio-Rad microplate reader in a dual wavelength mode (measurement filter 405 mm and reference filter 490 mm). The background value (without ATP) is subtracted and $IC_{50}$ values are calculated using the Origin computer program (4 parameter logistic function).

Agents of the Invention typically have $IC_{50}$s for p38 MAP kinase inhibition in the range from about 100 nM to about 10 nM or less when tested in the above assay. For example the compounds of Examples 9, 14, 15, 18–23, 30–33, 35, 49, 51, 52 and 55–57 have $IC_{50}$s for p38 MAP kinase inhibition in the range from about 1 nM to about 10 nM when tested in the above assay.

Assay for Inhibition of TNF-α Release from hPBMCs

Human peripheral blood mononuclear cells (hPBMCs) are prepared from the peripheral blood of healthy volunteers using ficoll-hypaque density separation according to the method of Hansell et al., J. Imm. Methods (1991) 145: 105. and used at a concentration of $10^5$ cells/well in RPMI 1640 plus 10% FCS. Cells are incubated with serial dilutions of the test compounds for 30 minutes at 37° C. prior to the addition of IFNg (100 U/ml) and LPS (5 mg/ml) and subsequently further incubated for three hours. Incubation is tested by centrifugation at 1400 RPM for 10 min. TNF-α in the supernatant is measured using a commercial ELISA (Innotest hTNFa, available from Innogenetics N.V., Zwijnaarde, Belgium). Agents of the Invention are tested at concentrations of from 0 to 10 mM. Exemplified Agents of the Invention typical suppress TNF release in this assay with an $IC_{50}$ of from about 500 nM to about 10 nM or less when tested in this assay. For instance the compounds of Examples 4, 8, 9, 19, 20, 23, 31–33, 35 and 49–57, 59 and 60 have $IC_{50}$s in the range from about 10 nM to about 1 nM.

Assay for Inhibition of TNF-α Production in LPS Stimulated Mice

Injection of lipopolysaccharide (LPS) induces a rapid release of soluble tumour necrosis factor (TNF-α) into the periphery. This model is be used to analyse prospective blockers of TNF release in vivo.

LPS (20 mg/kg) is injected i.v. into OF1 mice (female, 8 week old). One (1) hour later blood is withdrawn from the animals and TNF levels are analysed in the plasma by an ELISA method using an antibody to TNF-α. Using 20 mg/kg of LPS levels of up to 15 ng of TNF-α/ml plasma are usually induced. Compounds to be evaluated are given either orally or s.c. 1 to 4 hours prior to the LPS injection. Inhibition of LPS-induced TNF-release is taken as the readout.

Agents of the Invention typically inhibit TNF production to the extent of up to about 50% or more in the above assay when administered at 10 mg/kg p.o.

As indicated in the above assays Agents of the Invention are potent inhibitors of TNF-α release. Accordingly, the Novel Compounds have pharmaceutical utility as follows:

Agents of the Invention are useful for the prophylaxis and treatment of diseases or pathological conditions mediated by cytokines such as TNFα and IL-1, e.g., inflammatory conditions, autoimmune diseases, severe infections, and organ or tissue transplant rejection, e.g. for the treatment of recipients of heat, lung, combined heart-lung, liver, kidney, pancreatic, skin or corneal transplants and for the prevention of graft-versus-host disease, such as following bone marrow transplants.

Agents of the Invention are particularly useful for the treatment, prevention, or amelioration of autoimmune disease and of inflammatory conditions, in particular inflammatory conditions with an aetiology including an autoimmune component such as arthritis (for example rheumatoid arthritis, arthritis chronica progrediente and arthritis deformans) and rheumatic diseases. Specific auto-immune diseases for which Agents of the Invention may be employed include autoimmune haematological disorders (including e.g. hemolytic anaemia, aplastic anaemia pure red cell anaemia and idiopathic thrombocytopenia), systemic lupus erythematosus, polychondritis, sclerodoma, Wegener granulamatosis, dermatomyositis, chronic active hepatitis, myasthenia gravis, psoriasis, Steven-Johnson syndrome, idiopathic sprue, autoimmune inflammatory bowel disease (including e.g. ulcerative colitis and Crohn's disease), endocrine ophthalmopathy, Graves disease, sacroidosis, multiple sclerosis, primary biliary cirrhosis, juvenile diabetes (diabetes mellitus type I), uveitis (anterior and posterior), keratoconjunctivitis sicca and vernal keratoconjunctivitis, interstitial lung fibrosis, psoriatic arthritis and glomerulonephritis (with and without nephrotic syndrome, e.g. including idiopathic nephrotic syndrome or minimal change nephropathy).

Agents of the Invention are also useful for the treatment, prevention, or amelioration of asthma, bronchitis, pneumoconiosis, pulmonary emphysema, and other obstructive or inflammatory diseases of the airways.

Agents of the Invention are useful for treating undesirable acute and hyperacute inflammatory reactions which are mediated by TNF, especially by TNFa, e.g., acute infections, for example septic shock (e.g., endotoxic shock and adult respiratory distress syndrome), meningitis, pneumonia; and severe burns; and for the treatment of cachexia or wasting syndrome associated with morbid TNF release, consequent to infection, cancer, or organ dysfunction, especial AIDS-related cachexia, e.g., associated with or consequential to HIV infection.

Agents of the Invention are particularly useful for treating diseases of bone metabolism including osteoarthritis, osteoporosis and other inflammatory arthritides.

For the above indications the appropriate dosage will, of course, vary depending, for example, on the particular Agent of the Invention employed, the subject to be treated, the mode of administration and the nature and severity of the condition being treated. However, in general, satisfactory results in animals are obtained at daily dosages of from about 1 to about 10 mg/kg/day p.o. In larger mammals, for example humans, an indicated daily dosage is in the range of from about 50 to about 750 mg of Novel Compound administered orally once or, more suitably, in divided dosages two to four times/day.

The Novel Compounds may be administered by any conventional route, e.g. orally, for example in the form of solutions for drinking, tablets or capsules or parenterally, for example in the form of injectable solutions or suspensions. Normally for system administration oral dosage forms are preferred, although for some indications the Novel Compounds may also be administered topically or dermally, e.g. in the form of a dermal cream or gel or like preparation or, for the purposes of application to the eye, in the form of an ocular cream, gel or eye-drop preparation; or may be administered by inhalation, e.g., for treating asthma. Suitable unit dosage forms for oral administration comprise e.g. from 25 to 250 mg Novel Compound per unit dosage.

In accordance with the foregoing the present invention also provides in a further series of embodiments.

A. A method of inhibiting production of soluble TNF, especially TNFα, or of reducing inflammation in a subject (i.e., a mammal, especial a human) in need of such treatment which method comprises administering to said subject an effective amount of an Agent of the Invention, or a method of treating any of the above mentioned conditions, particularly a method of treating an inflammatory or autoimmune disease or condition, e.g. rheumatoid arthritis, or alleviating one or more symptoms of any of the above mentioned conditions.

B. An Agent of the Invention for use as a pharmaceutical, e.g. for use as an immunosuppressant or antiinflammatory agent or for use in the prevention, amelioration or treatment of any disease or condition as described above, e.g., an autoimmune or inflammatory disease or condition.

C. A pharmaceutical composition comprising an Agent of the Invention in association with a pharmaceutically acceptable diluent or carrier, e.g., for use as an immunosuppressant or anti-inflammatory agent or for use in the prevention, amelioration or treatment of any disease or condition as described above, e.g., an autoimmune or inflammatory disease or condition.

D. Use of an Agent of the Invention in the manufacture of a medicament for use as an immunosuppressant or anti-inflammatory agent or for use in the prevention, amelioration or treatment of any disease or condition as described above, e.g., an autoimmune of inflammatory disease or condition.

What is claimed is:

1. A compound of formula (I)

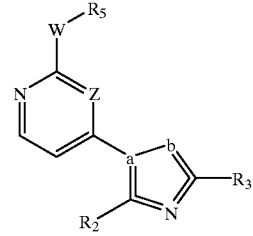

wherein
a is N or C;
b is CH when a is N, or O when a is C;
═ denotes a single or a double bond dependent upon whether the azole ring is an imidazole or an oxazole ring;
Z is N or CH;
W is —NR$_6$—Y—, —O— or —S—,
where
R$_6$ is H, C$_1$–C$_4$alkyl, C$_3$–C$_8$cycloalkyl, C$_3$–C$_8$cycloalkylC$_1$–C$_3$alkyl, C$_6$–C$_{18}$aryl, C$_3$–C$_{18}$heteroaryl, C$_7$–C$_{19}$aralkyl or C$_4$–C$_{19}$heteroaralkyl and
—Y— is C$_1$–C$_4$alkylene or a direct bond;
R$_2$ is phenyl, optionally substituted by one or more substituents, each of which is, independently, selected from halo, CF$_3$, cyano, amido or thioamido, carboxylate or thiocarboxylate, C$_1$–C$_4$alkoxy, C$_1$–C$_4$alkyl, or NH$_2$ which is optionally mono- or di-N-C$_1$–C$_4$alkyl substituted;
R$_3$ is H, halogen, C$_1$–C$_{10}$alkyl, C$_1$–C$_4$alkenyl, C$_3$–C$_{10}$cycloalkyl, C$_3$–C$_{18}$heterocycloalkyl, C$_6$–C$_{18}$aryl, C$_3$–C$_{18}$heteroaryl or methyleneaminoguanidinyl, each of which, except H and halogen, is optionally substituted by up to 4 substituents separately selected from C$_1$–C$_4$alkyl optionally substituted by hydroxy, halogen, halo-substituted-C$_1$–C$_4$alkyl, hydroxy, C$_1$–C$_4$alkoxy, C$_1$–C$_4$alkylthio, carboxy, optionally C$_1$–C$_6$alkyl or C$_1$–C$_6$alkoxy substituted carbonyl, optionally mono- or di-N-C$_1$–C$_4$alkyl substituted amino, or by N-heterocyclyl having from 5- to 7-ring atoms and optionally having a further hetero atom; and
R$_5$ is C$_6$–C$_{18}$aryl, C$_3$–C$_{18}$heteroaryl or C$_3$–C$_{12}$cycloalkyl each of which is optionally substituted by up to 4 substituents separately selected from C$_1$–C$_4$alkyl, halogen, halo substituted C$_1$–C$_4$alkyl, hydroxy, C$_1$–C$_4$alkoxy, C$_1$–C$_4$alkylthio, or optionally mono- or di-N-C$_1$–C$_4$alkyl substituted amino, or by N-heterocyclyl having from 5- to 7-ring atoms and optionally having a further hetero atom;
or pharmaceutically-acceptable esters thereof, or acid addition salts thereof, or, when said compound comprises one or more free hydroxyl groups, the pharmaceutically-acceptable prodrug esters thereof, which are cleavable under physiological conditions to release the compound having one or more free hydroxyl groups.

2. A compound of formula (II)

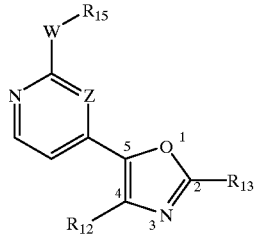

wherein

Z is N or CH;

W is —$NR_6$—Y—, —O— or —S—,
where
$R_6$ is H, $C_1$–$C_4$alkyl, $C_3$–$C_8$cycloalkyl, $C_3$–$C_8$cycloalkyl$C_1$–$C_3$alkyl, $C_6$–$C_{18}$aryl, $C_3$–$C_{18}$heteroaryl, $C_7$–$C_{19}$aralkyl or $C_4$–$C_{19}$heteroaralkyl and
—Y— is $C_1$–$C_4$alkylene or a direct bond;

$R_{12}$ is phenyl, optionally substituted by one or more substituents, each of which is, independently, selected from halo, $CF_3$, cyano, amido or thioamido, carboxylate or thiocarboxylate, $C_1$–$C_4$alkoxy, $C_1$–$C_4$alkyl, or $NH_2$ which is optionally mono- or di-N-$C_1$–$C_4$alkyl substituted;

$R_{13}$ is H, halogen, $C_1$–$C_{10}$alkyl, $C_1$–$C_4$alkenyl, $C_3$–$C_{10}$cycloalkyl, $C_3$–$C_{18}$heterocycloalkyl, $C_6$–$C_{18}$aryl, $C_3$–$C_{18}$heteroaryl or methyleneaminoguanidinyl, each of which, except H or halogen, is optionally substituted by up to 4 substituents separately selected from $C_1$–$C_4$alkyl optionally substituted by hydroxy, halogen, halo-substituted-$C_1$–$C_4$alkyl, hydroxy, $C_1$–$C_4$alkoxy, $C_1$–$C_4$alkylthio, carboxy, optionally $C_1$–$C_6$alkyl or $C_1$–$C_6$alkoxy substituted carbonyl, optionally mono- or di-N-$C_1$–$C_4$alkyl substituted amino, or by N-heterocyclyl having from 5- to 7-ring atoms and optionally having a further hetero atom; and $R_{15}$ is $C_6$–$C_{18}$aryl, $C_3$–$C_{18}$heteroaryl or $C_3$–$C_{12}$cycloalkyl each of which is optionally substituted by up to 4 substituents separately selected from $C_1$–$C_4$alkyl, halogen, halo-substituted-$C_1$–$C_4$alkyl, hydroxy, $C_1$–$C_4$alkoxy, $C_1$–$C_4$alkylthio or optionally mono- or di-N-$C_1$–$C_4$alkyl substituted amino, or by N-heterocyclyl having from 5- to 7-ring atoms and optionally having a further hetero atom;

or pharmaceutically-acceptable esters thereof, or acid addition salts thereof, or, when said compound comprises one or more free hydroxyl groups, the pharmaceutically-acceptable prodrug esters thereof, which are cleavable under physiological conditions to release the compound having one or more free hydroxyl groups.

3. A compound according to claim 2 of formula (II')

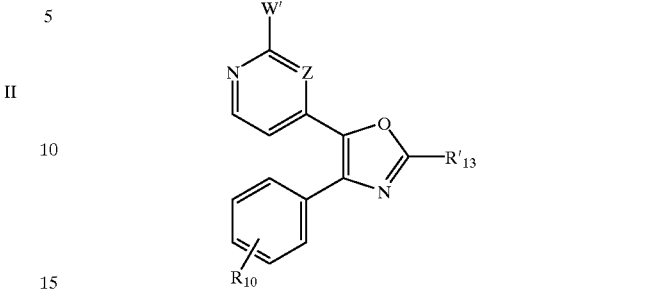

wherein $R'_{15}$ is phenyl or $C_3$–$C_7$cycloalkyl each of which is optionally mono-substituted by halogen, $C_1$–$C_{10}$alkyl, $C_1$–$C_{10}$alkoxy, hydroxy, trihalomethyl or —$NR_7R_8$, where $R_7$ and $R_8$ are, independently, H or $C_1$–$C_4$alkyl;

$R_{10}$ is halogen, $CF_3$, cyano, amido, thioamido, amino $C_1$–$C_6$alkyl;

$R'_{13}$ is H, $C_1$–$C_6$alkyl, $C_1$–$C_4$alkenyl, phenyl, pyridyl, morpholinyl, piperidinyl, piperazinyl or N-mono- or di-$C_1$–$C_4$alkylamino, each of which, except H, is optionally substituted by up to 2 substituents, separately selected from $C_1$–$C_4$alkyl optionally substituted by hydroxy, halogen, hydroxy, $C_1$–$C_4$alkoxy, carboxy, optionally $C_1$–$C_6$alkyl or $C_1$–$C_6$alkoxy substituted carbonyl, or optionally mono- or di-N-$C_1$–$C_4$alkyl substituted amino;

Z is N or CH; and

W' is —NH—Y'—, —O— or —S—, where Y' is —$CH_2$—, —$CH_2$—$CH_2$—, —$CH(CH_3)$— or a direct bond;

or pharmaceutically-acceptable esters thereof, or acid addition salts thereof, or, when said compound comprises one or more free hydroxyl groups, the pharmaceutically-acceptable prodrug esters thereof, which are cleavable under physiological conditions to release the compound having one or more free hydroxyl groups.

4. A compound according to claim 2 selected from:

4-(4-Fluorophenyl)-5-(2-[1-(S)-phenylethyl]amino-4-pyrimidyl)-2-N-morpholinyloxazole;

4-(4-Fluorophenyl)-5-(2-[1-(S)-phenylethyl]amino-4-pyrimidyl)-2-N-piperidinyloxazole;

4-(4-Fluorophenyl)-5-(2-[1-(S)-phenylethyl]amino-4-pyrimidyl)-2-(4-ethoxy-carbonylpiperazin-1-yl)oxazole;

4-(4-Fluorophenyl)-5-(2-[1-(S)-phenylethyl]amino-4-pyrimidyl)-2-(4-methyl-piperidine-1-yl)oxazole;

4-(4-Fluorophenyl)-5-(2-[1-(S)-phenylethyl]amino-4-pyrimidyl)-2-(4-ethyl-piperazin-1-yl)oxazole;

4-(4-Fluorophenyl)-5-(2-[1-(S)-phenylethyl]amino-4-pyrimidyl)-2-N,N-diethyl-aminooxazole;

4-(4-Fluorophenyl)-5-(2-[1-(S)-phenylethyl]amino-4-pyrimidyl)-2-(4-NH-piperidine-1-yl)oxazole;

4-(4-Fluorophenyl)-5-(2-[1-(S)-phenylethyl]amino-4-pyrimidyl)-2-(4-N-acetyl-piperidine-1-yl)oxazole;

4-(4-Fluorophenyl)-5-(2-[1-(S)-phenylethyl]amino-4-pyrimidyl)-2-(4-pyridyl)oxazole;

4-(4-Fluorophenyl)-5-(2-[1-(S)-phenylethyl]amino-4-pyrimidyl)-2-(1-piperazinyl)oxazole;

4-(4-Fluorophenyl)-5-(2-[1-(S)-phenylethyl]amino-4-pyrimidyl)-2-(1-amino-1-methyl)ethyloxazole;

4-(4-Fluorophenyl)-5-(2-[1-(S)-phenylethyl]amino-4-pyrimidyl)-2-(1-hydroxy-4-methylpiperidine-1-yl)oxazole;

4-(4-Fluorophenyl)-2-(1-hydroxy-4-methyl)piperidine-1-yl)-5-(2-[cyclopropylmethyl]amino-4-pyridyl)oxazole;

4-(4-Fluorophenyl)-2-(4-NH-piperidine-1-yl)-5-(2-(S)-phenylethyl)amino-4-pyridyl)oxazole;

4-(4-Fluorophenyl)-2-(4-NH-piperidine-1-yl)-5-(2-cyclopropylmethylamino-4-pyridyl)oxazole;

4-(4-Fluorophenyl)-2-(4-N-(2-hydroxy-2-methyl)propylpiperidine-1-yl)-5-(2-cyclopropylmethylamino-4-pyridyl)oxazole;

4-(4-Fluorophenyl)-5-(2-cyclopropylmethylamino-4-pyrimidyl)-2-(4-NH-piperidine-1-yl)oxazole;

4-(4-Fluorophenyl)-2-(1-hydroxy-4-ethyl)piperidin-1-yl)-5-(2-cyclohexylamino-4-pyridyl)oxazole;

4-(4-Fluorophenyl)-2-(1-hydroxy-4-ethyl-piperidin-1-yl)-5-(2-cyclopropylamino-4-pyridyl)oxazole;

4-(4-Fluorophenyl)-2-(4-N-(2-hydroxy-2-methyl)propylpiperidine-1-yl)-5-(2-cyclohexylamino-4-pyridyl)oxazole;

4-(4-Fluorophenyl)-2-(4-N-(2-hydroxy-2-methyl)propylpiperidine-1-yl)-5-(2-cyclopropylamino-4-pyridyl)oxazole;

4-(4-Fluorophenyl)-2-(4-N-(2-hydroxy-2-methyl)propylpiperidine-1-yl)-5-(2-(1-(S)-phenylethyl)amino-4-pyrimidyl)oxazole;

4-(4-Fluorophenyl)-2-(4-NH-piperidine-1-yl)-5-(2-cyclohexylamino-4-pyridyl)oxazole, and 4-(4-Fluorophenyl)-2-(4-N-(2-hydroxy-2-methyl)propylpiperidine-1-yl)-5-(2-(1-(S)-phenylethyl)amino-4-pyrimidyl)oxazole.

5. A compound according to claim 1 of formula (III)

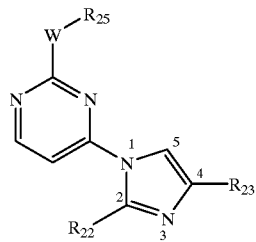

wherein

W is —NR$_6$—Y—, —O— or —S—, where

R$_6$ is H, C$_1$–C$_4$alkyl, C$_3$–C$_8$cycloalkyl, C$_3$–C$_8$cycloalkylC$_1$–C$_3$alkyl, C$_6$–C$_{18}$aryl, C$_3$–C$_{18}$heteroaryl, C$_7$–C$_{19}$aralkyl or C$_4$–C$_{19}$heteroaralkyl and —Y— is C$_1$–C$_4$alkylene or a direct bond;

R$_{22}$ is phenyl, optionally substituted by one or more substituents, each of which is, independently, selected from halo, CF$_3$, cyano, amido or thioamido, carboxylate or thiocarboxylate, C$_1$–C$_4$alkoxy, C$_1$–C$_4$alkyl or NH$_2$ which is optionally mono- or di-N-C$_1$–C$_4$alkyl substituted;

R$_{23}$ is H, halogen, C$_1$–C$_{10}$alkyl, C$_1$–C$_4$alkenyl, C$_3$–C$_{10}$cycloalkyl, C$_3$–C$_{18}$heterocycloalkyl, C$_6$–C$_{18}$aryl, C$_3$–C$_{18}$heteroaryl or methyleneaminoguanidinyl, each of which, except H or halogen, may be optionally substituted by up to 4 substituents separately selected from C$_1$–C$_4$alkyl optionally substituted by hydroxy, halogen, halo-substitued-C$_1$–C$_4$alkyl, hydroxy, C$_1$–C$_4$alkoxy, C$_1$–C$_4$alkythio, carboxy, optionally C$_1$–C$_6$alkyl or C$_1$–C$_6$alkoxy substituted carbonyl, optionally mono- or di-N-C$_1$–C$_4$alkyl substituted amino, or by N-heterocyclyl having from 5- to 7-ring atoms and optionally having a further hetero atom; and R$_{25}$ is C$_6$–C$_{18}$aryl, C$_3$–C$_{18}$heteroaryl or C$_3$–C$_{12}$cycloalkyl each of which is optionally substituted by up to 4 substituents separately selected from C$_1$–C$_4$alkyl, halogen, halo-substitued-C$_1$–C$_4$alkyl, hydroxy, C$_1$–C$_4$alkoxy, C$_1$–C$_4$alkylthio or optionally mono- or di-N-C$_1$–C$_4$alkyl substituted amino, or by N-heterocyclyl having from 5- to 7-ring atoms and optionally having a further hetero atom;

or pharmaceutically-acceptable esters thereof, or acid addition salts thereof, or, when said compound comprises one or more free hydroxyl groups, the pharmaceutically-acceptable prodrug esters thereof, which are cleavable under physiological conditions to release the compound having one or more free hydroxyl groups.

6. A compound according to claim 1, of formula III'

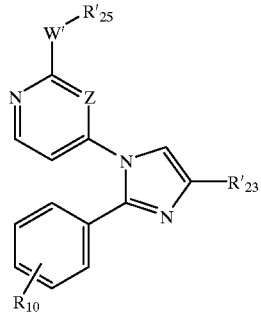

wherein

R'$_{25}$ is phenyl or C$_3$–C$_7$cycloalkyl each of which is optionally mono-substituted by halogen, C$_1$–C$_{10}$alkyl, C$_1$–C$_{10}$alkoxy, hydroxy, trihalomethyl or —NR$_7$R$_8$, where R$_7$ and R$_8$ are independently H, C$_1$–C$_6$alkyl, C$_6$–C$_{10}$aryl, C$_6$–C$_{10}$heteroaryl C$_7$–C$_{11}$aralkyl or C$_7$–C$_{11}$heteroaralkyl;

R$_{10}$ is halogen, CF$_3$, cyano, amido, thioamido, amino or C$_1$–C$_6$alkyl;

R'$_{23}$ is H, halogen, C$_1$–C$_6$alkyl, vinyl, phenyl, pyridyl, pyrimidyl, benzofuryl, furyl, thienyl, morpholinyl, piperidinyl, nortropanyl, piperazinyl, methyleneaminoguanidinyl or N-mono- or di-C$_1$–C$_4$alkylamino, each of which is optionally substituted, e.g. by up to 2 substituents, separately selected from C$_1$–C$_4$alkyl optionally substituted by hydroxy, halogen, hydroxy, C$_1$–C$_4$alkoxy, carboxy, optionally C$_1$–C$_6$alkyl or C$_1$–C$_6$alkoxy substituted carbonyl, optionally mono- or di-N-C$_1$–C$_4$alkyl substituted amino, or by N-heterocyclyl containing from 5 to 7 ring atoms and optionally containing a further hetero atom, and W' is —NH—Y'—, —O— or —S—, where Y' is CH$_2$—, —CH$_2$—CH$_2$—, —CH(CH$_3$)— or a direct bond, or a pharmaceutically-acceptable and -cleavable esters thereof or an acid addition salt thereof.

7. A compound according to claim 5 selected from

3-Bromo-2-(4-fluorophenyl)-1-(2-[1-(S)-phenylethyl]amino-4-pyrimidyl)imidazole;

4-Bromo-2-(4-fluoromethylphenyl)-1-(2-cyclohexylamino-4-pyrimidyl)imidazole;

4-Bromo-2-(3-trifluoromethylphenyl)-1-(2-cyclopentylamino-4-pyrimidyl)imidazole;
4-Bromo-2-(3-trifluoromethylphenyl)-1-(2-cyclopropylamino-4-pyrimidyl)imidazole;
2-(4-Fluorophenyl)-4-(1-methyl-4-hydroxypiperidin-4-yl)-1-(2-[1-(S)-phenyl-ethyl]amino-4-pyrimidyl)imidazole;
2-(4-Fluorophenyl)-1-(2-[1-(S)-phenyl-ethyl]amino-4-pyrimidyl)4-vinylimidazole;
2-(4-Fluorophenyl)-1-(2-[1-(S)-phenyl-ethyl]amino-4-pyrimidyl)4-(4-pyridyl)-imidazole;
2-(4-Fluorophenyl)-1-(2-[1-(S)-phenyl-ethyl]amino-4-pyrimidyl)4-(2-pyridyl)-imidazole;
2-(4-Fluorophenyl)-1-(2-[1-(S)-phenyl-ethyl]amino-4-pyrimidyl)4-(3-pyridyl)-imidazole;
2-(4-Fluorophenyl)-1-(2-[1-(S)-phenyl-ethyl]amino-4-pyrimidyl)4-(2-thienyl)-imidazole;
2-(4-Fluorophenyl)-1-(2-[1-(S)-phenyl-ethyl]amino-4-pyrimidyl)4-(2-furyl)-imidazole;
2-(4-Fluorophenyl)-1-(2-[1-(S)-phenyl-ethyl]amino-4-pyrimidyl)4-(2-amino)pyrimidylimidazole;
2-(4-Fluorophenyl)-1-(2-[1-(S)-phenyl-ethyl]amino-4-pyrimidyl)4-(2-hydroxy)pyrimidylimidazole;
2-(4-Fluorophenyl)-1-(2-[1-(S)-phenyl-ethyl]amino-4-pyrimidyl)4-(2-morpholinyl)pyrimidylimidazole;
2-(4-Fluorophenyl)-1-(2-[1-(S)-phenyl-ethyl]amino-4-pyrimidyl)-4-(3-thienyl)-imidazole;
2-(4-Fluorophenyl)-1-(2-[1-(S)-phenyl-ethyl]amino-4-pyrimidyl)-4-(2-benzofuryl)-imidazole;
2-(4-Fluorophenyl)-1-(2-[1-(S)-phenyl-ethyl]amino-4-pyrimidyl)-4-(5-chlorothiophen-2-yl)imidazole;
2-(4-Fluorophenyl)-1-(2-[1-(S)-phenyl-ethyl]amino-4-pyrimidyl)-4-(4-methoxyphenyl)imidazole;
2-(4-Fluorophenyl)-1-(2-[1-(S)-phenyl-ethyl]amino-4-pyrimidyl)-4-(4-fluorophenyl)imidazole;
2-(4-Fluorophenyl)-1-(2-[1-(S)-phenyl-ethyl]amino-4-pyrimidyl)-4-(3-chloro-4-fluorophenyl)imidazole;
2-(4-Fluorophenyl)-1-(2-[1-(S)-phenyl-ethyl]amino-4-pyrimidyl)-4-(3-chloro phenyl)imidazole;
2-(4-Fluorophenyl)-1-(2-[1-(S)-phenyl-ethyl]amino-4-pyrimidyl)-4-(4-methyleneaminoguanidinyl-imidazole;
2-(4-Fluorophenyl)-1-(2-[1-(S)-phenylethyl]amino-4-pyrimidyl)-4-(4-ethoxycarbonyl)piperidine-1-yl imidazole;
2-(4-Fluorophenyl)-1-(2-[1-(S)-phenylethyl]amino-4-pyrimidyl)-4-piperidine-1-yl imidazole;
2-(4-Fluorophenyl)-1-(2-[1-(S)-phenylethyl]amino-4-pyrimidyl)-4-(4-formyl)-piperidine-1-yl imidazole;
2-(4-Fluorophenyl)-1-(2-[1-(S)-phenylethyl]amino-4-pyrimidyl)-4-(4-(2-hydroxy-2-methyl)propylpiperidine-1-yl imidazole;
2-(4-Fluorophenyl)-1-(2-[1-(S)-phenylethyl]amino-4-pyrimidyl)-4-(4-methyl)-piperidine-1-yl imidazole;
2-(4-Fluorophenyl)-1-(2-[1-(S)-phenylethyl]amino-4-pyrimidyl)-4-(1-hydroxy-4-tert.butyloxycarbonyl)piperidine-1-yl imidazole;
2-(4-Fluorophenyl)-1-(2-[1-(S)-phenyl-ethyl]amino-4-pyrimidyl)-4-(1-hydroxy)piperidine-1-yl imidazole;
2-(4-Fluorophenyl)-1-(2-[1-(S)-phenylethyl]amino-4-pyrimidyl)-4-(3a-hydroxy-N-tert.butyloxycarbonylnortropan-3b-yl) imidazole;
2-(4-Fluorophenyl)-4-(1-methyl-4-hydroxypiperidin-4-yl)-1-(2-cyclohexylamino-4-pyrimidinyl)imidazole;
2-(3-Trifluoromethylphenyl)-4-(1-methyl-4-hydroxypiperidin-4-yl)-1-(2-cyclopropylamino-4-pyrimidyl)imidazole;
2-(3-Trifluoromethylphenyl)-4-(1-methyl-4-hydroxypiperidin-4-yl)-1-(2-cyclopentylamino-4-pyrimidyl)imidazole;
2-(4-Fluorophenyl)-1-(2-cyclopentyl)amino-4-pyrimidyl)-4-(4-(2-hydroxy-2-methyl)propylpiperidine-1-yl imidazole;
2-(4-Fluorophenyl)-1-(2-(1-(S)-phenylethyl)amino-4-pyrimidyl)-4-(3a-hydroxy-nortropan-3b-yl) imidazole; and
2-(4-Fluorophenyl)-1-(2-(1-(S)-phenylethyl)amino-4-pyrimidyl)-4-(4-acetyl)piperidine-1-yl imidazole.

8. A process for the preparation of a compound of formula (II")

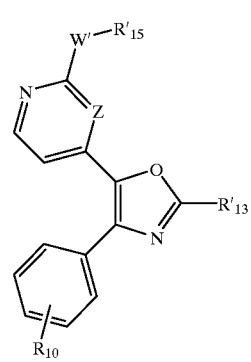

wherein

R'$_{13}$, R'$_{15}$, R$_{10}$ and Z are as defined in claim 3; and

W' is —NH—, which comprises reacting the corresponding precursor compound of formula (IV) or (IV')

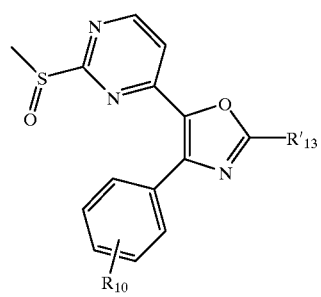

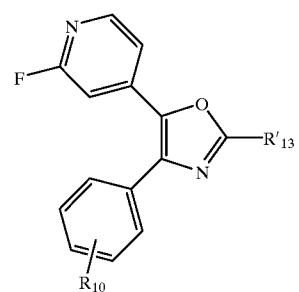

wherein

R'$_{13}$, R$_{10}$ and Z are as defined in claim 3, with the corresponding R'$_{15}$—NH$_2$ amine.

9. A process for the preparation of a compound of formula (III")

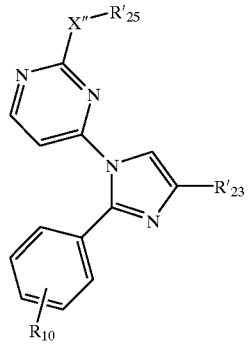

wherein $R'_{23}$, $R'_{25}$ and $R_{10}$ are as defined in claim 5, with the exception that $R'_{23}$ is not H or halogen; and X" is —NH— or —O—, comprising reacting a corresponding compound of formula III" in which $R'_{23}$ is halogen with the corresponding $R'_{23}$ ketone or activated $R'_{23}$ precursor.

10. A process for the preparation of a compound of formula (III") according to claim 9, wherein the halogen is bromine.

11. A process for the preparation of a compound of formula (III") according to claim 9, wherein the $R'_{23}$ precursor is tri-alkylstannyl activated $R'_{23}$ precursor.

12. A pharmaceutical composition comprising an effective amount of a compound according to claim 1 in association with a pharmaceutically acceptable diluent or carrier.

13. A method of inhibiting production of soluble TNF or of reducing inflammation in a subject in need of such treatment which method comprises administering to said subject an effective amount of a compound according to claim 1.

14. A method of inhibiting production of soluble TNF according to claim 13, wherein the soluble TNF is TNFα.

15. A method of treating immunosuppression or inflammation comprising the administration of a pharmaceutically effective amount of a compound according to claim 1.

* * * * *

UNITED STATES PATENT AND TRADEMARK OFFICE
CERTIFICATE OF CORRECTION

PATENT NO. : 6,579,874 B1
DATED : June 17, 2003
INVENTOR(S) : Revesz et al.

It is certified that error appears in the above-identified patent and that said Letters Patent is hereby corrected as shown below:

Column 79,
Line 6, should read as follows:
-- 4-(4-Fluorophenyl)-2-(4-NH-peiperidine-1-yl)-5-(2-(1-(S)- --

Column 80,
Claim 6, should read as follows:

-- 6. A compound according to Claim 1, of formula (III')

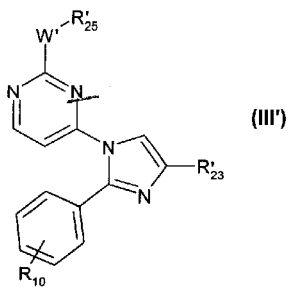

wherein $R'_{25}$ is phenyl or $C_3$-$C_7$cycloalkyl each of which is optionally mono-substituted by halogen, $C_1$-$C_{10}$alkyl, $C_1$-$C_{10}$alkoxy, hydroxy, trihalomethyl or -$NR_7R_8$, where $R_7$ and $R_8$ are, independently, H or $C_1$-$C_4$alkyl;

$R'_{10}$ is halogen, $CF_3$, cyano, amido, thioamido, amino or $C_1$-$C_6$alkyl;

$R'_{23}$ is H, halogen, $C_1$-$C_6$alkyl, vinyl, phenyl, pyridyl, pyrimidyl, benzofuryl, furyl, thienyl, morpholinyl, piperidinyl, nortropanyl, piperazinyl, methyleneaminoguanidinyl or $N$-mono- or di-$C_1$-$C_4$alkylamino, each of which, except H or halogen is optionally substituted by up to 2 substituents, separately selected from $C_1$-$C_4$alkyl optionally substituted by hydroxy, halogen, $C_1$-$C_4$Calkoxy, carboxy, optionally $C_1$-$C_6$alkyl or $C_1$-$C_6$alkoxy substituted carbonyl, optionally mono- or di-$N$-$C_1$-$C_4$alkyl substituted amino, or by $N$-heterocyclyl having from 5- to 7-ring atoms and optionally having a further hetero atom; and W' is -NH-Y'-, -O- or -S-, where Y' is -$CH_2$-, -$CH_2$-$CH_2$-, -$CH(CH_3)$- or a direct bond; or pharmaceutically-acceptable esters thereof, or acid addition salts thereof, or, when said compound comprises one or more free hydroxyl groups, the pharmaceutically-acceptable prodrug esters thereof, which are cleavable under physiological conditions to release the compound having one or more free hydroxyl groups. --

UNITED STATES PATENT AND TRADEMARK OFFICE
CERTIFICATE OF CORRECTION

PATENT NO.    : 6,579,874 B1
DATED         : June 17, 2003
INVENTOR(S)   : Revesz et al.

It is certified that error appears in the above-identified patent and that said Letters Patent is hereby corrected as shown below:

Column 81,
Line 25, should read as follows:
-- pyrimidyl)4-(2-N-morpholinyl)pyrimidylimidazole; --

Signed and Sealed this

Twenty-first Day of October, 2003

JAMES E. ROGAN
*Director of the United States Patent and Trademark Office*